(12) United States Patent
Maiyuran et al.

(10) Patent No.: US 8,986,974 B2
(45) Date of Patent: Mar. 24, 2015

(54) METHODS FOR PRODUCING POLYPEPTIDIES IN PROTEASE-DEFICIENT MUTANTS OF TRICHODERMA

(75) Inventors: Suchindra Maiyuran, Gold River, CA (US); Abigail Jang, Roseville, CA (US); Kimberly Brown, Elk Grove, CA (US); Sandra Merino, West Sacramento, CA (US); Jeffrey Shasky, Davis, CA (US); Eric Abbate, Vacaville, CA (US)

(73) Assignee: Novozymes, Inc., Davis, CA (US)

( * ) Notice: Subject to any disclaimer, the term of this patent is extended or adjusted under 35 U.S.C. 154(b) by 146 days.

(21) Appl. No.: 13/516,433

(22) PCT Filed: Dec. 17, 2010

(86) PCT No.: PCT/US2010/061105
§ 371 (c)(1),
(2), (4) Date: Jun. 15, 2012

(87) PCT Pub. No.: WO2011/075677
PCT Pub. Date: Jun. 23, 2011

(65) Prior Publication Data
US 2012/0288892 A1    Nov. 15, 2012

Related U.S. Application Data

(60) Provisional application No. 61/287,844, filed on Dec. 18, 2009.

(51) Int. Cl.
*C12N 1/15* (2006.01)
*C12N 9/58* (2006.01)
*C12N 15/80* (2006.01)
*C12P 21/02* (2006.01)

(52) U.S. Cl.
CPC ........ *C12N 9/58* (2013.01); *C12N 15/80* (2013.01); *C12P 21/02* (2013.01)
USPC ....................................................... 435/254.1

(58) Field of Classification Search
None
See application file for complete search history.

(56) References Cited

U.S. PATENT DOCUMENTS 5,840,570 A * 11/1998 Berka et al. ............. 435/254.3
6,509,171 B1    1/2003 Berka et al.

FOREIGN PATENT DOCUMENTS

| EP | 0574347 A2 | 4/1993 |
|---|---|---|
| WO | 9600787 A1 | 1/1996 |
| WO | 9722705 A1 | 6/1997 |
| WO | 9726330 A2 | 7/1997 |
| WO | 9812300 A1 | 3/1998 |
| WO | 2006073839 A2 | 7/2006 |
| WO | 2007045248 A1 | 4/2007 |
| WO | 2008027472 A2 | 3/2008 |

OTHER PUBLICATIONS

Dienes et al, 2007, Enzy Microbiol Technol 40(5), 1087-1094.
Goto et al, 1992, Biosci Biotechnol Biochem 56(10), 1523-1528.
Homberg et al, 1997, Trends Biotechnol 15(7), 256-263.
Janas et al, 2003, Acta Sci Pol 2(20), 103-114.
Mantyla et al, 1998,Tricho and Gliocladium 2, 289-310.
Miettinen et al, 2005, J Biotechnol 116(3), 305-317.
Pozo et al, 2004, Fungal Genet Biol 41(3), 336-348.
Sharma et al, 2009, World J Microbiol Biotechnol 25(12), 2083-2094.
Suarez et al, 2007, Curr Genet 51(5), 331-342.
Suarez et al, 2007, EMBL Access No. AM294978.
Yan et al, 2009, FEMS Microbiol Lett 290(1), 54-61.
Martinez et al, 2008, Nature Biotechnology 26:553-560.
Enesyskaya et al., 1999, Appl. Microbiol. Biotechnol. 52: 226-231.
Haab et al., 1990, J. Biotechnology 16: 187-198.
Hagspiel et al., 1989, Appl. Microbiol. Biotechnol. 32: 61-67.

* cited by examiner

*Primary Examiner* — Sheridan Swope
(74) *Attorney, Agent, or Firm* — Robert L. Starnes

(57) ABSTRACT

The present invention relates to mutants of a parent *Trichoderma* strain, comprising a polynucleotide encoding a polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions. The present invention also relates to methods of producing a polypeptide in such mutants and methods for producing such mutants.

23 Claims, 26 Drawing Sheets

SEQUENCE LISTING

```
<160> NUMBER OF SEQ ID NOS: 117

<210> SEQ ID NO 1
<211> LENGTH: 2777
<212> TYPE: DNA
<213> ORGANISM: Trichoderma reesei

<400> SEQUENCE: 1
atggtgcgct ccgccctatt cgtgtcgctg ctcgcgacct tctccggagt cattgcccgt      60
gtctccgggc atgggtcaaa gatcgttccc ggcgcgtaca tcttcgaatt cgaggattca     120
caggtgagtc tcgctcggcc gttggcaccg gatgacatgc ctccagctgt ggcaatgctg     180
acgggactcc atccaggaca cggccgattt ctacaagaag ctcaacggcg agggctcaac     240
gcgcctgaag ttcgactaca agctgttcaa gggcgtctcc gtccagctca aggacctaga     300
caaccatgag gcaaaggccc agcagatggc ccagctgcct gctgtcaaga acgtgtggcc     360
cgtcaccctc atcgacgccc ccaaccccaa ggtcgagtgg gttgccggca gcacggcgcc     420
tactctggag agcagggcga tcaagaagcc accgatcccg aacgactcga gcgacttccc     480
cacgcaccag atgacccaaa tcgacaagct gcgagccaag ggctacacgg gcaagggcgt     540
cagggttgcc gtcattgata caggcgtgag tacaagccca ctgtcccaag caagtcgtgt     600
agacgctcac atacggccag attgactaca cccaccctgc tctcggcggc tgctttggta     660
ggggctgtct ggtctccttt ggcaccgatt tggtcggtga cgactacacc ggctttaaca     720
cgcctgtccc cgatgatgac cccgtcgact gcgccggcca cggttctcac gttgctggta     780
tcattgctgc gcaggagaat ccgtacggct tcactggcgg cgctcccgat gtcaccctcg     840
gcgcttatcg agtctttggc tgcgacggcc aggccggtaa cgatgtcctg atttccgctt     900
acaaccaggc ctttgaggac ggtgcccaga tcatcactgc ctccattggc ggtccctctg     960
gctgggctga ggagccgtgg gccgttgccg tcacccgcat cgttgaggca ggtgttccct    1020
gcacggtctc tgccggcaac gagggcgact ctggtctctt ctttgccagc acggcagcca    1080
atggcaagaa agtcattgct gtcgcctccg tcgacaacga gaacatccct tcagtgctgt    1140
ccgtggcctc ttacaaaatt gacagcggcg ctgcccagga ctttggctac gtctcctcct    1200
ccaaggcgtg ggacggcgtg agcaagcccc tgtatgctgt gtcgttcgac actactattc    1260
ccgacgatgg ctgctcgcct ctccctgaca gcactcccga cctctctgac tacattgtcc    1320
ttgtccgccg tggcacctgc acctttgtcc agaaagccca aaatgtcgct gcaaagggcg    1380
ccaagtacct gctctattat aacaacattc ccggtgcgct ggccgtcgat gtcagcgccg    1440
tccccgagat tgaggctgtc ggcatggtcg atgacaagac gggtgctacc tggattgccg    1500
ccctcaagga tggaaagacc gtcaccctga cactgactga cccgatcgag agcgagaagc    1560
aaattcagtt cagcgacaac ccgacaactg gcggtgctct gagcggctac acaacctggg    1620
gccctacctg ggagctggac gtcaagcctc agatcagctc tccggcggc aacattctct    1680
```

```
ccacgtaccc cgtggctctc ggaggatatg ccaccctgtc cggtacctcc atggcctgcc    1740
ccctgacggc ggctgctgtt gctctgattg acaagctcg tggcacctttt gaccctgcct    1800
tgatcgacaa cttgttggca acgactgcga accccagct gttcaacgac ggcgagaagt    1860
tctacgactt cctcgccccc gttccccaac agggcggtgg cctcatccag gcctacgatg    1920
ccgcctttgc gaccactctc ctgtcaccgt ccagcctgtc gttcaacgac actgaccact    1980
tcatcaagaa gaagcagatc accctcaaga caccagcaa gcagagggtc acctacaagc    2040
tcaaccacgt ccccaccaac accttttaca ctctggcacc cggtaacggc tatccagctc    2100
cctttcctaa cgacgccgtt gccgctcacg ccaatctcaa gtttaatctg cagcaagtga    2160
ccctgcccgc cggcaggtcc atcactgtcg acgtcttccc tactcccccc agggacgtcg    2220
acgccaagcg cctggcgctt tggtcgggct acatcacggt caacggcacg gatggcacca    2280
gtctgtctgt cccgtaccag ggcctcaccg gctccctgca caagcagaag gtgctctatc    2340
cggaggactc ctggatcgcc gattccaccg atgaaagcct ggcccctgtt gagaacggca    2400
ccgtcttcac cattcccgcg ccgggcaacg ctggccccga tgacaagctc ccatcgctcg    2460
tcgtcagccc tgcccttggc tctcgttatg tccgcgttga tctcgtcctc ctgtccgcgc    2520
ctcctcatgg caccaagctc aagacggtca agttcctcga caccacctcc atcggccagc    2580
ctgccggatc accgctcctc tggatcagcc gtggcgccaa ccctattgct tggaccggcg    2640
agctgtctga caacaagttt gctcccctg aacgtacaa ggccgtgttc atgctctgc     2700
gtattttcgg caacgagaag aagaaggagg actgggatgt gagcgaatct cctgccttca    2760
ccatcaagta tgcgtag                                                  2777
```

<210> SEQ ID NO 2
<211> LENGTH: 882
<212> TYPE: PRT
<213> ORGANISM: Trichoderma reesei

<400> SEQUENCE: 2

Met Val Arg Ser Ala Leu Phe Val Ser Leu Leu Ala Thr Phe Ser Gly
1               5                   10                  15

Val Ile Ala Arg Val Ser Gly His Gly Ser Lys Ile Val Pro Gly Ala
            20                  25                  30

Tyr Ile Phe Glu Phe Glu Asp Ser Gln Asp Thr Ala Asp Phe Tyr Lys
        35                  40                  45

Lys Leu Asn Gly Glu Gly Ser Thr Arg Leu Lys Phe Asp Tyr Lys Leu
    50                  55                  60

Phe Lys Gly Val Ser Val Gln Leu Lys Asp Leu Asp Asn His Glu Ala
65                  70                  75                  80

Lys Ala Gln Gln Met Ala Gln Leu Pro Ala Val Lys Asn Val Trp Pro
                85                  90                  95

Val Thr Leu Ile Asp Ala Pro Asn Pro Lys Val Glu Trp Val Ala Gly
            100                 105                 110

Ser Thr Ala Pro Thr Leu Glu Ser Arg Ala Ile Lys Lys Pro Pro Ile
        115                 120                 125

Pro Asn Asp Ser Ser Asp Phe Pro Thr His Gln Met Thr Gln Ile Asp
    130                 135                 140

Lys Leu Arg Ala Lys Gly Tyr Thr Gly Lys Gly Val Arg Val Ala Val
145                 150                 155                 160

Ile Asp Thr Gly Ile Asp Tyr Thr His Pro Ala Leu Gly Gly Cys Phe
                165                 170                 175

```
Gly Arg Gly Cys Leu Val Ser Phe Gly Thr Asp Leu Val Gly Asp Asp
            180                 185                 190

Tyr Thr Gly Phe Asn Thr Pro Val Pro Asp Asp Pro Val Asp Cys
        195                 200                 205

Ala Gly His Gly Ser His Val Ala Gly Ile Ile Ala Ala Gln Glu Asn
            210                 215                 220

Pro Tyr Gly Phe Thr Gly Gly Ala Pro Asp Val Thr Leu Gly Ala Tyr
225                 230                 235                 240

Arg Val Phe Gly Cys Asp Gly Gln Ala Gly Asn Asp Val Leu Ile Ser
                245                 250                 255

Ala Tyr Asn Gln Ala Phe Glu Asp Gly Ala Gln Ile Ile Thr Ala Ser
            260                 265                 270

Ile Gly Gly Pro Ser Gly Trp Ala Glu Glu Pro Trp Ala Val Ala Val
            275                 280                 285

Thr Arg Ile Val Glu Ala Gly Val Pro Cys Thr Val Ser Ala Gly Asn
            290                 295                 300

Glu Gly Asp Ser Gly Leu Phe Phe Ala Ser Thr Ala Ala Asn Gly Lys
305                 310                 315                 320

Lys Val Ile Ala Val Ala Ser Val Asp Asn Glu Asn Ile Pro Ser Val
                325                 330                 335

Leu Ser Val Ala Ser Tyr Lys Ile Asp Ser Gly Ala Ala Gln Asp Phe
            340                 345                 350

Gly Tyr Val Ser Ser Lys Ala Trp Asp Gly Val Ser Lys Pro Leu
            355                 360                 365

Tyr Ala Val Ser Phe Asp Thr Thr Ile Pro Asp Asp Gly Cys Ser Pro
370                 375                 380

Leu Pro Asp Ser Thr Pro Asp Leu Ser Asp Tyr Ile Val Leu Val Arg
385                 390                 395                 400

Arg Gly Thr Cys Thr Phe Val Gln Lys Ala Gln Asn Val Ala Ala Lys
                405                 410                 415

Gly Ala Lys Tyr Leu Leu Tyr Tyr Asn Asn Ile Pro Gly Ala Leu Ala
            420                 425                 430

Val Asp Val Ser Ala Val Pro Glu Ile Glu Ala Val Gly Met Val Asp
            435                 440                 445

Asp Lys Thr Gly Ala Thr Trp Ile Ala Ala Leu Lys Asp Gly Lys Thr
    450                 455                 460

Val Thr Leu Thr Leu Thr Asp Pro Ile Glu Ser Glu Lys Gln Ile Gln
465                 470                 475                 480

Phe Ser Asp Asn Pro Thr Thr Gly Gly Ala Leu Ser Gly Tyr Thr Thr
                485                 490                 495

Trp Gly Pro Thr Trp Glu Leu Asp Val Lys Pro Gln Ile Ser Ser Pro
            500                 505                 510

Gly Gly Asn Ile Leu Ser Thr Tyr Pro Val Ala Leu Gly Gly Tyr Ala
            515                 520                 525

Thr Leu Ser Gly Thr Ser Met Ala Cys Pro Leu Thr Ala Ala Ala Val
    530                 535                 540

Ala Leu Ile Gly Gln Ala Arg Gly Thr Phe Asp Pro Ala Leu Ile Asp
545                 550                 555                 560

Asn Leu Leu Ala Thr Ala Asn Pro Gln Leu Phe Asn Asp Gly Glu
                565                 570                 575

Lys Phe Tyr Asp Phe Leu Ala Pro Val Pro Gln Gln Gly Gly Gly Leu
            580                 585                 590

Ile Gln Ala Tyr Asp Ala Ala Phe Ala Thr Thr Leu Leu Ser Pro Ser
```

|   |   |   | 595 |   |   |   |   | 600 |   |   |   |   | 605 |   |
|---|---|---|---|---|---|---|---|---|---|---|---|---|---|---|

Ser Leu Ser Phe Asn Asp Thr Asp His Phe Ile Lys Lys Lys Gln Ile
　　610　　　　　　　　615　　　　　　　　620

Thr Leu Lys Asn Thr Ser Lys Gln Arg Val Thr Tyr Lys Leu Asn His
625　　　　　　　　630　　　　　　　　635　　　　　　　　640

Val Pro Thr Asn Thr Phe Tyr Thr Leu Ala Pro Gly Asn Gly Tyr Pro
　　　　　　　　645　　　　　　　　650　　　　　　　　655

Ala Pro Phe Pro Asn Asp Ala Val Ala Ala His Ala Asn Leu Lys Phe
　　　　660　　　　　　　　665　　　　　　　　670

Asn Leu Gln Gln Val Thr Leu Pro Ala Gly Arg Ser Ile Thr Val Asp
　　　675　　　　　　　　680　　　　　　　　685

Val Phe Pro Thr Pro Arg Asp Val Asp Ala Lys Arg Leu Ala Leu
　　690　　　　　　　　695　　　　　　　　700

Trp Ser Gly Tyr Ile Thr Val Asn Gly Thr Asp Gly Thr Ser Leu Ser
705　　　　　　　　710　　　　　　　　715　　　　　　　　720

Val Pro Tyr Gln Gly Leu Thr Gly Ser Leu His Lys Gln Lys Val Leu
　　　　　　　　725　　　　　　　　730　　　　　　　　735

Tyr Pro Glu Asp Ser Trp Ile Ala Asp Ser Thr Asp Glu Ser Leu Ala
　　　　　740　　　　　　　　745　　　　　　　　750

Pro Val Glu Asn Gly Thr Val Phe Thr Ile Pro Ala Pro Gly Asn Ala
　　　　755　　　　　　　　760　　　　　　　　765

Gly Pro Asp Asp Lys Leu Pro Ser Leu Val Val Ser Pro Ala Leu Gly
　　770　　　　　　　　775　　　　　　　　780

Ser Arg Tyr Val Arg Val Asp Leu Val Leu Ser Ala Pro Pro His
785　　　　　　　　790　　　　　　　　795　　　　　　　　800

Gly Thr Lys Leu Lys Thr Val Lys Phe Leu Asp Thr Thr Ser Ile Gly
　　　　　　　　805　　　　　　　　810　　　　　　　　815

Gln Pro Ala Gly Ser Pro Leu Leu Trp Ile Ser Arg Gly Ala Asn Pro
　　　　　820　　　　　　　　825　　　　　　　　830

Ile Ala Trp Thr Gly Glu Leu Ser Asp Asn Lys Phe Ala Pro Pro Gly
　　　　835　　　　　　　　840　　　　　　　　845

Thr Tyr Lys Ala Val Phe His Ala Leu Arg Ile Phe Gly Asn Glu Lys
　　850　　　　　　　　855　　　　　　　　860

Lys Lys Glu Asp Trp Asp Val Ser Glu Ser Pro Ala Phe Thr Ile Lys
865　　　　　　　　870　　　　　　　　875　　　　　　　　880

Tyr Ala

<210> SEQ ID NO 3
<211> LENGTH: 1302
<212> TYPE: DNA
<213> ORGANISM: Trichoderma reesei

<400> SEQUENCE: 3

```
atgcagacct tggagctttt tctcgtttcc ttcctcgccg ccagcggcct ggccgcggcc    60
ctccccaccg agggtcagaa gacggcttcc gtcgaggtcc agtacaacaa gaactacgtc   120
ccccacggcc ctactgctct cttcaaggcc aagagaaagt atggcgctcc catcagcgac   180
aacctgaagt ctctcgtggc tgccaggcag gccaagcagg ctctcgccaa gcgccagacc   240
ggctcggcgc ccaaccaccc cagtgacagc gccgattcgg agtacatcac ctccgtctcc   300
atcggcactc cggctcaggt cctccccctg gactttgaca ccggctcctc cgacctgtgg   360
gtctttagct ccgagacgcc caagtcttcg gccaccggcc acgccatcta cacgccctcc   420
aagtcgtcca cctccaagaa ggtgtctggc gccagctggt ccatcagcta cggcgacggc   480
```

-continued

```
agcagctcca gcggcgatgt ctacaccgac aaggtcacca tcggaggctt cagcgtcaac    540
acccagggcg tcgagtctgc cacccgcgtg tccaccgagt tcgtccagga cacggtcatc    600
tctggcctcg tcggccttgc cttttgacagc ggcaaccagg tcaggccgca cccgcagaag    660
acgtggttct ccaacgccgc cagcagcctg gctgagcccc ttttcactgc cgacctgagg    720
cacggacaga gtaagtagac actcactgga attcgttcct ttcccgatca tcatgaaagc    780
aagtagactg actgaaccaa caactagagg ggcagctaca actttggcta catcgacacc    840
agcgtcgcca agggccccgt tgcctacacc cccgttgaca cagccaggg cttctgggag    900
ttcactgcct cgggctactc tgtcggcggc ggcaagctca accgcaactc catcgacggc    960
attgccgaca ccggcaccac cctgctcctc ctcgacgaca acgtcgtcga tgcctactac   1020
gccaacgtcc agtcggccca gtacgacaac cagcaggagg gtgtcgtctt cgactgcgac   1080
gaggacctcc cttcgttcag cttcggtgtt ggaagctcca ccatcaccat ccctggcgat   1140
ctgctgaacc tgactcccct cgaggagggc agctccacct gcttcggtgg cctccagagc   1200
agctccggca ttggcatcaa catctttggt gacgttgccc tcaaggctgc cctggttgtc   1260
tttgacctcg gcaacgagcg cctgggctgg gctcagaaat aa                       1302
```

<210> SEQ ID NO 4
<211> LENGTH: 407
<212> TYPE: PRT
<213> ORGANISM: Trichoderma reesei

<400> SEQUENCE: 4

```
Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
            20                  25                  30

Val Gln Tyr Asn Lys Asn Tyr Val Pro His Gly Pro Thr Ala Leu Phe
        35                  40                  45

Lys Ala Lys Arg Lys Tyr Gly Ala Pro Ile Ser Asp Asn Leu Lys Ser
    50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
                85                  90                  95

Thr Ser Val Ser Ile Gly Thr Pro Ala Gln Val Leu Pro Leu Asp Phe
            100                 105                 110

Asp Thr Gly Ser Ser Asp Leu Trp Val Phe Ser Glu Thr Pro Lys
        115                 120                 125

Ser Ser Ala Thr Gly His Ala Ile Tyr Thr Pro Ser Lys Ser Ser Thr
    130                 135                 140

Ser Lys Lys Val Ser Gly Ala Ser Trp Ser Ile Ser Tyr Gly Asp Gly
145                 150                 155                 160

Ser Ser Ser Ser Gly Asp Val Tyr Thr Asp Lys Val Thr Ile Gly Gly
                165                 170                 175

Phe Ser Val Asn Thr Gln Gly Val Glu Ser Ala Thr Arg Val Ser Thr
            180                 185                 190

Glu Phe Val Gln Asp Thr Val Ile Ser Gly Leu Val Gly Leu Ala Phe
        195                 200                 205

Asp Ser Gly Asn Gln Val Arg Pro His Pro Gln Lys Thr Trp Phe Ser
    210                 215                 220

Asn Ala Ala Ser Ser Leu Ala Glu Pro Leu Phe Thr Ala Asp Leu Arg
```

His Gly Gln Asn Gly Ser Tyr Asn Phe Gly Tyr Ile Asp Thr Ser Val
            225                 230                 235                 240

Ala Lys Gly Pro Val Ala Tyr Thr Pro Val Asp Asn Ser Gln Gly Phe
            245                 250                 255

Trp Glu Phe Thr Ala Ser Gly Tyr Ser Val Gly Gly Lys Leu Asn
        260                 265                 270

Arg Asn Ser Ile Asp Gly Ile Ala Asp Thr Gly Thr Thr Leu Leu Leu
        275                 280                 285

Leu Asp Asp Asn Val Val Asp Ala Tyr Tyr Ala Asn Val Gln Ser Ala
        290                 295                 300

Gln Tyr Asp Asn Gln Gln Glu Gly Val Val Phe Asp Cys Asp Glu Asp
305                 310                 315                 320

Leu Pro Ser Phe Ser Phe Gly Val Gly Ser Ser Thr Ile Thr Ile Pro
                325                 330                 335

Gly Asp Leu Leu Asn Leu Thr Pro Leu Glu Glu Gly Ser Ser Thr Cys
            340                 345                 350

Phe Gly Gly Leu Gln Ser Ser Ser Gly Ile Gly Ile Asn Ile Phe Gly
        355                 360                 365

Asp Val Ala Leu Lys Ala Ala Leu Val Val Phe Asp Leu Gly Asn Glu
    370                 375                 380

Arg Leu Gly Trp Ala Gln Lys
385                 390                 395                 400

405

<210> SEQ ID NO 5
<211> LENGTH: 933
<212> TYPE: DNA
<213> ORGANISM: Trichoderma reesei

<400> SEQUENCE: 5
atggctcccg cttcccaagt cgtctcagct ctcatgctgc ccgctctcgc cttgggagcc      60
gccatccagc ccgtggcgc tgacatcgtg ggaggaaccg ccgcctcgct cggcgagttc     120
ccctacattg tcagtctgca gaaccccaac cagggcggcc acttctgcgg tggtgtcttg     180
gtcaacgcca acaccgtcgt taccgccgct cactgctccg ttgtctaccc tgcctcgcag     240
atccgcgtcc gcgccggtac tcttgtaagt ttgcttgttt cgagtcctcg aaaagacatg     300
aacctgcgat ggctaaccaa agcacctcct ctctgataga cctggaactc tggcggtacc     360
ctggtcggcg tctcccagat catcgtgaac ccgtcctaca cgaccgcac accgactt    t  420
gacgttgccg tctggcacct gtccagccct atccgcgaga gctccaccat ggctacgcc     480
actcttcccg cccagggctc cgaccccgtg gccggctcga ccgtcaccac cgctggctgg     540
taagcatcat catcattgat agccgggaca tgctggcgtc aaatccgagt ttgctaacca     600
ttcttccaaa aaaacagggg caccaccagc gagaactcca actccatccc ctcccgcctg     660
aacaaggtct ccgtccccgt cgtcgcccgc tccacctgcc aggccgacta ccgcagccag     720
gggctcagtg tcaccaacaa catgttctgc gccggcctca cccagggcgg caaggactct     780
tgctctggcg actctggcgg ccccatcgtt gacgccaacg tgtcctcca gggtgtcgtt     840
tcttgggta tcggctgtgc tgaggccggt ttccctggtg tctacaccag aatcggcaac     900
tttgtcaact acatcaacca gaacctcgca taa                                 933

<210> SEQ ID NO 6
<211> LENGTH: 259
<212> TYPE: PRT

<213> ORGANISM: Trichoderma reesei

<400> SEQUENCE: 6

```
Met Ala Pro Ala Ser Gln Val Val Ser Ala Leu Met Leu Pro Ala Leu
1               5                   10                  15

Ala Leu Gly Ala Ala Ile Gln Pro Arg Gly Ala Asp Ile Val Gly Gly
            20                  25                  30

Thr Ala Ala Ser Leu Gly Glu Phe Pro Tyr Ile Val Ser Leu Gln Asn
        35                  40                  45

Pro Asn Gln Gly Gly His Phe Cys Gly Gly Val Leu Val Asn Ala Asn
    50                  55                  60

Thr Val Val Thr Ala Ala His Cys Ser Val Val Tyr Pro Ala Ser Gln
65                  70                  75                  80

Ile Arg Val Arg Ala Gly Thr Leu Thr Trp Asn Ser Gly Thr Leu
                85                  90                  95

Val Gly Val Ser Gln Ile Ile Val Asn Pro Ser Tyr Asn Asp Arg Thr
            100                 105                 110

Thr Asp Phe Asp Val Ala Val Trp His Leu Ser Ser Pro Ile Arg Glu
        115                 120                 125

Ser Ser Thr Ile Gly Tyr Ala Thr Leu Pro Ala Gln Gly Ser Asp Pro
    130                 135                 140

Val Ala Gly Ser Thr Val Thr Thr Ala Gly Trp Gly Thr Thr Ser Glu
145                 150                 155                 160

Asn Ser Asn Ser Ile Pro Ser Arg Leu Asn Lys Val Ser Val Pro Val
                165                 170                 175

Val Ala Arg Ser Thr Cys Gln Ala Asp Tyr Arg Ser Gln Gly Leu Ser
            180                 185                 190

Val Thr Asn Asn Met Phe Cys Ala Gly Leu Thr Gln Gly Gly Lys Asp
        195                 200                 205

Ser Cys Ser Gly Asp Ser Gly Gly Pro Ile Val Asp Ala Asn Gly Val
    210                 215                 220

Leu Gln Gly Val Val Ser Trp Gly Ile Gly Cys Ala Glu Ala Gly Phe
225                 230                 235                 240

Pro Gly Val Tyr Thr Arg Ile Gly Asn Phe Val Asn Tyr Ile Asn Gln
                245                 250                 255

Asn Leu Ala
```

<210> SEQ ID NO 7
<211> LENGTH: 1193
<212> TYPE: DNA
<213> ORGANISM: Neurospora crassa

<400> SEQUENCE: 7

| | | | | |
|---|---|---|---|---|
| atgtcgacaa gtaggaaacg cagccacact ggtccctcaa gcagtcgttt gctgagcggg | | | | 60 |
| tagagagctc gacgcatccc ctcaccagct acctcttccg cctgatggag gtcaagcagt | | | | 120 |
| ccaacctctg cctcagcgcc gatgtcgagc acgcgcggga tctcctcgcc cttgccgaca | | | | 180 |
| aggtgggccc ctcgattgtc gtcctcaaga cccactacga cctgatcaca gggtgggact | | | | 240 |
| accacccgca cacgggcacc ggcgccaagc tggccgccct tgcccggaag cacggcttcc | | | | 300 |
| tcatcttcga ggaccgcaag ttcgtcgaca ttggcagcac cgtccagaag cagtacacgg | | | | 360 |
| ccggcaccgc cgcattgtc gaatgggccc acatccacaa cgccgacatc cacgccggag | | | | 420 |
| aggccatggt gagcgccatg gcccaggccg cgcaaaagtg gagggagcgc atccctacg | | | | 480 |
| aggtcaagac gtcggtttcg gtgggcaccc cggtcgcgga ccagttcgcc gacgaggaag | | | | 540 |

```
ccgaggacca ggttgaggag ctgcgcaagg tcgtcacccg cgagaccagc accaccacaa      600
aggacacgga tgggaggaag agtagcatcg tctccatcac gaccgtcacg cagacatatg      660
agccggccga ctcgccacgt ctggtcaaga ccatctcgga ggacgatgag atggtgttcc      720
ccggcatcga ggaggcgcct ctggaccgcg gcctgctgat cttggcccag atgtcgtcca      780
agggctgcct catggacggc aagtacacat gggagtgtgt caaggcggcc cgcaagaaca      840
agggctttgt catgggctac gttgcgcagc agaacctgaa cggcattacc aaggaagctt      900
tggccccaag ctacgaagac ggcgaaagca cgacagagga agaagcgcaa gcagacaact      960
tcatccacat gacacccggc tgcaagttgc cgccaccagg agaggaagcg cctcagggcg     1020
acggactggg tcagcagtac aacacgccgg ataaccttgt caacatcaag ggcaccgata     1080
tcgcgattgt tgggcgtggc atcatcaccg cggcggatcc tccggccgag ctgagcgct     1140 acaggaggaa agcctggaag gcgtaccagg atcgccggga gcgtctggca tag           1193
```

<210> SEQ ID NO 8
<211> LENGTH: 397
<212> TYPE: PRT
<213> ORGANISM: Neurospora crassa

<400> SEQUENCE: 8

```
Met Ser Thr Ser Gln Glu Thr Gln Pro His Trp Ser Leu Lys Gln Ser
1               5                   10                  15

Phe Ala Glu Arg Val Glu Ser Ser Thr His Pro Leu Thr Ser Tyr Leu
            20                  25                  30

Phe Arg Leu Met Glu Val Lys Gln Ser Asn Leu Cys Leu Ser Ala Asp
        35                  40                  45

Val Glu His Ala Arg Asp Leu Leu Ala Leu Ala Asp Lys Val Gly Pro
    50                  55                  60

Ser Ile Val Val Leu Lys Thr His Tyr Asp Leu Ile Thr Gly Trp Asp
65                  70                  75                  80

Tyr His Pro His Thr Gly Thr Gly Ala Lys Leu Ala Ala Leu Ala Arg
                85                  90                  95

Lys His Gly Phe Leu Ile Phe Glu Asp Arg Lys Phe Val Asp Ile Gly
            100                 105                 110

Ser Thr Val Gln Lys Gln Tyr Thr Ala Gly Thr Ala Arg Ile Val Glu
        115                 120                 125

Trp Ala His Ile Thr Asn Ala Asp Ile His Ala Gly Glu Ala Met Val
    130                 135                 140

Ser Ala Met Ala Gln Ala Ala Gln Lys Trp Arg Glu Arg Ile Pro Tyr
145                 150                 155                 160

Glu Val Lys Thr Ser Val Ser Val Gly Thr Pro Val Ala Asp Gln Phe
                165                 170                 175

Ala Asp Glu Glu Ala Glu Asp Gln Val Glu Glu Leu Arg Lys Val Val
            180                 185                 190

Thr Arg Glu Thr Ser Thr Thr Thr Lys Asp Thr Asp Gly Arg Lys Ser
        195                 200                 205

Ser Ile Val Ser Ile Thr Thr Val Thr Gln Thr Tyr Glu Pro Ala Asp
    210                 215                 220

Ser Pro Arg Leu Val Lys Thr Ile Ser Glu Asp Asp Glu Met Val Phe
225                 230                 235                 240

Pro Gly Ile Glu Glu Ala Pro Leu Asp Arg Gly Leu Leu Ile Leu Ala
                245                 250                 255
```

```
Gln Met Ser Ser Lys Gly Cys Leu Met Asp Gly Lys Tyr Thr Trp Glu
            260                 265                 270

Cys Val Lys Ala Ala Arg Lys Asn Lys Gly Phe Val Met Gly Tyr Val
        275                 280                 285

Ala Gln Gln Asn Leu Asn Gly Ile Thr Lys Glu Ala Leu Ala Pro Ser
    290                 295                 300

Tyr Glu Asp Gly Glu Ser Thr Thr Glu Glu Glu Ala Gln Ala Asp Asn
305                 310                 315                 320

Phe Ile His Met Thr Pro Gly Cys Lys Leu Pro Pro Gly Glu Glu
                325                 330                 335

Ala Pro Gln Gly Asp Gly Leu Gly Gln Gln Tyr Asn Thr Pro Asp Asn
            340                 345                 350

Leu Val Asn Ile Lys Gly Thr Asp Ile Ala Ile Val Gly Arg Gly Ile
        355                 360                 365

Ile Thr Ala Ala Asp Pro Pro Ala Glu Ala Glu Arg Tyr Arg Arg Lys
    370                 375                 380

Ala Trp Lys Ala Tyr Gln Asp Arg Arg Glu Arg Leu Ala
385                 390                 395

<210> SEQ ID NO 9
<211> LENGTH: 20
<212> TYPE: DNA
<213> ORGANISM: Neurospora crassa

<400> SEQUENCE: 9
gtcaggaaac gcagccacac                                                   20

<210> SEQ ID NO 10
<211> LENGTH: 20
<212> TYPE: DNA
<213> ORGANISM: Neurospora crassa

<400> SEQUENCE: 10
aggcagccct tggacgacat                                                   20

<210> SEQ ID NO 11
<211> LENGTH: 1026
<212> TYPE: DNA
<213> ORGANISM: Escherichia coli

<400> SEQUENCE: 11
atgaaaaagc tgaactcac cgcgacgtct gtcgagaagt ttctgatcga aaagttcgac        60
agcgtctccg acctgatgca gctctcggag ggcaagaat ctcgtgcttt cagcttcgat       120
gtaggagggc gtggatatgt cctgcgggta aatagctgcg ccgatggttt ctacaaagat     180
cgttatgttt tcggcactt tgcatcggcc gcgctcccga ttccggaagt gcttgacatt      240
ggggaattca gcgagagcct gacctattgc atctcccgcc gtgcacaggg tgtcacgttg     300
caagacctgc tgaaaccga actgcccgct gttctgcagc cggtcgcgga ggccatggat     360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt ggccgaggga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
```

-continued

```
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg accgatggc     960 tgtgtagaag tactcgccga tagtggaaac cgacgcccca gcactcgtcc gagggcaaag   1020
gaatag                                                             1026
```

<210> SEQ ID NO 12
<211> LENGTH: 343
<212> TYPE: PRT
<213> ORGANISM: Escherichia coli

<400> SEQUENCE: 12

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320
```

```
Cys Val Glu Val Leu Ala Asp Ser Gly Asn Arg Arg Pro Ser Thr Arg
            325                 330                 335

Pro Arg Ala Arg Asn Ser Lys
            340

<210> SEQ ID NO 13
<211> LENGTH: 24
<212> TYPE: DNA
<213> ORGANISM: Escherichia coli

<400> SEQUENCE: 13
gggttcgaat tcatttaaac ggct                                    24

<210> SEQ ID NO 14
<211> LENGTH: 24
<212> TYPE: DNA
<213> ORGANISM: Escherichia coli

<400> SEQUENCE: 14
gggagcgctc aatattcatc tctc                                    24

<210> SEQ ID NO 15
<211> LENGTH: 31
<212> TYPE: DNA
<213> ORGANISM: Escherichia coli

<400> SEQUENCE: 15
gggtacccca agggcgtatt ctgcagatgg g                            31

<210> SEQ ID NO 16
<211> LENGTH: 31
<212> TYPE: DNA
<213> ORGANISM: Escherichia coli

<400> SEQUENCE: 16
cccatctgca gaatacgccc ttggggtacc c                            31

<210> SEQ ID NO 17
<211> LENGTH: 27
<212> TYPE: DNA
<213> ORGANISM: Escherichia coli

<400> SEQUENCE: 17
ggggtacctt catttaaacg gcttcac                                 27

<210> SEQ ID NO 18
<211> LENGTH: 25
<212> TYPE: DNA
<213> ORGANISM: Escherichia coli

<400> SEQUENCE: 18
ggggtacccg accagcagac ggccc                                   25

<210> SEQ ID NO 19
<211> LENGTH: 27
<212> TYPE: DNA
<213> ORGANISM: Aspergillus oryzae

<400> SEQUENCE: 19
ggggtacctc tctggtactc ttcgatc                                 27

<210> SEQ ID NO 20
```

-continued

```
<211> LENGTH: 26
<212> TYPE: DNA
<213> ORGANISM: Aspergillus oryzae

<400> SEQUENCE: 20
tcccccgggc gaccagcaga cggccc                                              26

<210> SEQ ID NO 21
<211> LENGTH: 27
<212> TYPE: DNA
<213> ORGANISM: Aspergillus oryzae

<400> SEQUENCE: 21
ggggtacctc tctggtactc ttcgatc                                             27

<210> SEQ ID NO 22
<211> LENGTH: 26
<212> TYPE: DNA
<213> ORGANISM: Aspergillus oryzae

<400> SEQUENCE: 22
tcccccgggc gaccagcaga cggccc                                              26

<210> SEQ ID NO 23
<211> LENGTH: 31
<212> TYPE: DNA
<213> ORGANISM: Aspergillus oryzae

<400> SEQUENCE: 23
gggtacccca agggcgtatt ctgcagatgg g                                        31

<210> SEQ ID NO 24
<211> LENGTH: 31
<212> TYPE: DNA
<213> ORGANISM: Aspergillus oryzae

<400> SEQUENCE: 24
cccatctgca gaatacgccc ttggggtacc c                                        31

<210> SEQ ID NO 25
<211> LENGTH: 1203
<212> TYPE: DNA
<213> ORGANISM: Fusarium venenatum

<400> SEQUENCE: 25
atggagaact ttcccactga gtattttctc aacacttctg tgcgccttct cgagtacatt          60
cgataccgag atagcaatta tacccgggaa gagcgtatcg agaatttgca ctatgcttac        120
aacaaggctg ctcatcactt tgctcagcca cgacaacagc agctgctcaa ggtagaccct        180
aagcgactac aggcttccct ccaaactatt gttggcatgg tggtatacag ttgggcaaag        240
gtctccaaag agtgtatggc ggatctatct attcattaca cgtacacact cgttttggat        300
gacagcagcg atgatccgta tccagccatg atgaactatt caacgatctc caggctgga         360 cgagaacagg cccacccatg gtgggcgctt gttaatgagc actttcccaa tgtccttcga        420
cattttggtc ccttctgctc attgaacctt atccgcagca ctcttgactg taagtaccct        480
ggctctatta tttcaccgcc ttaataagct aacagtgatg gaattatagt ttttgaggga        540
tgctggatcg agcagtacaa ctttggagga tttccaggat ctcatgacta tcctcagttt        600
cttcgacgca tgaatggctt gggtcactgt gtcgggcttt cttgtgtgcc caaagagcag        660
tttgatgaga gaggtctatt ccttgaaatc acatcagcca ttgctcagat ggagaactgg        720
```

```
atggtctggg tcaatgatct catgtctttc tacaaggagt tcgatgatga gcgtgaccag      780
atcagtctcg tcaagaacta cgtcgtctct gatgagatca ctctccacga agctttagag      840
aagctcaccc aggacactct acactcgtcc aagcagatgg tagctgtctt ctctgacaag      900
gaccctcagg tgatggacac gattgagtgc ttcatgcacg gctatgtcac gtggcacttg      960
tgcgatcaca ggtaccgtct gaatgagatc tacgaaaagg tcaaaggaca aagaccgag      1020 gacgctcaga agttctgcaa gttctatgag caggctgcta acgtcggagc cgtttcgccc     1080
tcggagtggg cttatccacc tattgcgcaa ctggcaaaca ttcggtccaa ggatgtgaag     1140
gatgtgaagg atgtgaagga gattcagaag cctctgctga gctcaattga gctagtggaa     1200
tga                                                                   1203
```

<210> SEQ ID NO 26
<211> LENGTH: 380
<212> TYPE: PRT
<213> ORGANISM: Fusarium venenatum

<400> SEQUENCE: 26

```
Met Glu Asn Phe Pro Thr Glu Tyr Phe Leu Asn Thr Ser Val Arg Leu
1               5                   10                  15

Leu Glu Tyr Ile Arg Tyr Arg Asp Ser Asn Tyr Thr Arg Glu Glu Arg
            20                  25                  30

Ile Glu Asn Leu His Tyr Ala Tyr Asn Lys Ala Ala His Phe Ala
        35                  40                  45

Gln Pro Arg Gln Gln Leu Leu Lys Val Asp Pro Lys Arg Leu Gln
50                  55                  60

Ala Ser Leu Gln Thr Ile Val Gly Met Val Val Tyr Ser Trp Ala Lys
65                  70                  75                  80

Val Ser Lys Glu Cys Met Ala Asp Leu Ser Ile His Tyr Thr Tyr Thr
                85                  90                  95

Leu Val Leu Asp Asp Ser Ser Asp Pro Tyr Pro Ala Met Met Asn
            100                 105                 110

Tyr Phe Asn Asp Leu Gln Ala Gly Arg Glu Gln Ala His Pro Trp Trp
        115                 120                 125

Ala Leu Val Asn Glu His Phe Pro Asn Val Leu Arg His Phe Gly Pro
130                 135                 140

Phe Cys Ser Leu Asn Leu Ile Arg Ser Thr Leu Asp Phe Phe Glu Gly
145                 150                 155                 160

Cys Trp Ile Glu Gln Tyr Asn Phe Gly Gly Phe Pro Gly Ser His Asp
                165                 170                 175

Tyr Pro Gln Phe Leu Arg Arg Met Asn Gly Leu Gly His Cys Val Gly
            180                 185                 190

Ala Ser Leu Trp Pro Lys Glu Gln Phe Asp Glu Arg Gly Leu Phe Leu
        195                 200                 205

Glu Ile Thr Ser Ala Ile Ala Gln Met Glu Asn Trp Met Val Trp Val
    210                 215                 220

Asn Asp Leu Met Ser Phe Tyr Lys Glu Phe Asp Glu Arg Asp Gln
225                 230                 235                 240

Ile Ser Leu Val Lys Asn Tyr Val Val Ser Asp Glu Ile Thr Leu His
                245                 250                 255

Glu Ala Leu Glu Lys Leu Thr Gln Asp Thr Leu His Ser Ser Lys Gln
            260                 265                 270

Met Val Ala Val Phe Ser Asp Lys Asp Pro Gln Val Met Asp Thr Ile
```

```
            275                 280                 285
Glu Cys Phe Met His Gly Tyr Val Thr Trp His Leu Cys Asp His Arg
    290                 295                 300

Tyr Arg Leu Asn Glu Ile Tyr Glu Lys Val Lys Gly Gln Lys Thr Glu
305                 310                 315                 320

Asp Ala Gln Lys Phe Cys Lys Phe Tyr Glu Gln Ala Ala Asn Val Gly
                325                 330                 335

Ala Val Ser Pro Ser Glu Trp Ala Tyr Pro Pro Ile Ala Gln Leu Ala
                340                 345                 350

Asn Ile Arg Ser Lys Asp Val Lys Asp Val Lys Asp Val Lys Glu Ile
                355                 360                 365

Gln Lys Pro Leu Leu Ser Ser Ile Glu Leu Val Glu
                370                 375                 380

<210> SEQ ID NO 27
<211> LENGTH: 23
<212> TYPE: DNA
<213> ORGANISM: Fusarium venenatum

<400> SEQUENCE: 27
gggagatctt cgttatctgt gcc                                            23

<210> SEQ ID NO 28
<211> LENGTH: 29
<212> TYPE: DNA
<213> ORGANISM: Fusarium venenatum

<400> SEQUENCE: 28
gggagatctt agtagtcggc atttgaaac                                      29

<210> SEQ ID NO 29
<211> LENGTH: 43
<212> TYPE: DNA
<213> ORGANISM: Fusarium venenatum

<400> SEQUENCE: 29
caagtaacag acgcgacagc ttgcaaaatc ttcgttatct gtg                      43

<210> SEQ ID NO 30
<211> LENGTH: 43
<212> TYPE: DNA
<213> ORGANISM: Fusarium venenatum

<400> SEQUENCE: 30
cacagataac gaagattttg caagctgtcg cgtctgttac ttg                      43

<210> SEQ ID NO 31
<211> LENGTH: 1131
<212> TYPE: DNA
<213> ORGANISM: Herpes simplex virus

<400> SEQUENCE: 31
atggcttcgt accccggcca tcaacacgcg tctgcgttcg accaggctgc gcgttctcgc    60
ggccatagca accgacgtac ggcgttgcgc cctcgccggc agcaagaagc cacgaaagtc   120
cgcccggagc agaaaatgcc cacgctactg cgggtttata tagacggtcc ccacgggatg   180
gggaaaacca ccaccacgca actgctggtg gccctgggtt cgcgcgacga tatcgtctac   240
gtacccgagc cgatgactta ctggcgggtg ctggggctt ccgagacaat cgcgaacatc   300
tacaccacac aacaccgcct cgaccagggt gagatatcgg ccggggacgc ggcggtggta   360
```

```
atgacaagcg cccagataac aatgggcatg ccttatgccg tgaccgacgc cgttctggct    420
cctcatatcg gggggaggc tgggagctca catgccccgc ccccggccct caccctcatc     480
ttcgaccgcc atcccatcgc cgccctcctg tgctacccgg ccgcgcggta ccttatgggc    540
agcatgaccc ccaggccgt gctggcgttc gtggccctca tcccgccgac cttgcccggc     600
accaacatcg tgcttgggc ccttccggag gacagacaca tcgaccgcct ggccaaacgc     660
cagcgccccg cgagcggct ggacctggct atgctggctg cgattcgccg cgtttacggg    720
ctacttgcca atacggtgcg gtatctgcag tgcggcgggt cgtggcggga ggactgggga   780
cagctttcgg gacggccgt gccgcccag ggtgccgagc ccagagcaa cgcgggccca      840
cgaccccata tcggggacac gttatttacc ctgtttcggg ccccgagtt gctggccccc    900
aacggcgacc tgtataacgt gtttgcctgg gccttggacg tcttggccaa cgcctccgt    960
tccatgcacg tctttatcct ggattacgac caatcgcccg ccggctgccg ggacgccctg   1020
ctgcaactta cctccgggat ggtccagacc cacgtcacca cccccggctc ataccgacg    1080
atatgcgacc tggcgcgcac gtttgcccgg gagatggggg aggctaactg a            1131
```

<210> SEQ ID NO 32
<211> LENGTH: 376
<212> TYPE: PRT
<213> ORGANISM: Herpes simplex virus

<400> SEQUENCE: 32

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240
```

```
Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Gly Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 33
<211> LENGTH: 60
<212> TYPE: DNA
<213> ORGANISM: Aspergillus nidulans

<400> SEQUENCE: 33
gacgaattct ctagaagatc tctcgaggag ctcaagcttc tgtacagtga ccggtgactc     60

<210> SEQ ID NO 34
<211> LENGTH: 27
<212> TYPE: DNA
<213> ORGANISM: Aspergillus nidulans

<400> SEQUENCE: 34
gacgaattcc gatgaatgtg tgtcctg                                         27

<210> SEQ ID NO 35
<211> LENGTH: 40
<212> TYPE: DNA
<213> ORGANISM: Escherichia coli

<400> SEQUENCE: 35
ttgaactctc agatcccttc atttaaacgg cttcacgggc                           40

<210> SEQ ID NO 36
<211> LENGTH: 40
<212> TYPE: DNA
<213> ORGANISM: Escherichia coli

<400> SEQUENCE: 36
cagataacga agatctacgc ccttggggta cccaatattc                           40

<210> SEQ ID NO 37
<211> LENGTH: 40
<212> TYPE: DNA
<213> ORGANISM: Herpes simplex virus

<400> SEQUENCE: 37
gccgactact agatcgaccg gtgactcttt ctggcatgcg                           40
```

-continued

```
<210> SEQ ID NO 38
<211> LENGTH: 40
<212> TYPE: DNA
<213> ORGANISM: Herpes simplex virus

<400> SEQUENCE: 38
cagataacga agatctgaga gttcaaggaa gaaacagtgc                    40

<210> SEQ ID NO 39
<211> LENGTH: 27
<212> TYPE: DNA
<213> ORGANISM: Herpes simplex virus

<400> SEQUENCE: 39
ccctgtttcg gggccccgag ttgctgg                                  27

<210> SEQ ID NO 40
<211> LENGTH: 27
<212> TYPE: DNA
<213> ORGANISM: Herpes simplex virus

<400> SEQUENCE: 40
ccagcaactc ggggccccga aacaggg                                  27

<210> SEQ ID NO 41
<211> LENGTH: 43
<212> TYPE: DNA
<213> ORGANISM: Fusarium venenatum

<400> SEQUENCE: 41
gtttaaacgg cgcgcccgac aaaacaaggc tactgcaggc agg                43

<210> SEQ ID NO 42
<211> LENGTH: 32
<212> TYPE: DNA
<213> ORGANISM: Fusarium venenatum

<400> SEQUENCE: 42
ttgtcgcccg ggaatactcc aactaggcct tg                            32

<210> SEQ ID NO 43
<211> LENGTH: 33
<212> TYPE: DNA
<213> ORGANISM: Fusarium venenatum

<400> SEQUENCE: 43
agtattcccg ggcgacaaaa caaggctact gca                           33

<210> SEQ ID NO 44
<211> LENGTH: 36
<212> TYPE: DNA
<213> ORGANISM: Fusarium venenatum

<400> SEQUENCE: 44
atttaaatcc tgcaggaata ctccaactag gccttg                        36

<210> SEQ ID NO 45
<211> LENGTH: 35
<212> TYPE: DNA
<213> ORGANISM: Escherichia coli

<400> SEQUENCE: 45
aaaacccggg ccttcattta aacggcttca cgggc                         35
```

<210> SEQ ID NO 46
<211> LENGTH: 40
<212> TYPE: DNA
<213> ORGANISM: Escherichia coli

<400> SEQUENCE: 46
aaaacccggg agatctacgc ccttggggta cccaatattc        40

<210> SEQ ID NO 47
<211> LENGTH: 39
<212> TYPE: DNA
<213> ORGANISM: Trichoderma reesei

<400> SEQUENCE: 47
aaaaaacctg cagggatgta agagggtttc ttgaggggt         39

<210> SEQ ID NO 48
<211> LENGTH: 42
<212> TYPE: DNA
<213> ORGANISM: Trichoderma reesei

<400> SEQUENCE: 48
aaaaaacctg cagggcggcc gctgatagta gacatgatac tg     42

<210> SEQ ID NO 49
<211> LENGTH: 42
<212> TYPE: DNA
<213> ORGANISM: Trichoderma reesei

<400> SEQUENCE: 49
aaaaaaggcg cgccgcggcc gcaatggata gctaataatc aa     42

<210> SEQ ID NO 50
<211> LENGTH: 37
<212> TYPE: DNA
<213> ORGANISM: Trichoderma reesei

<400> SEQUENCE: 50
aaaaaaggcg cgccactgtg ggagggctgt atggaca           37

<210> SEQ ID NO 51
<211> LENGTH: 25
<212> TYPE: DNA
<213> ORGANISM: Trichoderma reesei

<400> SEQUENCE: 51
gcggtcattt acagtgcctc gaata                        25

<210> SEQ ID NO 52
<211> LENGTH: 25
<212> TYPE: DNA
<213> ORGANISM: Trichoderma reesei

<400> SEQUENCE: 52
ctgctctgtt agcaatcctc aagca                        25

<210> SEQ ID NO 53
<211> LENGTH: 37
<212> TYPE: DNA
<213> ORGANISM: Aspergillus aculeatus

<400> SEQUENCE: 53
tcttggatcc accatggtcg gactgctttc aatcacc           37

<210> SEQ ID NO 54
<211> LENGTH: 34
<212> TYPE: DNA
<213> ORGANISM: Aspergillus aculeatus

<400> SEQUENCE: 54
ttaactcgag tcacagacac tgcgagtaat agtc                                 34

<210> SEQ ID NO 55
<211> LENGTH: 33
<212> TYPE: DNA
<213> ORGANISM: Aspergillus aculeatus

<400> SEQUENCE: 55
cggactgcgc accatggtcg gactgctttc aat                                  33

<210> SEQ ID NO 56
<211> LENGTH: 35
<212> TYPE: DNA
<213> ORGANISM: Aspergillus aculeatus

<400> SEQUENCE: 56
tcgccacgga gcttatcaca gacactgcga gtaat                                35

<210> SEQ ID NO 57
<211> LENGTH: 27
<212> TYPE: DNA
<213> ORGANISM: Trichoderma reesei

<400> SEQUENCE: 57
acgaatggtc aaaggactat gtatcat                                         27

<210> SEQ ID NO 58
<211> LENGTH: 25
<212> TYPE: DNA
<213> ORGANISM: Trichoderma reesei

<400> SEQUENCE: 58
cacataccca gagtcaggcc ctgcg                                           25

<210> SEQ ID NO 59
<211> LENGTH: 25
<212> TYPE: DNA
<213> ORGANISM: Trichoderma reesei

<400> SEQUENCE: 59
atatctctct cgaggcctgc ttatt                                           25

<210> SEQ ID NO 60
<211> LENGTH: 25
<212> TYPE: DNA
<213> ORGANISM: Trichoderma reesei

<400> SEQUENCE: 60
ctacatcgaa gctgaaagca cgaga                                           25

<210> SEQ ID NO 61
<211> LENGTH: 29
<212> TYPE: DNA
<213> ORGANISM: Trichoderma reesei

<400> SEQUENCE: 61
agtcaggttc agcagatcgc cagggatgg					29

<210> SEQ ID NO 62
<211> LENGTH: 25
<212> TYPE: DNA
<213> ORGANISM: Trichoderma reesei

<400> SEQUENCE: 62
gtggttctcc aacgccgcca gcagc					25

<210> SEQ ID NO 63
<211> LENGTH: 44
<212> TYPE: DNA
<213> ORGANISM: Trichoderma reesei

<400> SEQUENCE: 63
aaaggcgcgc cgcggccgcg aagaagaaga agaacgtgaa agag					44

<210> SEQ ID NO 64
<211> LENGTH: 36
<212> TYPE: DNA
<213> ORGANISM: Trichoderma reesei

<400> SEQUENCE: 64
aaaggcgcgc ccggtcgagc cggccacggg gtcgga					36

<210> SEQ ID NO 65
<211> LENGTH: 39
<212> TYPE: DNA
<213> ORGANISM: Trichoderma reesei

<400> SEQUENCE: 65
aaacctgcag gtcaccaccg ctggctggta agcatcatc					39

<210> SEQ ID NO 66
<211> LENGTH: 43
<212> TYPE: DNA
<213> ORGANISM: Trichoderma reesei

<400> SEQUENCE: 66
aaacctgcag gcggccgcac aaagctagga gtcttgacgt gat					43

<210> SEQ ID NO 67
<211> LENGTH: 25
<212> TYPE: DNA
<213> ORGANISM: Trichoderma reesei

<400> SEQUENCE: 67
gctgtttggc cctcgaaact gccgg					25

<210> SEQ ID NO 68
<211> LENGTH: 25
<212> TYPE: DNA
<213> ORGANISM: Trichoderma reesei

<400> SEQUENCE: 68
ctacatcgaa gctgaaagca cgaga					25

<210> SEQ ID NO 69
<211> LENGTH: 25
<212> TYPE: DNA
<213> ORGANISM: Trichoderma reesei

<400> SEQUENCE: 69

```
caacccaaag atatcgccag atcca                                         25

<210> SEQ ID NO 70
<211> LENGTH: 25
<212> TYPE: DNA
<213> ORGANISM: Trichoderma reesei

<400> SEQUENCE: 70
acgataaact cccccacggc tgaag                                         25

<210> SEQ ID NO 71
<211> LENGTH: 45
<212> TYPE: DNA
<213> ORGANISM: Trichoderma reesei

<400> SEQUENCE: 71
aaaggcgcgc cgcggccgcc catggtgaga agccgggttc gggag                   45

<210> SEQ ID NO 72
<211> LENGTH: 36
<212> TYPE: DNA
<213> ORGANISM: .Trichoderma reesei

<400> SEQUENCE: 72
aaaggcgcgc cagcccttga cagtgatctt gagtcc                             36

<210> SEQ ID NO 73
<211> LENGTH: 36
<212> TYPE: DNA
<213> ORGANISM: Trichoderma reesei

<400> SEQUENCE: 73
aaacctgcag gacaacattg tgcatcggca aacgcc                             36

<210> SEQ ID NO 74
<211> LENGTH: 43
<212> TYPE: DNA
<213> ORGANISM: Trichoderma reesei

<400> SEQUENCE: 74
aaacctgcag gcggccgcaa agtgccgggg gtgccccaag tcg                     43

<210> SEQ ID NO 75
<211> LENGTH: 33
<212> TYPE: DNA
<213> ORGANISM: Trichoderma reesei

<400> SEQUENCE: 75
gccaggtgtc tggcatggct ggcaagctgc gac                                33

<210> SEQ ID NO 76
<211> LENGTH: 25
<212> TYPE: DNA
<213> ORGANISM: Trichoderma reesei

<400> SEQUENCE: 76
ctacatcgaa gctgaaagca cgaga                                         25

<210> SEQ ID NO 77
<211> LENGTH: 20
<212> TYPE: DNA
<213> ORGANISM: Trichoderma reesei
```

```
<400> SEQUENCE: 77
catccactcg gagatgctga                                            20

<210> SEQ ID NO 78
<211> LENGTH: 20
<212> TYPE: DNA
<213> ORGANISM: Trichoderma reesei

<400> SEQUENCE: 78
cggaacttgg tcttttctgt                                            20

<210> SEQ ID NO 79
<211> LENGTH: 28
<212> TYPE: DNA
<213> ORGANISM: Trichoderma reesei

<400> SEQUENCE: 79
acttcggggg atggaagtac ataaactg                                   28

<210> SEQ ID NO 80
<211> LENGTH: 30
<212> TYPE: DNA
<213> ORGANISM: Trichoderma reesei

<400> SEQUENCE: 80
ctcgattcgc cattagatgt tttatacctg                                 30

<210> SEQ ID NO 81
<211> LENGTH: 45
<212> TYPE: DNA
<213> ORGANISM: Trichoderma reesei

<400> SEQUENCE: 81
aaaggcgcgc cgcggccgca aaacacacac aataaccaac cccca                45

<210> SEQ ID NO 82
<211> LENGTH: 40
<212> TYPE: DNA
<213> ORGANISM: Trichoderma reesei

<400> SEQUENCE: 82
aaaggcgcgc ctgcgatgga ggaaaagctg cgagggatga                      40

<210> SEQ ID NO 83
<211> LENGTH: 36
<212> TYPE: DNA
<213> ORGANISM: Trichoderma reesei

<400> SEQUENCE: 83
aaacctgcag ggcgattccc tgtgttggca accaaa                          36

<210> SEQ ID NO 84
<211> LENGTH: 43
<212> TYPE: DNA
<213> ORGANISM: Trichoderma reesei

<400> SEQUENCE: 84
aaacctgcag gcggccgcaa gaaatactca ggaaaggtgc cca                  43

<210> SEQ ID NO 85
<211> LENGTH: 20
<212> TYPE: DNA
<213> ORGANISM: Trichoderma reesei
```

<400> SEQUENCE: 85
cttctctttc tggcattgac                                                   20

<210> SEQ ID NO 86
<211> LENGTH: 20
<212> TYPE: DNA
<213> ORGANISM: Trichoderma reesei

<400> SEQUENCE: 86
ctcggaatcc tgcggttgcc                                                   20

<210> SEQ ID NO 87
<211> LENGTH: 25
<212> TYPE: DNA
<213> ORGANISM: Trichoderma reesei

<400> SEQUENCE: 87
ggcgcctcaa tccagaaggt cgcac                                             25

<210> SEQ ID NO 88
<211> LENGTH: 26
<212> TYPE: DNA
<213> ORGANISM: Trichoderma reesei

<400> SEQUENCE: 88
gtgtatgtag tgaaacgaag cattcg                                            26

<210> SEQ ID NO 89
<211> LENGTH: 44
<212> TYPE: DNA
<213> ORGANISM: Trichoderma reesei

<400> SEQUENCE: 89
aaaggcgcgc cgcggccgct cgctgtaacg aacttctgtc cgca                        44

<210> SEQ ID NO 90
<211> LENGTH: 39
<212> TYPE: DNA
<213> ORGANISM: Trichoderma reesei

<400> SEQUENCE: 90
aaaggcgcgc ccttgaatat cggagaaggt tgctcacgg                              39

<210> SEQ ID NO 91
<211> LENGTH: 36
<212> TYPE: DNA
<213> ORGANISM: Trichoderma reesei

<400> SEQUENCE: 91
aaacctgcag ggcggcgatg gtggacttgt ttatga                                 36

<210> SEQ ID NO 92
<211> LENGTH: 43
<212> TYPE: DNA
<213> ORGANISM: Trichoderma reesei

<400> SEQUENCE: 92
aaacctgcag gcggccgcag caagtgagta tcgagtttgt agg                         43

<210> SEQ ID NO 93
<211> LENGTH: 33
<212> TYPE: DNA

```
<213> ORGANISM: Trichoderma reesei

<400> SEQUENCE: 93
tcggggagga tggcgcaaac cgaccttcct aaa                           33

<210> SEQ ID NO 94
<211> LENGTH: 25
<212> TYPE: DNA
<213> ORGANISM: Trichoderma reesei

<400> SEQUENCE: 94
gcaccttacc cctacggacc acgat                                    25

<210> SEQ ID NO 95
<211> LENGTH: 31
<212> TYPE: DNA
<213> ORGANISM: Trichoderma reesei

<400> SEQUENCE: 95
cttctatctt gggatgcttc acgatacgtg a                             31

<210> SEQ ID NO 96
<211> LENGTH: 25
<212> TYPE: DNA
<213> ORGANISM: Trichoderma reesei

<400> SEQUENCE: 96
cgcgcccttg aatatcggag aaggt                                    25

<210> SEQ ID NO 97
<211> LENGTH: 47
<212> TYPE: DNA
<213> ORGANISM: Aspergillus aculeatus

<400> SEQUENCE: 97
acacaactgg ggatccacca tggctgtggc ggctcttgct ctgctgg            47

<210> SEQ ID NO 98
<211> LENGTH: 45
<212> TYPE: DNA
<213> ORGANISM: Aspergillus aculeatus

<400> SEQUENCE: 98
agatctcgag aagcttactc atcccccgcc accccctgca cctcc              45

<210> SEQ ID NO 99
<211> LENGTH: 1684
<212> TYPE: DNA
<213> ORGANISM: Trichoderma reesei

<400> SEQUENCE: 99
atgcggtccg ttgtcgccct ctccatggcg gccgttgccc aggccagcac attccagatt   60
ggcaccatcc acgagaagtc gggccccgtg ctgagcaacg tcgaggccaa cgccatcccc  120
gatgcctaca tcatcaagtt caaggaccac gtgggtgagg atgatgcctc caagcaccac  180
gactggatcc agagcatcca cacaaacgtt gagcaggagc gccttgagct ccgcaagcga  240
agcaacgtct ttggcgccga cgacgtcttt gacggtctga gcacactttt caagattggc  300
gacggcttca agggctacgc cggtcacttc cacgagtctg tcattgagca ggtccggaac  360
caccctgacg taagttttgc acagccgccc tcccttttgg ctcccaaaca agctaaccc   420 ctcccaggtt gagtacatcg agcgcgacag cattgtgcac accatgcttc ccctcgagtc  480
```

```
caaggacagc atcatcgttg aggactcgtg caacggcgag acggagaagc aggctccctg    540
gggtcttgcc cgtatctctc accgagagac gctcaacttt ggctccttca acaagtacct    600
ctacaccgct gatggtggtg agggtgttga tgcctatgtc attgacaccg gcaccaacat    660
cgagcacgtc gactttgagg tcgtgccaa gtggggcaag accatccctg ccggcgatga    720
ggacgaggac ggcaacggcc acggcactca ctgctctggt accgttgctg gtaagaagta    780
cggtgttgca aagaaggccc acgtctacgc cgtcaaggtg ctccgatcca acggatccgg    840
caccatgtct gacgtcgtca agggcgtcga gtacgctgct ctctcccaca ttgagcaggt    900
gaagaaggcc aagaagggca gcggaaggg cttcaagggc tccgtcgcca acatgtccct    960
cggtggtggc aagacccagg ctcttgacgc tgccgtcaac gccgccgtcc gcgccggtgt   1020
ccactttgcc gttgctgccg gcaacgacaa cgctgatgct tgcaactact cccccgctgc   1080
cgccactgag cccctcaccg tcggtgcttc tgctctcgat gacagccgtg cttacttctc   1140
caactacggc aagtgcactg acatcttcgc ccctggtctg agcatccagt ccacctggat   1200
tggctccaag tatgccgtca caccatctc tggtacctcc atggcctctc ctcacatctg   1260
cggtctcctg gcctactacc tgtctctcca gcccgctggt gactctgagt cgctgttgc   1320
ccccatcacc cccaagaagc tcaaggagag cgtcatctct gtcgccacca gaacgccct   1380
ctctgacctg cccgactctg acaccccaa cctgctcgcc tggaacggcg gtggctgcag   1440
caacttctcc cagattgtcg aggccggcag ctacactgtc aagcccaagc agaacaagca   1500
ggccaagctc cccagcacca ttgaggagct cgaggaggcc atcgagggtg actttgaggt   1560
cgtctctggc gagatcgtca agggtgccaa gagctttggc tccaaggcgg agaagtttgc   1620
caagaagatc cacgatctcg tcgaggagga gattgaggag ttcatctctg agctctccga   1680
gtaa                                                                 1684
```

<210> SEQ ID NO 100
<211> LENGTH: 540
<212> TYPE: PRT
<213> ORGANISM: Trichoderma reesei

<400> SEQUENCE: 100

```
Met Arg Ser Val Val Ala Leu Ser Met Ala Ala Val Ala Gln Ala Ser
1               5                   10                  15

Thr Phe Gln Ile Gly Thr Ile His Glu Lys Ser Ala Pro Val Leu Ser
            20                  25                  30

Asn Val Glu Ala Asn Ala Ile Pro Asp Ala Tyr Ile Ile Lys Phe Lys
        35                  40                  45

Asp His Val Gly Glu Asp Asp Ala Ser Lys His His Asp Trp Ile Gln
    50                  55                  60

Ser Ile His Thr Asn Val Glu Gln Glu Arg Leu Glu Leu Arg Lys Arg
65                  70                  75                  80

Ser Asn Val Phe Gly Ala Asp Asp Val Phe Asp Gly Leu Lys His Thr
                85                  90                  95

Phe Lys Ile Gly Asp Gly Phe Lys Gly Tyr Ala Gly His Phe His Glu
            100                 105                 110

Ser Val Ile Glu Gln Val Arg Asn His Pro Val Glu Tyr Ile Glu Arg
        115                 120                 125

Asp Ser Ile Val His Thr Met Leu Pro Leu Glu Ser Lys Asp Ser Ile
    130                 135                 140

Ile Val Glu Asp Ser Cys Asn Gly Glu Thr Glu Lys Gln Ala Pro Trp
```

```
                145                 150                 155                 160
Gly Leu Ala Arg Ile Ser His Arg Glu Thr Leu Asn Phe Gly Ser Phe
                165                 170                 175

Asn Lys Tyr Leu Tyr Thr Ala Asp Gly Gly Glu Gly Val Asp Ala Tyr
                180                 185                 190

Val Ile Asp Thr Gly Thr Asn Ile Glu His Val Asp Phe Glu Gly Arg
            195                 200                 205

Ala Lys Trp Gly Lys Thr Ile Pro Ala Gly Asp Glu Asp Glu Asp Gly
210                 215                 220

Asn Gly His Gly Thr His Cys Ser Gly Thr Val Ala Gly Lys Lys Tyr
225                 230                 235                 240

Gly Val Ala Lys Lys Ala His Val Tyr Ala Val Lys Val Leu Arg Ser
                245                 250                 255

Asn Gly Ser Gly Thr Met Ser Asp Val Val Lys Gly Val Glu Tyr Ala
            260                 265                 270

Ala Leu Ser His Ile Glu Gln Val Lys Lys Ala Lys Lys Gly Lys Arg
        275                 280                 285

Lys Gly Phe Lys Gly Ser Val Ala Asn Met Ser Leu Gly Gly Gly Lys
    290                 295                 300

Thr Gln Ala Leu Asp Ala Ala Val Asn Ala Ala Val Arg Ala Gly Val
305                 310                 315                 320

His Phe Ala Val Ala Ala Gly Asn Asp Asn Ala Asp Ala Cys Asn Tyr
                325                 330                 335

Ser Pro Ala Ala Ala Thr Glu Pro Leu Thr Val Gly Ala Ser Ala Leu
            340                 345                 350

Asp Asp Ser Arg Ala Tyr Phe Ser Asn Tyr Gly Lys Cys Thr Asp Ile
        355                 360                 365

Phe Ala Pro Gly Leu Ser Ile Gln Ser Thr Trp Ile Gly Ser Lys Tyr
    370                 375                 380

Ala Val Asn Thr Ile Ser Gly Thr Ser Met Ala Ser Pro His Ile Cys
385                 390                 395                 400

Gly Leu Leu Ala Tyr Tyr Leu Ser Leu Gln Pro Ala Gly Asp Ser Glu
                405                 410                 415

Phe Ala Val Ala Pro Ile Thr Pro Lys Lys Leu Lys Glu Ser Val Ile
            420                 425                 430

Ser Val Ala Thr Lys Asn Ala Leu Ser Asp Leu Pro Asp Ser Asp Thr
        435                 440                 445

Pro Asn Leu Leu Ala Trp Asn Gly Gly Cys Ser Asn Phe Ser Gln
    450                 455                 460

Ile Val Glu Ala Gly Ser Tyr Thr Val Lys Pro Lys Gln Asn Lys Gln
465                 470                 475                 480

Ala Lys Leu Pro Ser Thr Ile Glu Glu Leu Glu Ala Ile Glu Gly
                485                 490                 495

Asp Phe Glu Val Val Ser Gly Ile Val Lys Gly Ala Lys Ser Phe
            500                 505                 510

Gly Ser Lys Ala Glu Lys Phe Ala Lys Lys Ile His Asp Leu Val Glu
        515                 520                 525

Glu Glu Ile Glu Glu Phe Ile Ser Glu Leu Ser Glu
    530                 535                 540

<210> SEQ ID NO 101
<211> LENGTH: 47
<212> TYPE: DNA
<213> ORGANISM: Trichoderma reesei
```

```
<400> SEQUENCE: 101
tcacatggtt taaacggcgc gccggtacta tattagaaag gggttcc              47

<210> SEQ ID NO 102
<211> LENGTH: 47
<212> TYPE: DNA
<213> ORGANISM: Trichoderma reesei

<400> SEQUENCE: 102
agccttgttt tgtcgggcgc gccgaagaag agaagaggag gaggatg              47

<210> SEQ ID NO 103
<211> LENGTH: 47
<212> TYPE: DNA
<213> ORGANISM: Trichoderma reesei

<400> SEQUENCE: 103
cctagttgga gtattcctgc aggtctatct cttttgagta gtcccca              47

<210> SEQ ID NO 104
<211> LENGTH: 55
<212> TYPE: DNA
<213> ORGANISM: Trichoderma reesei

<400> SEQUENCE: 104
tggccatatt taaatcctgc agggtttaaa cagctagtga ctcgcgattt atcgt     55

<210> SEQ ID NO 105
<211> LENGTH: 25
<212> TYPE: DNA
<213> ORGANISM: Trichoderma reesei

<400> SEQUENCE: 105
tgatttcgtg gacagcgttt ctcgc                                      25

<210> SEQ ID NO 106
<211> LENGTH: 28
<212> TYPE: DNA
<213> ORGANISM: Trichoderma reesei

<400> SEQUENCE: 106
ttgccttaca gctggcaaca atggcgtc                                   28

<210> SEQ ID NO 107
<211> LENGTH: 1341
<212> TYPE: DNA
<213> ORGANISM: Trichoderma reesei

<400> SEQUENCE: 107
atgaagagcg cgttacttgc cgccgcggcg cttgtcggct ccgcccaagc cggcattcac   60
aagatgaagc tgcagaaggt ctccctggag cagcagctgg taagacgaca ccctcatcca  120
cggcctcgta ctctagccaa gcgcaatcac tgacacgccg cctctctcat ctaggagggt  180
tcgagcatcg aggcccacgt ccagcagctc ggccagaagt acatgggcgt ccgcccctact 240 agccgtgccg aggtcatgtt caacgacaag ccgcccaagg tccagggcgg gcacccggtt  300
cccgtcacca acttcatgaa tgcccaatgt aagtcgtgat gcgcagcaca gcacgagagt  360
cccgctccca ggtagcgagc acatgcttac taacttgctc ggacagactt ctctgagatt  420
accatcggca ccccccctca gtcgttcaag gttgtcctcg acacgggaag ctctaacctc  480
```

```
tgggttccct ctcagtcgtg caacagcatc gcctgcttcc tgcactccac gtacgattcg    540
tcttcatcgt cgacgtacaa gcccaacggc tccgattttg agatccacta cggatcaggt    600
agcttgactg gcttcatctc caacgatgtc gtgacgattg gcgacctcaa gatcaagggg    660
caggactttg ccgaggcaac cagcgagccc ggccttgcct ttgctttcgg ccgcttcgac    720
ggcattcttg gccttggcta cgataccatc tcggtcaatg gcattgtccc cccttttac     780 cagatggtca accagaagct gatcgacgag cccgtctttg ctttctacct gggaagcagc    840
gacgagggtt ccgaggctgt ctttggcggc gtcgacgatg ctcactacga gggcaagatt    900
gagtacattc ccctgcgccg caaggcctac tgggaggtgg accttgactc cattgccttc    960
ggtgacgagg tcgccgagct cgagaacact ggcgccatcc ttgacaccgg cacctctctc   1020
aacgtcctcc cctcgggcct cgccgagctc ctgaacgctg agattggcgc caagaagggc   1080
tttggcggtc agtacactgt tgactgctcc aagcgtgatt ccctccccga catcaccttc   1140
agcctggccg gctccaagta cagccttccc gccagcgact acatcattga gatgtctggc   1200
aactgcattt cgtccttcca gggcatggac ttccccgagc ccgtgggccc cctggtcatt   1260
ctgggtgatg ctttcttgcg ccgctactac tccgtctacg accttggcag ggacgccgtt   1320
ggtcttgcca aggccaaata a                                             1341

<210> SEQ ID NO 108
<211> LENGTH: 395
<212> TYPE: PRT
<213> ORGANISM: Trichoderma reesei

<400> SEQUENCE: 108

Met Lys Ser Ala Leu Ala Ala Ala Ala Leu Val Gly Ser Ala Gln
1               5                   10                  15

Ala Gly Ile His Lys Met Lys Leu Gln Lys Val Ser Leu Glu Gln Gln
            20                  25                  30

Leu Glu Gly Ser Ser Ile Glu Ala His Val Gln Gln Leu Gly Gln Lys
        35                  40                  45

Tyr Met Gly Val Arg Pro Thr Ser Arg Ala Glu Val Met Phe Asn Asp
    50                  55                  60

Lys Pro Pro Lys Val Gln Gly Gly His Pro Val Pro Val Thr Asn Phe
65                  70                  75                  80

Met Asn Ala Gln Tyr Phe Ser Glu Ile Thr Ile Gly Thr Pro Pro Gln
                85                  90                  95

Ser Phe Lys Val Val Leu Asp Thr Gly Ser Ser Asn Leu Trp Val Pro
            100                 105                 110

Ser Gln Ser Cys Asn Ser Ile Ala Cys Phe Leu His Ser Thr Tyr Asp
        115                 120                 125

Ser Ser Ser Ser Thr Tyr Lys Pro Asn Gly Ser Asp Phe Glu Ile
    130                 135                 140

His Tyr Gly Ser Gly Ser Leu Thr Gly Phe Ile Ser Asn Asp Val Val
145                 150                 155                 160

Thr Ile Gly Asp Leu Lys Ile Lys Gly Gln Asp Phe Ala Glu Ala Thr
                165                 170                 175

Ser Glu Pro Gly Leu Ala Phe Ala Phe Gly Arg Phe Asp Gly Ile Leu
            180                 185                 190

Gly Leu Gly Tyr Asp Thr Ile Ser Val Asn Gly Ile Val Pro Pro Phe
        195                 200                 205

Tyr Gln Met Val Asn Gln Lys Leu Ile Asp Glu Pro Val Phe Ala Phe
    210                 215                 220
```

```
Tyr Leu Gly Ser Ser Asp Glu Gly Ser Glu Ala Val Phe Gly Gly Val
225                 230                 235                 240

Asp Asp Ala His Tyr Glu Gly Lys Ile Glu Tyr Ile Pro Leu Arg Arg
            245                 250                 255

Lys Ala Tyr Trp Glu Val Asp Leu Asp Ser Ile Ala Phe Gly Asp Glu
        260                 265                 270

Val Ala Glu Leu Glu Asn Thr Gly Ala Ile Leu Asp Thr Gly Thr Ser
    275                 280                 285

Leu Asn Val Leu Pro Ser Gly Leu Ala Glu Leu Leu Asn Ala Glu Ile
290                 295                 300

Gly Ala Lys Lys Gly Phe Gly Gln Tyr Thr Val Asp Cys Ser Lys
305                 310                 315                 320

Arg Asp Ser Leu Pro Asp Ile Thr Phe Ser Leu Ala Gly Ser Lys Tyr
                325                 330                 335

Ser Leu Pro Ala Ser Asp Tyr Ile Ile Glu Met Ser Gly Asn Cys Ile
            340                 345                 350

Ser Ser Phe Gln Gly Met Asp Phe Pro Glu Pro Val Gly Pro Leu Val
        355                 360                 365

Ile Leu Gly Asp Ala Phe Leu Arg Arg Tyr Tyr Ser Val Tyr Asp Leu
    370                 375                 380

Gly Arg Asp Ala Val Gly Leu Ala Lys Ala Lys
385                 390                 395

<210> SEQ ID NO 109
<211> LENGTH: 48
<212> TYPE: DNA
<213> ORGANISM: Trichoderma reesei

<400> SEQUENCE: 109
tcacatggtt taaacggcgc gccttccggc ttcttttat gtatacct            48

<210> SEQ ID NO 110
<211> LENGTH: 47
<212> TYPE: DNA
<213> ORGANISM: Trichoderma reesei

<400> SEQUENCE: 110
agccttgttt tgtcgggcgc gccaagctag gaaccagcct ctttgta            47

<210> SEQ ID NO 111
<211> LENGTH: 47
<212> TYPE: DNA
<213> ORGANISM: Trichoderma reesei

<400> SEQUENCE: 111
ctagttggag tattcctgca ggagccgagc tcctgaacgc tgagatt            47

<210> SEQ ID NO 112
<211> LENGTH: 54
<212> TYPE: DNA
<213> ORGANISM: Trichoderma reesei

<400> SEQUENCE: 112
tggccatatt taaatcctgc aggtttaaac gagggaaaag ggccgctgca cgat    54

<210> SEQ ID NO 113
<211> LENGTH: 24
<212> TYPE: DNA
<213> ORGANISM: Trichoderma reesei
```

```
<400> SEQUENCE: 113
cgcggaggtg aggtgttgat gatg                                              24

<210> SEQ ID NO 114
<211> LENGTH: 24
<212> TYPE: DNA
<213> ORGANISM: Trichoderma reesei

<400> SEQUENCE: 114
cggcggtctt taaggtgatg tcgc                                              24

<210> SEQ ID NO 115
<211> LENGTH: 22
<212> TYPE: DNA
<213> ORGANISM: Trichoderma reesei

<400> SEQUENCE: 115
gtttcaggca ggtcttgcaa cg                                                22

<210> SEQ ID NO 116
<211> LENGTH: 24
<212> TYPE: DNA
<213> ORGANISM: Trichoderma reesei

<400> SEQUENCE: 116
gaagacagtc ctactgctgc ggag                                              24

<210> SEQ ID NO 117
<211> LENGTH: 24
<212> TYPE: DNA
<213> ORGANISM: Trichoderma reesei

<400> SEQUENCE: 117
gtagctctcc ccgtataatg cagg                                              24
```

METHODS FOR PRODUCING POLYPEPTIDIES IN PROTEASE-DEFICIENT MUTANTS OF TRICHODERMA

CROSS-REFERENCE TO RELATED APPLICATIONS

This application is a 35 U.S.C. 371 national application of PCT/US2010/061105 filed on Dec. 17, 2010 and claims priority from U.S. Provisional Application Ser. No. 61/287,844 filed on Dec. 18, 2009, now abandoned, which applications are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to methods of producing polypeptides in protease-deficient *Trichoderma* mutant strains, the protease-deficient *Trichoderma* mutant strains, and methods of obtaining the protease-deficient *Trichoderma* mutant strains.

2. Description of the Related Art

*Trichoderma* has been shown to be useful as a host cell for the recombinant production of polypeptides having biological activity (WO 96/00787, WO 97/26330). *Trichoderma* hosts with the desirable traits of increased protein expression and secretion may not necessarily have the most desirable characteristics for successful fermentation. The fermentation may not be optimal because of the production of biological substances, e.g., enzymes, detrimental to the production, recovery, or application of a particular polypeptide of interest.

Martinez et al., 2008, *Nature Biotechnology* 26:553-560, describe the genome sequencing and analysis of the biomass-degrading fungus *Trichoderma reesei*. Dienes et al., 2007, *Enzyme and Microbial Technology* 40: 1087-1094, disclose the identification of a trypsin-like serine protease from *Trichoderma reesei* QM9414. Eneyskaya et al., 1999, *Appl. Microbiol. Biotechnol.* 52: 226-231, describe an acid protease from *Trichoderma reesei*. Haub et al., 1990, *J. Biotechnology* 16: 187-198, disclose the formation of extracellular proteases from *Trichoderma reesei* QM9414. Hagspiel et al., 1989, *Appl. Microbiol. Biotechnol.* 32: 61-67, disclose protease activity and proteolytic modification of cellulases from a *Trichoderma reesei* QM9414 selectant. WO 2006/073839 discloses fungal acidic proteases.

WO 2007/045248 describes use of fungal mutants for expression of heterologous polypeptides.

The present invention relates to improved *Trichoderma* hosts that combine the capacity for expression of commercial quantities of a polypeptide of interest while being deficient in the production of preotease(s) that can complicate recovery and downstream processing of the polypeptide.

SUMMARY OF THE INVENTION

The present invention relates to mutants of a parent *Trichoderma* strain, comprising a polynucleotide encoding a polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions.

The present invention also relates to methods of producing a polypeptide, comprising:

(a) cultivating a mutant of a parent *Trichoderma* strain in a medium for the production of the polypeptide, wherein the mutant strain comprises a polynucleotide encoding the polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions; and (b) recovering the polypeptide from the cultivation medium.

The present invention further relates to methods of obtaining mutants of a parent *Trichoderma* strain, comprising:

(a) modifying one or more (several) genes selected from the group consisting of a first subtilisin-like serine protease gene, a first aspartic protease gene, a trypsin-like serine protease gene, a second subtilisin-like serine protease gene, and a second aspartic protease gene; and (b) identifying a mutant strain from step (a) wherein the one or more (several) genes selected from the group consisting of a first subtilisin-like serine protease gene, a first aspartic protease gene, a trypsin-like serine protease gene, a second subtilisin-like serine protease gene, and a second aspartic protease gene are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions.

DEFINITIONS

Figure 1:
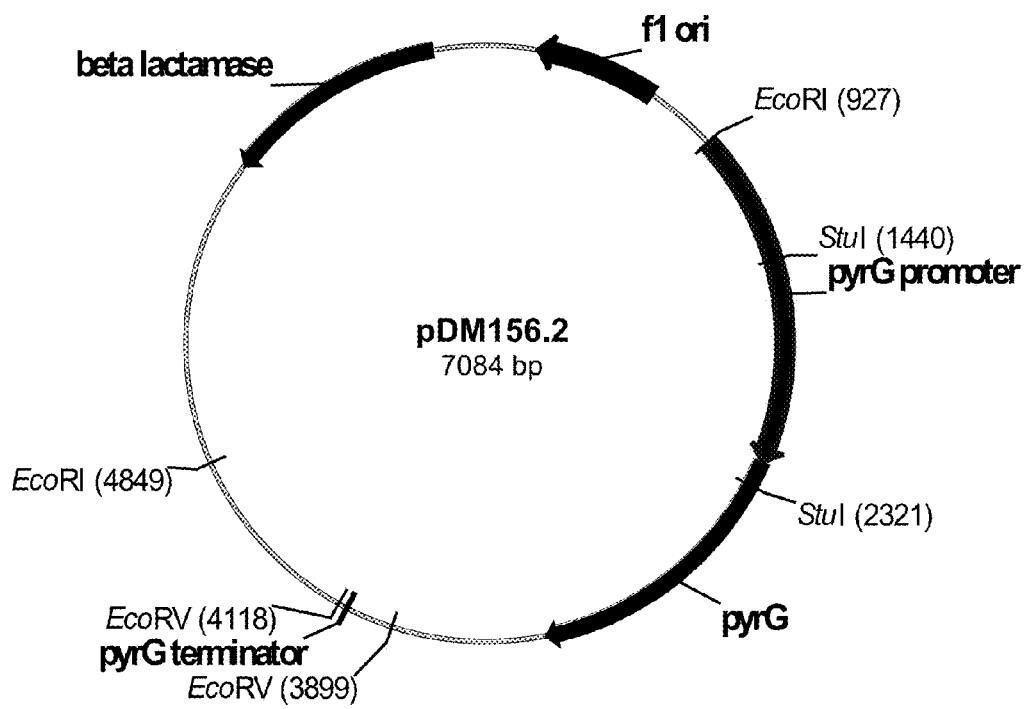
FIG. 1 shows a restriction map of pDM156.2.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). For purposes of the present invention, subtilisin-like serine protease activity is determined according to the procedure described in Example 13.

Aspartic protease: The term "aspartic protease" means a protease that uses an aspartate residue(s) for catalyzing the hydrolysis of peptide bonds in peptides and proteins. Aspartic proteases are a family of protease enzymes that use an aspartate residue for catalysis of their peptide substrates. In general, they have two highly-conserved aspartates in the active site and are optimally active at acidic pH (Szecsi, 1992, *Scand. J. Clin. Lab. Invest. Suppl.* 210: 5-22). For purposes of the present invention, aspartic protease activity is determined according to the procedure described by Aikawa et al., 2001, *J. Biochem.* 129: 791-794.

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by Dienes et al., 2007, supra, or Example 20.

Deficient: The term "deficient" means a *Trichoderma* mutant strain that produces no detectable activity of one or more (several) enzymes selected from the group consisting of a first subtilisin-like serine protease, a first aspartic protease, a trypsin-like serine protease, and a second aspartic protease compared to the parent *Trichoderma* strain when cultivated under identical conditions, or, in the alternative, produces preferably at least 25% less, more preferably at least 50% less, even more preferably at least 75% less, and most preferably at least 95% less of one or more (several) enzymes selected from the group consisting of a first subtilisin-like serine protease, a first aspartic protease, a trypsin-like serine protease, a second subtilisin-like serine protease, and a second aspartic protease than the parent *Trichoderma* strain when cultivated under identical conditions. The level of protease produced by a *Trichoderma* mutant strain of the present invention may be determined using methods described herein or known in the art.

Isolated or Purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 882 of SEQ ID NO: 2 based on the SignalP program (Nielsen et al., 1997, *Protein Engineering* 10: 1-6) that predicts amino acids 1 to 19 of SEQ ID NO: 2 are a signal peptide. In another aspect, the mature polypeptide is amino acids 21 to 407 of SEQ ID NO: 4 based on the SignalP program that predicts amino acids 1 to 20 of SEQ ID NO: 4 are a signal peptide. In another aspect, the mature polypeptide is amino acids 20 to 259 of SEQ ID NO: 6 based on the SignalP program that predicts amino acids 1 to 19 of SEQ ID NO: 6 are a signal peptide. In another aspect, the mature polypeptide is amino acids 16 to 540 of SEQ ID NO: 100 based on the SignalP program that predicts amino acids 1 to 15 of SEQ ID NO: 100 are a signal peptide. [In another aspect, the mature polypeptide is amino acids 18 to 395 of SEQ ID NO: 108 based on the SignalP program that predicts amino acids 1 to 17 of SEQ ID NO: 108 are a signal peptide.

Mature polypeptide coding sequence: The term "mature polypeptide coding sequence" means a polynucleotide that encodes a mature polypeptide having enzyme activity. In one aspect, the mature polypeptide coding sequence is nucleotides 58 to 2774 of SEQ ID NO: 1 based on the SignalP program (Nielsen et al., 1997, supra) that predicts nucleotides 1 to 57 of SEQ ID NO: 3 encode a signal peptide. In another aspect, the mature polypeptide coding sequence is nucleotides 61 to 1299 of SEQ ID NO: 3 based on the SignalP program that predicts nucleotides 1 to 60 of SEQ ID NO: 1 encode a signal peptide. In another aspect, the mature polypeptide coding sequence is nucleotides 58 to 930 of SEQ ID NO: 5 based on the SignalP program that predicts nucleotides 1 to 57 of SEQ ID NO: 5 encode a signal peptide. In another aspect, the mature polypeptide coding sequence is nucleotides 46 to 1681 of SEQ ID NO: 99 based on the SignalP program that predicts nucleotides 1 to 45 of SEQ ID NO: 99 encode a signal peptide. In another aspect, the mature polypeptide coding sequence is nucleotides 52 to 1339 of SEQ ID NO: 107 based on the SignalP program that predicts nucleotides 1 to 51 of SEQ ID NO: 107 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Polypeptide fragment: The term "polypeptide fragment" means a polypeptide having one or more (several) amino acids deleted from the amino and/or carboxyl terminus of a mature polypeptide, wherein the fragment has enzyme activity, e.g., subtilisin-like serine protease, aspartic protease, or serine protease activity. In one aspect, a fragment contains at least 740 amino acid residues, e.g., at least 780 amino acid residues or at least 820 amino acid residues of the mature polypeptide of SEQ ID NO: 2 or a homologous sequence thereof. In another aspect, a fragment contains at least 320 amino acid residues, e.g., at least 340 amino acid residues or at least 360 amino acid residues of the mature polypeptide of SEQ ID NO: 4 or a homologous sequence thereof. In another aspect, a fragment contains at least 210 amino acid residues, e.g., at least 220 amino acid residues or at least 230 amino acid residues of the mature polypeptide of SEQ ID NO: 6 or a homologous sequence thereof. In another aspect, a fragment contains at least 460 amino acid residues, e.g., at least 480 amino acid residues or at least 500 amino acid residues of the mature polypeptide of SEQ ID NO: 100 or a homologous sequence thereof. In another aspect, a fragment contains at least 320 amino acid residues, e.g., at least 340 amino acid residues or at least 360 amino acid residues of the mature polypeptide of SEQ ID NO: 108 or a homologous sequence thereof.

Subsequence: The term "subsequence" means a nucleotide sequence having one or more (several) nucleotides deleted from the 5' and/or 3' end of a mature polypeptide coding sequence, wherein the subsequence encodes a polypeptide fragment having enzyme activity, e.g., subtilisin-like serine protease, aspartic protease, or serine protease. In one aspect, a subsequence contains at least 2220 nucleotides, e.g., at least 2340 nucleotides or at least 2460 nucleotides of the mature polypeptide coding sequence of SEQ ID NO: 1 or the cDNA sequence thereof, or a homologous sequence thereof. In another aspect, a subsequence contains at least 960 nucleotides, e.g., at least 1020 nucleotides or at least 1080 nucleotides of the mature polypeptide coding sequence of SEQ ID NO: 3 or the cDNA sequence thereof, or a homologous sequence thereof. In another aspect, a subsequence contains at least 630 nucleotides, e.g., at least 660 nucleotides or at least 690 nucleotides of the mature polypeptide coding sequence of SEQ ID NO: 5 or the cDNA sequence thereof, or a homologous sequence thereof. In another aspect, a subsequence contains at least 1380 nucleotides, e.g., at least 1440 nucleotides or at least 1500 nucleotides of the mature polypeptide coding sequence of SEQ ID NO: 99 or the cDNA sequence thereof, or a homologous sequence thereof. In another aspect, a subsequence contains at least 960 nucleotides, e.g., at least 1020 nucleotides, or at least 1080 nucleotides of the mature polypeptide coding sequence of SEQ ID NO: 107 or the cDNA sequence thereof, or a homologous sequence thereof.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a gwnomic DNA, cDNA, synthetic DNA, or a combination thereof.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

Control sequences: The term "control sequences" means all components necessary for the expression of a polynucleotide encoding a polypeptide. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide. The term "host cell" encompasses any progeny of a parent cell that is not identical to the parent cell due to mutations that occur during replication.

Modification: The term "modification" means introduction, substitution, or removal of one or more (several) nucleotides in a gene or a control sequence required for the transcription or translation thereof, or gene disruption, gene conversion, gene deletion, or random or specific mutagenesis of a gene, e.g., a first subtilisin-like serine protease gene, a first aspartic protease gene, a trypsin-like serine protease gene, a second subtilisin-like serine protease gene, a second aspartic protease gene, or a combination thereof. The deletion of one or more (several) of the first subtilisin-like serine protease gene, the first aspartic protease gene, the trypsin-like serine protease gene, the second subtilisin-like serine protease gene, and/or the second aspartic protease gene may be partial or complete. The modification results in a decrease in or elimination (inactivation) of expression of the first subtilisin-like serine protease, the first aspartic protease, the trypsin-like serine protease, the second subtilisin-like serine protease, the second aspartic protease, or a combination thereof. In a preferred aspect, one or more (several) of the first subtilisin-like serine protease gene, the first aspartic protease gene, the trypsin-like serine protease gene, the second subtilisin-like serine protease gene, and the second aspartic protease gene are inactivated.

DETAILED DESCRIPTION OF THE INVENTION

The present invention relates to mutants of a parent *Trichoderma* strain, comprising a polynucleotide encoding a polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions.

The present invention also relates to methods of producing a polypeptide, comprising: (a) cultivating a mutant of a parent *Trichoderma* strain in a medium for the production of the polypeptide, wherein the mutant strain comprises a polynucleotide encoding the polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions; and (b) recovering the polypeptide from the cultivation medium.

The present invention further relates to methods of obtaining mutants of a parent *Trichoderma* strain, comprising: (a) modifying one or more (several) genes selected from the group consisting of a first subtilisin-like serine protease gene, a first aspartic protease gene, a trypsin-like serine protease gene, a second subtilisin-like serine protease gene, and a second aspartic protease gene; and (b) identifying a mutant strain from step (a) wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions.

An advantage of the present invention is elimination or reduction of one or more (several) enzyme activities, which may be detrimental to the production, downstream processing, e.g., recovery, and/or application of a particular polypeptide of interest.

In the methods of the present invention, the parent *Trichoderma* strain may be any *Trichoderma* strain such as a wild-type *Trichoderma* strain or a mutant thereof. The parent *Trichoderma* strain may be *Trichoderma harzianum*, *Trichoderma koningii*, *Trichoderma longibrachiatum*, *Trichoderma reesei*, or *Trichoderma viride*; or the alternative sexual form thereof, i.e., *Hypocrea*.

In another aspect, the parent *Trichoderma* strain is *Trichoderma harzianum*. In another aspect, the parent *Trichoderma* strain is *Trichoderma koningii*. In another aspect, the parent *Trichoderma* strain is *Trichoderma longibrachiatum*. In another aspect, the parent *Trichoderma* strain is *Trichoderma reesei*. In another aspect, the parent *Trichoderma* strain is *Trichoderma viride*.

In another aspect, the parent *Trichoderma reesei* strain is *Trichoderma reesei* RutC30. In another aspect, the parent *Trichoderma reesei* strain is *Trichoderma reesei* TV10. In another aspect, the parent *Trichoderma reesei* strain is a mutant of *Trichoderma reesei*. In another aspect, the parent *Trichoderma reesei* strain is a morphological mutant of *Trichoderma reesei* (see WO 97/26330).

The protease-deficient *Trichoderma* mutant strain may be constructed by reducing or eliminating expression of one or more (several) genes selected from the group consisting of a first subtilisin-like serine protease gene, a first aspartic protease gene, a trypsin-like serine protease gene, a second subtilisin-like serine protease gene, and a second aspartic protease gene using methods well known in the art, such as insertions, disruptions, replacements, or deletions. A portion of the gene can be modified such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The *Trichoderma* mutant strains may be constructed by gene deletion techniques to eliminate or reduce expression of the gene. Gene deletion techniques enable the partial or complete removal of the gene thereby eliminating their expression. In such methods, deletion of the gene is accomplished by homologous recombination using a plasmid that has been constructed to contiguously contain the 5' and 3' regions flanking the gene.

The *Trichoderma* mutant strains may also be constructed by introducing, substituting, and/or removing one or more (several) nucleotides in the gene or a control sequence thereof required for the transcription or translation thereof. For example, nucleotides may be inserted or removed for the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proceedings of the National Academy of Sciences USA* 81: 2285; Higuchi et al., 1988, *Nucleic Acids Research* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The *Trichoderma* mutant strains may also be constructed by gene disruption techniques by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The *Trichoderma* mutant strains may also be constructed by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence, which is then transformed into the parent *Trichoderma* strain to produce a defective gene. By homologous recombination, the defective nucleotide sequence replaces the endogenous gene. It may be desirable that the defective nucleotide sequence also comprises a marker for selection of transformants containing the defective gene.

The *Trichoderma* mutant strains may also be constructed by established anti-sense techniques using a nucleotide sequence complementary to the nucleotide sequence of the gene (Parish and Stoker, 1997, *FEMS Microbiology Letters* 154: 151-157). More specifically, expression of the gene by a *Trichoderma* strain may be reduced or inactivated by introducing a nucleotide sequence complementary to the nucleotide sequence of the gene, which may be transcribed in the strain and is capable of hybridizing to the mRNA produced in the strain. Under conditions allowing the complementary anti-sense nucleotide sequence to hybridize to the mRNA, the amount of protein translated is thus reduced or eliminated.

The *Trichoderma* mutant strains may also be constructed by established RNA interference (RNAi) techniques (see, for example, WO 2005/056772 and WO 2008/080017).

The *Trichoderma* mutant strains may be further constructed by random or specific mutagenesis using methods well known in the art, including, but not limited to, chemical mutagenesis (see, for example, Hopwood, The Isolation of Mutants in *Methods in Microbiology* (J. R. Norris and D. W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

In one aspect, the modification results in the inactivation of one or more (several) genes selected from the group consisting of a first subtilisin-like serine protease gene, a first aspartic protease gene, a trypsin-like serine protease gene, a second subtilisin-like serine protease gene, and a second aspartic protease gene. In another aspect, the modification results in a decrease in expression of one or more (several) genes selected from the group consisting of a first subtilisin-like serine protease gene, a first aspartic protease gene, a trypsin-like serine protease gene, a second subtilisin-like serine protease gene, and a second aspartic protease gene. In another aspect, the modification results in expression of one or more (several) genes selected from the group consisting of a first subtilisin-like serine protease gene, a first aspartic protease gene, a trypsin-like serine protease gene, a second subtilisin-like serine protease gene, and a second aspartic protease gene being decreased, inactivated, or a combination thereof.

In another aspect, the mutant comprises a modification of a first subtilisin-like serine protease gene. In another aspect, the mutant comprises a modification of a first aspartic protease gene. In another aspect, the mutant comprises a modification of a trypsin-like serine protease gene. In another aspect, the mutant comprises a modification of a second subtilisin-like serine protease gene. In another aspect, the mutant comprises a modification of a second aspartic protease gene.

In another aspect, the mutant comprises a modification of a first subtilisin-like serine protease gene and a first aspartic protease gene. In another aspect, the mutant comprises a modification of a first subtilisin-like serine protease gene and a trypsin-like serine protease gene. In another aspect, the mutant comprises a modification of a first subtilisin-like serine protease gene and a second subtilisin-like serine protease gene. In another aspect, the mutant comprises a modification of a first subtilisin-like serine protease gene and a second aspartic protease gene. In another aspect, the mutant comprises a modification of a first aspartic protease gene and a trypsin-like serine protease gene. In another aspect, the mutant comprises a modification of a first aspartic protease gene and a second subtilisin-like serine protease gene. In another aspect, the mutant comprises a modification of a first aspartic protease gene and a second aspartic protease gene. In another aspect, the mutant comprises a modification of a trypsin-like serine protease gene and a second subtilisin-like serine protease gene. In another aspect, the mutant comprises a modification of a trypsin-like serine protease gene and a second aspartic protease gene. In another aspect, the mutant comprises a modification of a second subtilisin-like serine protease gene and a second aspartic protease gene.

In another aspect, the mutant comprises a modification of a first subtilisin-like serine protease gene, a first aspartic protease gene, and a trypsin-like serine protease gene. In another aspect, the mutant comprises a modification of a first subtilisin-like serine protease gene, a trypsin-like serine protease gene, and a second subtilisin-like serine protease gene. In another aspect, the mutant comprises a modification of a first subtilisin-like serine protease gene, a second subtilisin-like serine protease gene, and a second aspartic protease gene. In another aspect, the mutant comprises a modification of a first subtilisin-like serine protease gene, a first aspartic protease gene, and a second subtilisin-like serine protease gene. In another aspect, the mutant comprises a modification of a first subtilisin-like serine protease gene, a first aspartic protease gene, and a second aspartic protease gene. In another aspect, the mutant comprises a modification of a first subtilisin-like serine protease gene, a trypsin-like serine protease gene, and a second aspartic protease gene. In another aspect, the mutant comprises a modification of a first aspartic protease gene, a trypsin-like serine protease gene, and a second subtilisin-like serine protease gene. In another aspect, the mutant comprises a modification of a first aspartic protease gene, a second subtilisin-like serine protease gene, and a second aspartic protease gene. In another aspect, the mutant comprises a modification of a first aspartic protease gene, a trypsin-like serine protease gene, and a second aspartic protease gene. In another aspect, the mutant comprises a modification of a trypsin-like serine protease gene, a second subtilisin-like serine protease gene, and a second aspartic protease gene.

In another aspect, the mutant comprises a modification of a first subtilisin-like serine protease gene, a first aspartic protease gene, a trypsin-like serine protease gene, and a second subtilisin-like serine protease gene. In another aspect, the mutant comprises a modification of a first subtilisin-like serine protease gene, a trypsin-like serine protease gene, a second subtilisin-like serine protease gene, and a second aspartic protease gene. In another aspect, the mutant comprises a modification of a first aspartic protease gene, a trypsin-like serine protease gene, a second subtilisin-like serine protease gene, and a second aspartic protease gene. In another aspect, the mutant comprises a modification of a first subtilisin-like serine protease gene, a first aspartic protease gene, a second subtilisin-like serine protease gene, and a second aspartic protease gene. In another aspect, the mutant comprises a modification of a first subtilisin-like serine protease gene, a first aspartic protease gene, a trypsin-like serine protease gene, and a second aspartic protease gene.

In another aspect, the mutant comprises a modification of a first subtilisin-like serine protease gene, a first aspartic protease gene, a trypsin-like serine protease gene, a second subtilisin-like serine protease gene, and a second aspartic protease gene.

In one aspect, the first subtilisin-like serine protease gene encodes a polypeptide having subtilisin-like serine protease activity comprising or consisting of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide thereof. In another aspect, the first subtilisin-like serine protease gene encodes a polypeptide having subtilisin-like serine protease activity comprising or consisting of SEQ ID NO: 2. In another aspect, the first subtilisin-like serine protease gene encodes a polypeptide having subtilisin-like serine protease activity comprising or consisting of the mature polypeptide of SEQ ID NO: 2.

In another aspect, the first subtilisin-like serine protease gene comprises a polynucleotide comprising or consisting of a nucleotide sequence having at least 60%, e.g., e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or the mature polypeptide coding sequence thereof. In another aspect, the first subtilisin-like serine protease gene comprises a polynucleotide comprising or consisting of SEQ ID NO: 1. In another aspect, the first subtilisin-like serine protease gene comprises a polynucleotide comprising or consisting of the mature polypeptide coding sequence of SEQ ID NO: 1.

In another aspect, the first subtilisin-like serine protease gene comprises a polynucleotide that hybridizes under very low stringency conditions, low stringency conditions, medium stringency conditions, medium-high stringency conditions, high stringency conditions, or very high stringency conditions with (i) SEQ ID NO: 1; (ii) the mature polypeptide coding sequence of SEQ ID NO: 1, (iii) the cDNA sequence of (i) or (ii), or (iv) a full-length complementary strand of (i), (ii), or (iii).

In another aspect, the first subtilisin-like serine protease comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide thereof. In another aspect, the first subtilisin-like serine protease comprises or consists of SEQ ID NO: 2. In another aspect, the first subtilisin-like serine protease comprises or consists of the mature polypeptide of SEQ ID NO: 2.

In another aspect, the first subtilisin-like serine protease is encoded by a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or the cDNA thereof, or the mature polypeptide coding sequence thereof. In another aspect, the first subtilisin-like serine protease is encoded by a polynucleotide comprising or consisting of SEQ ID NO: 1. In another aspect, the first subtilisin-like serine protease is encoded by a polynucleotide comprising or consisting of the mature polypeptide coding sequence of SEQ ID NO: 1.

In another aspect, the first subtilisin-like serine protease is encoded by a polynucleotide that hybridizes under very low stringency conditions, low stringency conditions, medium stringency conditions, medium-high stringency conditions, high stringency conditions, or very high stringency conditions with (i) SEQ ID NO: 1; (ii) the mature polypeptide coding sequence of SEQ ID NO: 1, (iii) the cDNA sequence of (i) or (ii), or (iv) a full-length complementary strand of (i), (ii), or (iii).

In another aspect, the first aspartic protease gene encodes a polypeptide having aspartic protease activity comprising or consisting of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide thereof. In another aspect, the first aspartic protease gene encodes a polypeptide having aspartic protease activity comprising or consisting of SEQ ID NO: 4. In another aspect, the first aspartic protease gene encodes a polypeptide having aspartic protease activity comprising or consisting of the mature polypeptide of SEQ ID NO: 4.

In another aspect, the first aspartic protease gene comprises a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3 or the cDNA thereof, or the mature polypeptide coding sequence thereof. In another aspect, the first aspartic protease gene comprises or consists of SEQ ID NO: 3. In another aspect, the first aspartic protease gene comprises or consists of the mature polypeptide coding sequence of SEQ ID NO: 3.

In another aspect, the first aspartic protease gene comprises a polynucleotide that hybridizes under very low stringency conditions, low stringency conditions, medium stringency conditions, medium-high stringency conditions, high stringency conditions, or very high stringency conditions with (i) SEQ ID NO: 3; (ii) the mature polypeptide coding sequence of SEQ ID NO: 3, (iii) the cDNA sequence of (i) or (ii), or (iv) a full-length complementary strand of (i), (ii), or (iii).

In another aspect, the first aspartic protease comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide thereof. In another aspect, the first aspartic protease comprises or consists of SEQ ID NO: 4. In another aspect, the first aspartic protease comprises or consists of the mature polypeptide of SEQ ID NO: 4.

In another aspect, the first aspartic protease is encoded by a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3 or the cDNA thereof, or the mature polypeptide coding sequence thereof. In another aspect, the first aspartic protease is encoded by a polynucleotide comprising or consisting of SEQ ID NO: 3. In another aspect, the first aspartic protease is encoded by a polynucleotide comprising or consisting of the mature polypeptide coding sequence of SEQ ID NO: 3.

In another aspect, the first aspartic protease is encoded by a polynucleotide that hybridizes under very low stringency conditions, low stringency conditions, medium stringency conditions, medium-high stringency conditions, high stringency conditions, or very high stringency conditions with (i) SEQ ID NO: 3; (ii) the mature polypeptide coding sequence of SEQ ID NO: 3, (iii) the cDNA sequence of (i) or (ii), or (iv) a full-length complementary strand of (i), (ii), or (iii).

In another aspect, the trypsin-like serine protease gene encodes a polypeptide having trypsin-like serine protease activity comprising or consisting of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6 or the mature polypeptide thereof. In another aspect, the trypsin-like serine protease gene encodes a polypeptide having trypsin-like serine protease activity comprising or consisting of SEQ ID NO: 6. In another aspect, the trypsin-like serine protease gene encodes a polypeptide having trypsin-like serine protease activity comprising or consisting of the mature polypeptide of SEQ ID NO: 6.

In another aspect, the trypsin-like serine protease gene comprises a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5 or the cDNA thereof, or the mature polypeptide coding sequence thereof. In another aspect, the trypsin-like serine protease gene comprises a polynucleotide comprising or consisting of SEQ ID NO: 5. In another aspect, the trypsin-like serine protease gene comprises a polynucleotide comprising or consisting of the mature polypeptide coding sequence of SEQ ID NO: 5.

In another aspect, the trypsin-like serine protease gene comprises a polynucleotide that hybridizes under very low stringency conditions, low stringency conditions, medium stringency conditions, medium-high stringency conditions, high stringency conditions, or very high stringency conditions with (i) SEQ ID NO: 5; (ii) the mature polypeptide coding sequence of SEQ ID NO: 5, (iii) the cDNA sequence of (i) or (ii), or (iv) a full-length complementary strand of (i), (ii), or (iii).

In another aspect, the trypsin-like serine protease comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6 or the mature polypeptide thereof. In another aspect, the first aspartic protease comprises or consists of SEQ ID NO: 6. In another aspect, the first aspartic protease comprises or consists of the mature polypeptide of SEQ ID NO: 6.

In another aspect, the trypsin-like serine protease is encoded by a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5 or the cDNA thereof, or the mature polypeptide coding sequence thereof. In another aspect, the trypsin-like serine protease is encoded by a polynucleotide comprising or consisting of SEQ ID NO: 5. In another aspect, the trypsin-like serine protease is encoded by a polynucleotide comprising or consisting of the mature polypeptide coding sequence of SEQ ID NO: 5.

In another aspect, the trypsin-like serine protease is encoded by a polynucleotide that hybridizes under very low stringency conditions, low stringency conditions, medium stringency conditions, medium-high stringency conditions, high stringency conditions, or very high stringency conditions with (i) SEQ ID NO: 5; (ii) the mature polypeptide coding sequence of SEQ ID NO: 5, (iii) the cDNA sequence of (i) or (ii), or (iv) a full-length complementary strand of (i), (ii), or (iii).

In another aspect, the second subtilisin-like serine protease gene encodes a polypeptide having subtilisin-like serine protease activity comprising or consisting of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 100 or the mature polypeptide thereof. In another aspect, the second subtilisin-like serine protease gene encodes a polypeptide having subtilisin-like serine protease activity comprising or consisting of SEQ ID NO: 100. In another aspect, the second subtilisin-like serine protease gene encodes a polypeptide having subtilisin-like serine protease activity comprising or consisting of the mature polypeptide of SEQ ID NO: 100.

In another aspect, the second subtilisin-like serine protease gene comprises a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 99 or the cDNA thereof, or the mature polypeptide coding sequence thereof. In another aspect, the second subtilisin-like serine protease gene comprises or consists of SEQ ID NO: 99. In another aspect, the second subtilisin-like serine protease gene comprises or consists of the mature polypeptide coding sequence of SEQ ID NO: 99.

In another aspect, the second subtilisin-like serine protease gene comprises a polynucleotide that hybridizes under very low stringency conditions, low stringency conditions, medium stringency conditions, medium-high stringency conditions, high stringency conditions, or very high stringency conditions with (i) SEQ ID NO: 99; (ii) the mature polypeptide coding sequence of SEQ ID NO: 99, (iii) the cDNA sequence of (i) or (ii), or (iv) a full-length complementary strand of (i), (ii), or (iii).

In another aspect, the second subtilisin-like serine protease comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 100 or the mature polypeptide thereof. In another aspect, the second subtilisin-like serine protease comprises or consists of SEQ ID NO: 100. In another aspect, the second subtilisin-like serine protease comprises or consists of the mature polypeptide of SEQ ID NO: 100.

In another aspect, the second subtilisin-like serine protease is encoded by a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 99 or the cDNA thereof, or the mature polypeptide coding sequence thereof. In another aspect, the second subtilisin-like serine protease is encoded by a polynucleotide comprising or consisting of SEQ ID NO: 99. In another aspect, the second subtilisin-like serine protease is encoded by a polynucleotide comprising or consisting of the mature polypeptide coding sequence of SEQ ID NO: 99.

In another aspect, the second subtilisin-like serine protease is encoded by a polynucleotide that hybridizes under very low stringency conditions, low stringency conditions, medium stringency conditions, medium-high stringency conditions, high stringency conditions, or very high stringency conditions with (i) SEQ ID NO: 99; (ii) the mature polypeptide coding sequence of SEQ ID NO: 99, (iii) the cDNA sequence of (i) or (ii), or (iv) a full-length complementary strand of (i), (ii), or (iii).

In one aspect, the second aspartic protease gene encodes a polypeptide having aspartic protease activity comprising or consisting of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 108 or the mature polypeptide thereof. In another aspect, the second aspartic protease gene encodes a polypeptide having aspartic protease activity comprising or consisting of SEQ ID NO: 108. In another aspect, the second aspartic protease gene encodes a polypeptide having aspartic protease activity comprising or consisting of the mature polypeptide of SEQ ID NO: 108.

In another aspect, the second aspartic protease gene comprises a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 107 or the cDNA thereof, or the mature polypeptide coding sequence thereof. In another aspect, the second aspartic protease gene comprises or consists of SEQ ID NO: 107. In another aspect, the second aspartic protease gene comprises or consists of the mature polypeptide coding sequence of SEQ ID NO: 107.

In another aspect, the second aspartic protease gene comprises a polynucleotide that hybridizes under very low stringency conditions, low stringency conditions, medium stringency conditions, medium-high stringency conditions, high stringency conditions, or very high stringency conditions with (i) SEQ ID NO: 107; (ii) the mature polypeptide coding sequence of SEQ ID NO: 107, (iii) the cDNA sequence of (i) or (ii), or (iv) a full-length complementary strand of (i), (ii), or (iii).

In another aspect, the second aspartic protease comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 108 or the mature polypeptide thereof. In another aspect, the second aspartic protease comprises or consists of SEQ ID NO: 108. In another aspect, the second aspartic protease comprises or consists of the mature polypeptide of SEQ ID NO: 108.

In another aspect, the second aspartic protease is encoded by a polynucleotide comprising or consisting of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 107 or the cDNA thereof, or the mature polypeptide coding sequence thereof. In another aspect, the second aspartic protease is encoded by a polynucleotide comprising or consisting of SEQ ID NO: 107. In another aspect, the second aspartic protease is encoded by a polynucleotide comprising or consisting of the mature polypeptide coding sequence of SEQ ID NO: 107.

In another aspect, the second aspartic protease is encoded by a polynucleotide that hybridizes under very low stringency conditions, low stringency conditions, medium stringency conditions, medium-high stringency conditions, high stringency conditions, or very high stringency conditions with (i) SEQ ID NO: 107; (ii) the mature polypeptide coding sequence of SEQ ID NO: 107, (iii) the cDNA sequence of (i) or (ii), or (iv) a full-length complementary strand of (i), (ii), or (iii).

The nucleotide sequences disclosed herein or subsequences thereof, as well as the amino acid sequences thereof or fragments thereof, may be used to design nucleic acid probes to identify and clone homologous DNA of the genes described above from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

Thus, a genomic DNA or cDNA library prepared from such other organisms may be screened for DNA that hybridizes with the probes described above. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with the nucleotide sequences disclosed herein or subsequences thereof, the carrier material is used in a Southern blot. For purposes of the present invention, hybridization indicates that the nucleic acid sequence hybridizes to a labeled nucleic acid probe corresponding to the nucleotide sequences disclosed herein, its complementary strand, or a subsequence thereof, under very low to very high stringency conditions. Molecules to which the nucleic acid probe hybridizes under these conditions are detected using X-ray film.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, Proc. Natl. Acad. Sci. USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

A nucleotide sequence homologous or complementary to a gene described herein may be used from other microbial sources to modify the corresponding gene in a Trichoderma strain of choice.

In another aspect, the modification of a gene in the Trichoderma mutant strain is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

It will be understood that the methods of the present invention are not limited to a particular order for obtaining the Trichoderma mutant strain. The modification of a gene may be introduced into the parent strain at any step in the construction of the strain for the production of a polypeptide of interest. It is preferred that the Trichoderma mutant strain has already been made protease-deficient prior to such a construction.

In a further aspect of the present invention, the mutants of Trichoderma strains may contain additional modifications, e.g., deletions or disruptions, of other genes, which may encode substances detrimental to the production, recovery, or application of a polypeptide of interest.

In one aspect, the Trichoderma strain further comprises a modification, e.g., disruption or deletion, of one or more (several) genes encoding a proteolytic activity selected from the group consisting of an aminopeptidase, dipeptidylaminopeptidase, tripeptidylaminopeptidase, carboxypeptidase, metalloprotease, cysteine protease, and vacuolar protease.

In another aspect, the Trichoderma strain further comprises a modification, e.g., disruption or deletion, of one or more (several) additional genes encoding an oxidoreductase, a transferase, a hydrolase, a lyase, an isomerase, or a ligase.

In another aspect, the Trichoderma strain further comprises a modification, e.g., disruption or deletion, of one or more (several) additional genes encoding an enzyme selected from the group consisting of an alpha-amylase, arabinofuranosidase, carbohydrase, catalase, cellobiohydrolase, cellulase, chitinase, cyclodextrin glycosyltransferase, cutinase, cyclodextrin glycosyltransferase, deoxyribonuclease, endoglucanase, esterase, alpha-galactosidase, beta-galactosidase, glucocerebrosidase, glucose oxidase, alpha-glucosidase, beta-glucosidase, glucuronidases, haloperoxidase, hemicellulase, invertase, isomerase, laccase, ligase, lipase, mannosidase, mutanase, oxidase, pectinolytic enzyme, peroxidase, phospholipase, phytase, phenoloxidase, polyphenoloxidase, ribonuclease, alpha-1,6-transglucosidase, transglutaminase, urokinase, xylanase, and beta-xylosidase.

In another aspect, the Trichoderma strain further comprises a modification, e.g., disruption or deletion, of one or more (several) additional genes encoding an enzyme selected from the group consisting of an endoglucanase, a cellobiohydrolase, and a beta-glucosidase, In the methods of the present invention, the Trichoderma mutant strain preferably produces at least the same amount of a biologically active polypeptide of interest as the corresponding parent Trichoderma strain when cultured under identical production conditions. In another aspect, the mutant strain produces preferably at least 5% more, more preferably at least 10% more, more preferably at least 25% more, more preferably at least 50% more, even more preferably at least 75% more, and most preferably at least 100% more of the biologically active polypeptide than the corresponding parent Trichoderma strain when cultured under identical production conditions.

The Trichoderma mutant strains are cultivated in a nutrient medium for production of the polypeptide of interest using methods known in the art. For example, the strain may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium. If the polypeptide is not secreted, it may be obtained from cell lysates.

The polypeptide of interest may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of an enzyme. Procedures for determining enzyme activity are known in the art for many enzymes (see, for example, D. Schomburg and M. Salzmann (eds.), *Enzyme Handbook*, Springer-Verlag, New York, 1990).

The resulting polypeptide may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

The polypeptide of interest may be any polypeptide native or foreign (heterologous) to the *Trichoderma* strain. The polypeptide may be encoded by a single gene or two or more genes. The term "polynucleotide encoding the polypeptide" will be understood to encompass one or more (several) genes involved in the production of the polypeptide. The term "heterologous polypeptide" is defined herein as a polypeptide that is not native to the host strain; a native polypeptide in which structural modifications have been made to alter the native polypeptide, e.g., the protein sequence of a native polypeptide; or a native polypeptide whose expression is quantitatively altered as a result of a manipulation of the polynucleotide or host strain by recombinant DNA techniques, e.g., a stronger promoter, multiple copies of a DNA encoding the polypeptide. Thus, the present invention also encompasses, within the scope of the term "heterologous polypeptides," such recombinant production of native polypeptides, to the extent that such expression involves the use of genetic elements not native to the *Trichoderma* strain, or use of native elements that have been manipulated to function in a manner that do not normally occur in the host strain. In one aspect, the polypeptide is a native polypeptide to the *Trichoderma* strain. In another aspect, the polypeptide is a heterologous polypeptide to the *Trichoderma* strain.

The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include fusion polypeptides, which comprise a combination of partial or complete polypeptide sequences obtained from at least two different polypeptides wherein one or more (several) may be heterologous to the *Trichoderma* strain. Polypeptides further include naturally occurring allelic and engineered variations of the above-mentioned polypeptides and hybrid polypeptides.

In one aspect, the polypeptide is an antibody, an antigen, an antimicrobial peptide, an enzyme, a growth factor, a hormone, an immunodilator, a neurotransmitter, a receptor, a reporter protein, a structural protein, or a transcription factor.

In another aspect, the polypeptide is an oxidoreductase, a transferase, a hydrolase, a lyase, an isomerase, or a ligase. In another aspect, the polypeptide is an acetylmannan esterase, acetyxylan esterase, aminopeptidase, alpha-amylase, arabinanase, arabinofuranosidase, carbohydrase, carboxypeptidase, catalase, cellobiohydrolase, cellulase, chitinase, coumaric acid esterase, cyclodextrin glycosyltransferase, cutinase, cyclodextrin glycosyltransferase, deoxyribonuclease, endoglucanase, esterase, feruloyl esterase, GH61 polypeptide having cellulolytic enhancing activity, alpha-galactosidase, beta-galactosidase, glucocerebrosidase, glucose oxidase, alpha-glucosidase, beta-glucosidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, alpha-1,6-transglucosidase, transglutaminase, urokinase, xylanase, or beta-xylosidase.

In another aspect, the polypeptide is an albumin, a collagen, a tropoelastin, an elastin, or a gelatin.

In another aspect, the polypeptide is an endoglucanase. In another aspect, the polypeptide is a cellobiohydrolase. In another aspect, the polypeptide is a beta-glucosidase. In another aspect, the polypeptide is a GH61 polypeptide having cellulolytic enhancing activity. In another aspect, the polypeptide is a xylanase. In another aspect, the polypeptide is a beta-xylosidase. In another aspect, the polypeptide is an acetyxylan esterase. In another aspect, the polypeptide is a feruloyl esterase. In another aspect, the polypeptide is an arabinofuranosidase. In another aspect, the polypeptide is a glucuronidase. In another aspect, the polypeptide is an acetylmannan esterase. In another aspect, the polypeptide is an arabinanase. In another aspect, the polypeptide is a coumaric acid esterase. In another aspect, the polypeptide is a galactosidase. In another aspect, the polypeptide is a glucuronoyl esterase. In another aspect, the polypeptide is a mannanase. In another aspect, the polypeptide is a mannosidase.

In the methods of the present invention, the mutant of the *Trichoderma* strain is a recombinant strain, comprising a polynucleotide encoding a heterologous polypeptide, which is advantageously used in the recombinant production of the polypeptide. The strain is preferably transformed with a vector comprising the polynucleotide encoding the heterologous polypeptide followed by integration of the vector into the chromosome. "Transformation" means introducing a vector comprising the polynucleotide into a host strain so that the vector is maintained as a chromosomal integrant or as a self-replicating extra-chromosomal vector. Integration is generally considered to be an advantage as the polynucleotide is more likely to be stably maintained in the strain. Integration of the vector into the chromosome can occur by homologous recombination, non-homologous recombination, or transposition.

The polynucleotide encoding a heterologous polypeptide may be obtained from any prokaryotic, eukaryotic, or other source, e.g., archaeabacteria. For purposes of the present invention, the term "obtained from" as used herein in connection with a given source shall mean that the polypeptide is produced by the source or by a strain in which a gene from the source has been inserted.

In the methods of the present invention, the polypeptide may also be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In the methods of the present invention, a mutant *Trichoderma* strain of the present invention may also be used for the recombinant production of a polypeptide that is native to the *Trichoderma* strain. The native polypeptide may be produced by recombinant means by, for example, placing a gene encoding the polypeptide under the control of a different promoter to enhance expression of the substance, expediting its export outside the strain by use of, for example, a signal sequence, or increasing the copy number of a gene encoding the polypeptide normally produced by the *Trichoderma* strain.

The techniques used to isolate or clone a polynucleotide encoding a polypeptide of interest are known in the art and include isolation from genomic DNA, preparation from cDNA, or a combination thereof. The cloning of such a polynucleotide from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the polynucleotide encoding the polypeptide, insertion of the fragment into a vector molecule, and incorporation of the recombinant vector into a mutant *Trichoderma* strain of the present invention where multiple copies or clones of the polynucleotide will be replicated. The polynucleotide may be of genomic, cDNA, RNA, semisynthetic, synthetic origin, or any combinations thereof.

An isolated polynucleotide encoding a heterologous polypeptide may be manipulated in a variety of ways to provide for expression of the polypeptide in a mutant *Trichoderma* strain of the present invention. Manipulation of the polynucleotide's sequence prior to its insertion into a vector may be desirable or necessary depending on the expression vector. The techniques for modifying polynucleotide sequences utilizing recombinant DNA methods are well known in the art.

A nucleic acid construct comprising a polynucleotide encoding a polypeptide may be operably linked to one or more (several) control sequences capable of directing expression of the coding sequence in a mutant *Trichoderma* strain of the present invention under conditions compatible with the control sequences.

The control sequence may be an appropriate promoter sequence, a nucleotide sequence that is recognized by a mutant *Trichoderma* strain of the present invention for expression of the polynucleotide encoding the polypeptide. The promoter sequence contains transcriptional control sequences that mediate expression of the polypeptide. The promoter may be any nucleotide sequence that shows transcriptional activity in the mutant *Trichoderma* strain, including mutant, truncated, and hybrid promoters, and may be obtained from genes encoding extracellular or intracellular polypeptides either native or heterologous (foreign) to the mutant *Trichoderma* strain.

Examples of suitable promoters for directing the transcription of the nucleic acid constructs in the methods of the present invention are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

The control sequence may also be a suitable transcription terminator sequence, a sequence recognized by a mutant *Trichoderma* strain of the present invention to terminate transcription. The terminator sequence is operably linked to the 3' terminus of the nucleotide sequence encoding the heterologous polypeptide. Any terminator that is functional in a *Trichoderma* strain may be used in the present invention.

Preferred terminators are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA that is important for translation by a mutant *Trichoderma* strain of the present invention. The leader sequence is operably linked to the 5' terminus of the nucleotide sequence encoding the heterologous polypeptide. Any leader sequence that is functional in the mutant *Trichoderma* strain may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3' terminus of the nucleotide sequence and, when transcribed, is recognized by the mutant *Trichoderma* strain as a signal to add polyadenosine residues to transcribed mRNA. Any polyadenylation sequence that is functional in the mutant *Trichoderma* strain may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of the mutant *Trichoderma* strain, i.e., secreted into a culture medium, may be used in the present invention.

Effective signal peptide coding regions for the mutant *Trichoderma* strains are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from genes for *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

The nucleic acid constructs may also comprise one or more (several) polynucleotides that encode one or more (several) factors that are advantageous for directing expression of the heterologous polypeptide, e.g., a transcriptional activator (e.g., a trans-acting factor), a chaperone, and a processing protease. Any factor that is functional in the mutant *Trichoderma* strain may be used in the present invention. The nucleic acids encoding one or more (several) of these factors are not necessarily in tandem with the nucleotide sequence encoding the heterologous polypeptide.

It may also be desirable to add regulatory or control sequences that allow regulation of expression of the polypeptide relative to the growth of the mutant *Trichoderma* strain. Examples of regulatory systems are those that cause expression of the gene to be turned on or off in response to a chemical or physical stimulus, including the presence of a regulatory compound. Regulatory systems in filamentous fungi such as the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

In the methods of the present invention, a recombinant expression vector comprising a nucleotide sequence, a promoter, and transcriptional and translational stop signals may be used for the recombinant production of a polypeptide of interest. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on its compatibility with the mutant *Trichoderma* strain into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the mutant *Trichoderma* strain, is integrated into the genome and replicated together with the chromosome(s) into which it has been integrated. Furthermore, a single vector or plasmid or two or more vectors or plasmids that together contain the total DNA to be introduced into the genome of the mutant *Trichoderma* strain, or a transposon, may be used.

The vector preferably contains one or more (several) selectable markers that permit easy selection of transformed mutant *Trichoderma* strains. A selectable marker is a gene the product of which provides for biocide or viral resistance, resistance to heavy metals, prototrophy to auxotrophs, and the like.

Examples of selectable markers for use in the mutant *Trichoderma* strain include, but are not limited to, amdS (acetamidase), argB (ornithine carbamoyltransferase), bar (phosphinothricin acetyltransferase), hpt (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in the mutant *Trichoderma* strain are the amdS gene of *Aspergillus nidulans* and the bar gene of *Streptomyces hygroscopicus*.

The vectors preferably contain an element(s) that permits integration of the vector into the host cell's genome or autonomous replication of the vector in the cell independent of the genome.

For integration into the genome of the mutant *Trichoderma* strain, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the mutant *Trichoderma* strain at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the mutant *Trichoderma* strain. Furthermore, the integrational elements may be non-encoding or encoding nucleotide sequences. On the other hand, the vector may be integrated into the genome of the mutant *Trichoderma* strain by non-homologous recombination.

For autonomous replication, the vector may further comprise an origin of replication enabling the vector to replicate autonomously in the mutant *Trichoderma* strain. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in the mutant *Trichoderma* strain are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

The procedures used to ligate the elements described herein to construct the recombinant expression vectors are well known to one skilled in the art (see, e.g., J. Sambrook, E. F. Fritsch, and T. Maniatis, 1989, *Molecular Cloning, A Laboratory Manual*, 2d edition, Cold Spring Harbor, N.Y.).

A vector comprising the nucleotide sequence can be introduced, e.g., by transformation, into the mutant *Trichoderma* strain so that the vector is maintained as a chromosomal integrant or as a self-replicating extra-chromosomal vector. Integration is generally considered to be an advantage as the nucleotide sequence is more likely to be stably maintained in the strain. Integration of the vector into the chromosome occurs by homologous recombination, non-homologous recombination, or transposition.

The introduction of an expression vector into the mutant *Trichoderma* strain may involve a process consisting of protoplast formation, transformation of the protoplasts, and regeneration of the strain wall in a manner known per se. Suitable procedures for transformation of *Trichoderma* strains are described in Malardier et al., 1989, *Gene* 78: 147-156, and WO 96/00787.

The present invention is further described by the following examples that should not be construed as limiting the scope of the invention.

EXAMPLES

Strain

*Trichoderma reesei* strain 981-O-8 (D4) is a mutagenized strain of *Trichoderma reesei* RutC30 (ATCC 56765; Montenecourt and Eveleigh, 1979, *Adv. Chem. Ser.* 181: 289-301).

Media and Buffer Solutions

LB medium was composed of 10 g of tryptone, 5 g of yeast extract, and 5 g of sodium chloride, and deionized water to 1 liter.

LB plates were composed of 10 g of tryptone, 5 g of yeast extract, 5 g of NaCl, 15 g of Bacto agar, and deionized water to 1 liter.

PDA plates were composed of 39 g of Potato Dextrose Agar (Difco) and deionized water to 1 liter.

NZY top agarose was composed of 5 g of NaCl, 5 g of yeast extract, 10 g of NZ amine, 2 g of $MgSO_4$, 7 g of agarose, and deionized water to 1 liter.

YEG medium was composed of 5 g of yeast extract, 20 g of glucose, and deionized water to 1 liter.

2×YT agar plates were composed of 16 g of tryptone, 10 g of yeast extract, 5 g of sodium chloride, 15 g of Bactoagar, and deionized water to 1 liter.

*Trichoderma* minimal medium plates were composed of 30 g of sucrose, 20 ml of COVE salt solution, 0.6 g of $CaCl_2.2H_2O$, 6 g of $(NH_4)_2SO_4$, 25 g of Noble agar, and deionized water to 1 liter.

COVE plates were composed per liter of 342.3 g of sucrose, 25 g of Noble agar, 20 ml of COVE salts solution, 10 mM acetamide, and 15 or 20 mM CsCl. The solution was adjusted to pH 7.0 before autoclaving.

COVE2 plates were composed of 30 g of sucrose, 20 ml of COVE salt solution, 10 mM acetamide, 25 g or 30 g of Noble agar, and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g or 1 g of $MnSO_4$—$H_2O$, 0.8 g of $Na_2MoO_2.2H_2O$, 10 g of $ZnSO_4.7H_2O$, and deionized water to 1 liter.

COVE top agarose was composed of 342.3 g of sucrose, 20 ml of COVE salt solution, 10 mM acetamide, 10 g of low melt agarose, and deionized water to 1 liter.

Cellulase-inducing medium was composed of 20 g of Arbocel-natural cellulose fibers (J. Rettenmaier USA LP, Schoolcraft, Mich., USA), 10 g of corn steep solids (Sigma Chemical Co., St. Louis, Mo., USA), 1.45 g of $(NH_4)_2SO_4$, 2.08 g of $KH_2PO_4$, 0.28 g of $CaCl_2$, 0.42 g of $MgSO_4.7H_2O$, 0.42 ml of trace metals solution, 2 drops of pluronic acid, and deionized water to 1 liter. The pH was adjusted to 6.0 with 10 N NaOH before autoclaving.

Shake flask medium was composed of 20 g of dextrose, 10 g of corn steep solids, 1.45 g of $(NH_4)_2SO_4$, 2.08 g of $KH_2PO_4$, 0.36 g of $CaCl_2$, 0.42 g of $MgSO_4 \cdot 7H_2O$, and 0.42 ml of trace metals solution.

Fermentation batch medium was composed per liter of 30 g of cellulose, 4 g of dextrose, 10 g of corn steep solids, 3.8 g of $(NH_4)_2SO_4$, 2.8 g of $KH_2PO_4$, 2.64 g of $CaCl_2$, 1.63 g of $MgSO_4 \cdot 7H_2O$, 1.8 ml of anti-foam, 0.66 ml of trace metals solution, and deionized water to 1 liter.

Fermentation feed medium was composed of dextrose.

Trace metals solution was composed of 216 g of $FeCl_3 \cdot 6H_2O$, 58 g of $ZnSO_4 \cdot 7H_2O$, 27 g of $MnSO_4 \cdot H_2O$, 10 g of $CuSO_4 \cdot 5H_2O$, 2.4 g of $H_3BO_3$, 336 g of citric acid, and deionized water to 1 liter.

YP medium was composed of 10 g of yeast extract, 20 g of Bacto peptone, and deionized water to 1 liter.

YP+2% glucose medium was composed of 1% yeast extract, 2% peptone and 2% glucose in deionized water.

YP+2% maltodextrin medium was composed of 2% peptone, 2% maltodextrin, and 1% yeast extract in deionized water.

DAP-2C-1 medium was composed of 2% glucose, 1.1% magnesium sulfate, 1.0% maltose, 0.52% tri-potassium phosphate, 0.2% citric acid, 0.1% potassium dihydrogen phosphate, 0.1% Dowfax 63N10, 0.05% yeast extract, and 0.05% of a trace element solution (1.39% ferrous sulfate, 0.845% maganese sulfate, 0.68% zinc chloride, 0.3% citric acid, 0.25% copper sulfate, and 0.013% nickel chloride) in deionized water.

PEG buffer was composed of 500 g of PEG 4000, 10 mM $CaCl_2$, 10 mM Tris-HCl pH 7.5, and deionized water to 1 liter; filter sterilized.

STC was composed of 0.8 M or 1 M sorbitol, 10 mM or 25 mM $CaCl_2$, and 10 mM or 25 mM Tris-HCl, pH 7.5 or pH 8; filter sterilized.

TE Buffer was composed of 1 M Tris pH 8.0 and 0.5 M EDTA pH 8.0

20×SSC was composed of 175.3 g NaCl, 88.2 g of sodium citrate, and deionized water to 1 liter.

Example 1

Construction of Plasmid pDM156.2

A probe of a *Neurospora crassa* orotidine-5'-monophosphate decarboxylase (pyr-4) gene (SEQ ID NO: 7 for the DNA sequence and SEQ ID NO: 8 for the deduced amino acid sequence) was prepared by PCR incorporating digoxigenin-labeled deoxyuridine-triphosphate (dUTP) using the primers described below.

```
Primer (sense):
                                (SEQ ID NO: 9)
5'-GTCAGGAAACGCAGCCACAC-3'

Primer (anti-sense):
                                (SEQ ID NO: 10)
5'-AGGCAGCCCTTGGACGACAT-3'
```

Plasmid pFB6 (Buxton et al, 1983, *Molecular and General Genetics* 190: 403-405) was digested with Hind III and the digestion purified by 1% agarose gel electrophoresis using 40 mM Tris base-20 mM sodium acetate-1 mM disodium EDTA (TAE) buffer. A 1.1 kb pyr-4 fragment was excised from the gel and extracted using a QIAQUICK® Gel Extraction Kit (QIAGEN Inc., Valencia Calif., USA) according to the manufacturer's suggested protocols.

The amplification reaction (50 µl) was composed of 1× Taq DNA Polymerase Buffer (New England Biolabs Inc., Ipswich, Mass., USA), 5 µl of PCR DIG Labeling Mix (Roche Molecular Biochemicals, Indianapolis, Ind., USA), 10 ng of the 1.1 kb Hind III pyr-4 fragment, 10 pmol of the sense primer, 10 pmol of the anti-sense primer, and 1 unit of Taq DNA polymerase (New England Biolabs Inc., Ipswich, Mass., USA). The reaction was incubated in a ROBOCYCLER® (Stratagene, La Jolla, Calif., USA) programmed for 1 cycle at 95° C. for 3 minutes followed by 35 cycles each at 95° C. for 30 seconds, 55° C. for 1 minute, and 72° C. for 1 minute. A final extension was performed for 5 minutes at 72° C.

The amplification reaction products were purified by 1% agarose gel electrophoresis using TAE buffer. A digoxigenin (DIG) labeled probe of approximately 0.78 kb was excised from the gel and extracted using a QIAQUICK® Gel Extraction Kit.

A genomic DNA library of *Fusarium venenatum* strain A3/5 was generated and cloned into lambda vector EMBL4 as described in WO 99/60137.

The DIG-labeled probe was used to screen the genomic library of *Fusarium venenatum* A3/5 DNA cloned into lambda vector EMBL4. Lambda phages were plated with *E. coli* K802 cells (New England Biolabs, Ipswich, Mass., USA) onto LB plates with NZY top agarose. Plaque lifts were made to HYBOND™ N nylon membranes (Amersham Biosciences, Buckinghamshire, UK) using the technique of Sambrook et al. (*Molecular Cloning, A Laboratory Manual, Second Edition*; J. Sambrook, E. F. Fritsch, and T. Maniatis; Cold Spring Harbor Laboratory Press, 1989). DNA was bound to the membranes by UV cross-linking using a UV STRATALINKER™ (Stratagene, La Jolla, Calif., USA). Filters were then hybridized with the 0.78 kb DIG-labeled *N. crassa* pyr-4 probe. Hybridization and detection of pyrG clones were performed according to the GENIUS™ System User's Guide (Boehringer Hammheim, Manheim, Germany) at 42° C. with a hybridization solution composed of 5×SSC, 35% formamide, 0.1% L-lauroylsarcosine, 0.02% SDS, and 1% blocking reagent (Boehringer Hammheim, Manheim, Germany). The concentration of DIG-labeled probe used was 2.5 ng per ml of the hybridization solution. Hybridizing DNA was immuno-detected with an alkaline-phosphatase-conjugated anti-digoxigenin antibody (Boehringer Hammheim, Manheim, Germany) and visualized with Lumiphos 530, a chemiluminescent substrate (Boehringer Hammheim, Manheim, Germany). DNA preparations were made from putative positive lambda clones using a Lambda Midi Kit (QIAGEN Inc., Valencia, Calif., USA).

Lambda DNA from a clone identified above was digested with Eco RI and subjected to 1% agarose gel electrophoresis in TAE buffer. A 3.9 kb fragment was excised and extracted using a QIAEX® Gel Extraction Kit (QIAGEN Inc., Valencia, Calif., USA). The fragment was then cloned into the Eco RI site of pUC18 (Viera and Messing, 1987, *Methods in Enzymology* 153: 3-11) and ONE SHOT® TOP10 competent cells (Invitrogen, Carlsbad, Calif., USA) were transformed with 2 µl of the cloning reaction. Plasmid DNA from eight of the resulting transformants was analyzed by DNA sequencing. One clone with the desired sequence was selected and designated pDM156.2 (FIG. 1). The pyrG fragment harbored the entire coding region plus 1.3 kb of the promoter and 1.5 kb of the terminator.

Example 2

Construction of Plasmid pEmY21

An *E. coli* hygromycin phosphotransferase (hpt) gene (SEQ ID NO: 11 for the DNA sequence and SEQ ID NO: 12 for the deduced amino acid sequence) was amplified from plasmid pPHTI (Cummings et al., 1999, *Current Genetics* 36: 371-382) using the following primers:

```
Forward primer:
                                  (SEQ ID NO: 13)
5'-GGGttcgaaTTCATTTAAACGGCT-3'

Reverse primer:
                                  (SEQ ID NO: 14)
5'-GGGagcgctCAATATTCATCTCTC-3'
```

The restriction enzyme sites Bst BI (forward primer) and Eco 47III (reverse primer) were engineered into the primers, represented by the underlined sequence, for cloning.

The PCR reaction (to amplify the hpt gene) was composed of 1× ThermoPol reaction buffer (New England Biolabs, Inc, Ipswich, Mass., USA), 200 µM dNTPs, 50 pmol of the forward and reverse primers, 100 pg of pPHT1, 1 unit of VENT® DNA polymerase (New England Biolabs Inc., Ipswich, Mass. USA), and sterile distilled water in a total volume of 100 µl. The amplification reaction was performed using a ROBOCYCLER® programmed for 1 cycle at 95° C. for 2 minutes; 25 cycles each at 95° C. for 1 minute, 51° C. for 1 minute, and 72° C. for 2 minutes; and 1 cycle at 72° C. for 7 minutes.

PCR products were separated by 1% agarose gel electrophoresis in TAE buffer. A 1.8 kb fragment was excised from the gel and extracted using a QIAQUICK® Gel Extraction Kit. The gel purified fragment was then cloned into pCR®-BluntII-TOPO® (Invitrogen, Carlsbad, Calif., USA) using a TOPO® Blunt Cloning Kit (Invitrogen, Carlsbad, Calif., USA). The resulting plasmid was designated pEmY10.

The Eco RI site was then removed from the coding sequence of the hpt gene in pEmY10 using a QUIKCHANGE® Site-Directed Mutagenesis Kit (Stratagene, La Jolla, Calif., USA) according to the manufacturer's instructions using the primers shown below, where the lower case letters represent the non-mutated nucleotides of the target Eco RI site and the underlined case letters represent the mutated nucleotides. The resulting plasmid was designated pBK3.

```
Forward primer:
                                  (SEQ ID NO: 15)
5'-GGGTACCCCAAGGGCgTattcTGCAGATGGG-3'

Reverse primer:
                                  (SEQ ID NO: 16)
5'-CCCATCTGCAgaatAcGCCCTTGGGGTACCC-3'
```

The resulting hpt gene without the Eco RI site was PCR amplified from pBK3 using forward and reverse primers shown below.

```
Forward primer:
                                  (SEQ ID NO: 17)
5'-GGggtaccTTCATTTAAACGGCTTCAC-3'

Reverse primer:
                                  (SEQ ID NO: 18)
5'-GGggtaccCGACCAGCAGACGGCCC-3'
```

The underlined portions represent introduced Kpn I sites for cloning.

Portions of the *Aspergillus oryzae* pyrG gene were used to generate direct repeats and were PCR amplified from pSO2 (WO 98/12300) using the following primers:

```
Repeat 1:
Forward primer:
                                  (SEQ ID NO: 19)
5'-TCCcccgggTCTCTGGTACTCTTCGATC-3'

Reverse primer:
                                  (SEQ ID NO: 20)
5'-GGggtaccCGACCAGCAGACGGCCC-3'

Repeat 2:
Forward primer:
                                  (SEQ ID NO: 21)
5'-GGggtaccTCTCTGGTACTCTTCGATC-3'

Reverse primer:
                                  (SEQ ID NO: 22)
5'-TCCcccgggCGACCAGCAGACGGCCC-3'
```

The underlined portions represent introduced restriction sites Sma I (cccggg) or Kpn I (ggtacc) for cloning.

The three fragments (hpt, repeat #1 and repeat #2) were amplified in separate reactions (50 µl each) composed of 1× ThermoPol reaction buffer, 200 µM dNTPs, 0.25 µM each primer, 50 ng of template DNA, and 1 unit of VENT® DNA polymerase. The amplification reaction was performed using a ROBOCYCLER® programmed for 1 cycle at 95° C. for 2 minutes; 30 cycles each at 95° C. for 1 minute, 61° C. for 1 minute, and 72° C. for 2 minutes; and 1 cycle at 72° C. for 7 minutes.

The PCR products were separated by 1.5% agarose gel electrophoresis in TAE buffer. The approximately 2 kb amplified hpt fragment and the approximately 0.2 kb repeat fragments were excised from the gels and extracted using a MINELUTE® Gel Extraction Kit (QIAGEN Inc., Valencia, Calif., USA). The two pyrG repeat fragments were digested with Kpn I, dephosphorylated with calf intestine phosphatase (New England Biolabs Inc., Ipswich, Mass., USA), and treated with a MINELUTE® Reaction Cleanup Kit (QIAGEN Inc., Valencia, Calif., USA) according to the manufacturer's instructions. The fragments harboring repeat #1 and hpt were then ligated together using a QUICK LIGATION™ Kit (New England Biolabs Inc., Ipswich, Mass., USA) according to the manufacturer's instructions, and treated with a MINELUTE® Reaction Cleanup Kit, and the resulting ligation cloned into pCR®II Blunt using a TOPO® Blunt Cloning Kit. Sequence analysis confirmed one clone in which repeat #1 and the hpt fragment were ligated together in pCR®II Blunt. This plasmid was designated pEmY18.

In order to clone the second repeat into pEmY18, pEmy18 was digested with Eco RV and the digestion purified by 1% agarose gel electrophoresis in TAE buffer. A 5.6 kb fragment was excised from the gel and extracted using a QIAQUICK® Gel Extraction Kit. The 0.2 kb Repeat 2 fragment (described above) and digested pEmY18 were ligated together using a QUICK LIGATION™ Kit. The ligation mixture was used to transform SOLOPACK® Gold Supercompetent Cells (Stratagene, La Jolla, Calif., USA). Sequence analysis identified a plasmid in which the three components (repeat #1, hpt and repeat #2) were in the desired order and orientation and lacked PCR errors. The resulting plasmid was designated pEmY20.

Figure 2:
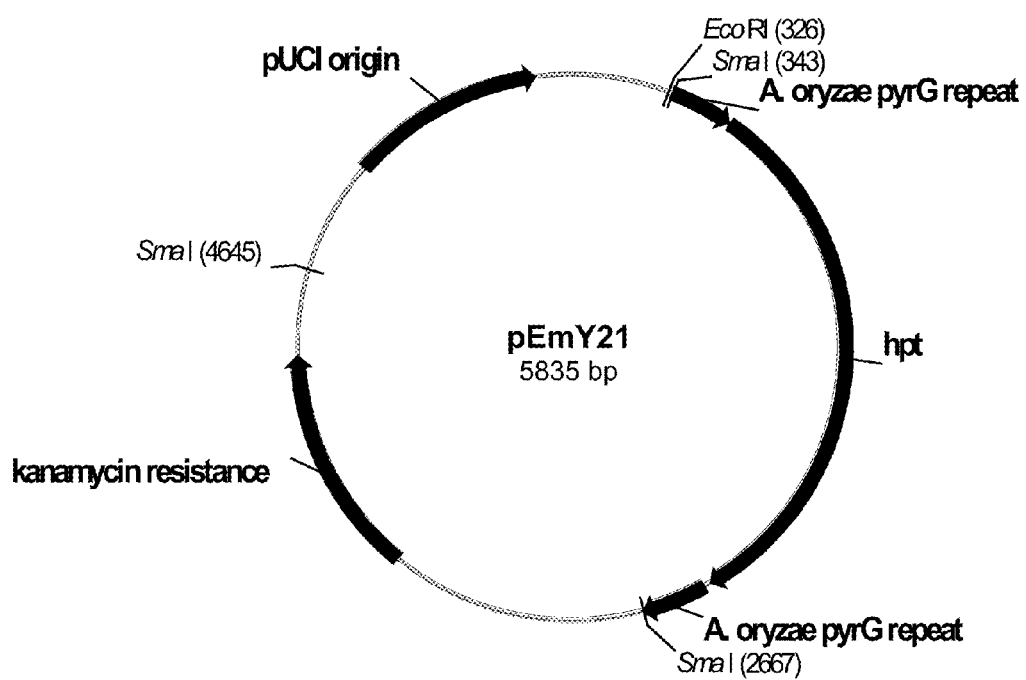
FIG. 2 shows a restriction map of pEmY21.

To insure that subsequent digestion of pEmY20 with Eco RI would liberate a single fragment, an Eco RI site was removed using a QUIKCHANGE® Site-Directed Mutagenesis Kit according to the manufacturer's instructions and forward and reverse primers shown below. The resulting plasmid was designated pEmY21 (FIG. 2) after sequence verification.

```
Forward primer:
                                        (SEQ ID NO: 23)
5'-GGGTACCCCAAGGGCQTATTCTGCAGATGGG-3'

Reverse primer:
                                        (SEQ ID NO: 24)
5'-CCCATCTGCAGAATACGCCCTTGGGGTACCC-3'
```

Example 3

Construction of Plasmid pEmY23

Figure 3:
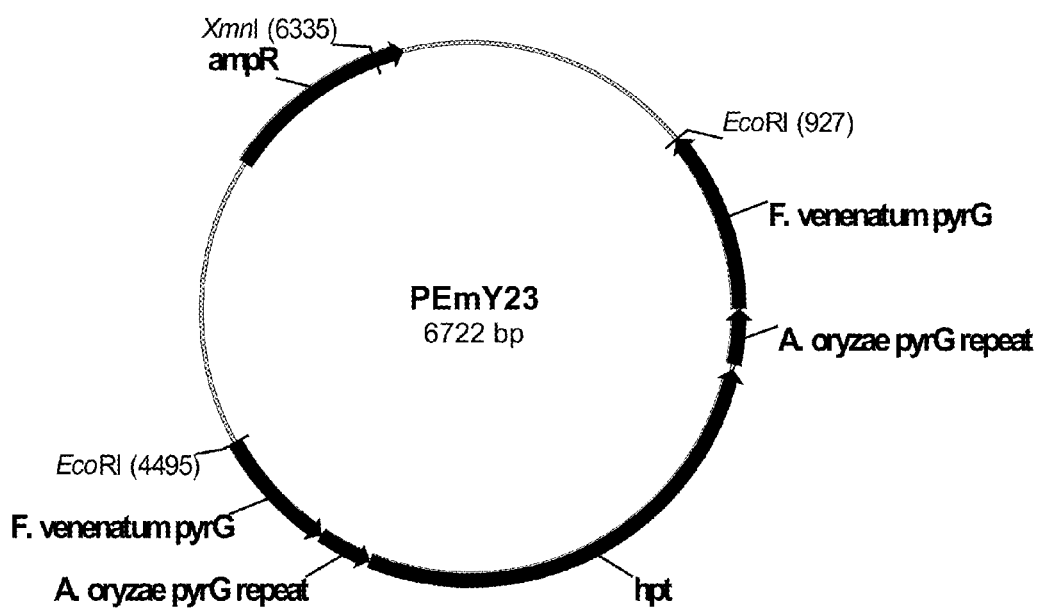
FIG. 3 shows a restriction map of pEmY23.

The *Fusarium venenatum* pyrG coding sequence (2,678 bp) was excised from pDM156.2 (Example 1) by digestion with Eco RV and Stu I restriction endonucleases, and the remaining 4,398 bp vector was gel-purified using a QIAQUICK® Gel Extraction Kit according to the manufacturer's directions. The Sma I fragment of pEmY21 was isolated and gel-purified using a QIAQUICK® Gel Extraction Kit and the two gel-purified fragments were ligated together. They were screened for insert orientation, sequenced for the absence of errors, and one of the clones with the correct insert sequence was selected and designated pEmY23 (FIG. 3).

Example 4

Construction of Plasmid pWTY1470-19-07

Plasmid pJRoy40 (U.S. Pat. No. 7,332,341), which harbors 5' and 3' flanking sequences of a *Fusarium venenatum* trichodiene synthase (tri5) gene (SEQ ID NO: 25 for the DNA sequence and SEQ ID NO: 26 for the deduced amino acid sequence), was used as template for amplification of a portion of the 5' tri5 gene flanking sequence. The PCR reaction contained 200 µM dNTPs, 1× Taq DNA polymerase buffer, 125 pg of pJRoy40 DNA, 50 pmol of each primer shown below, and 1 unit of Taq DNA polymerase in a final volume of 50 µl.

```
Forward primer:
                                        (SEQ ID NO: 27)
5'-GGGAGATCTTCGTTATCTGTGCC-3'

Reverse primer:
                                        (SEQ ID NO: 28)
5'-GGGAGATCTTAGTAGTCGGCATTTGAAAC-3'
```

(Underlined Nucleotides Indicate Introduced Bgl II Sites).

The amplification reaction was incubated in a ROBOCYCLER® programmed for 1 cycle at 95° C. for 3 minutes; 10 cycles each at 95° C. for 30 seconds, 52° C. for 45 seconds, and 7° C. for 2 minutes; 20 cycles each at 95° C. for 30 seconds, 52° C. for 45 seconds, and 72° C. for 5 minutes; and 1 cycle at 72° C. for 7 minutes.

PCR products were separated by 1.5% agarose gel electrophoresis using TBE buffer. A fragment of approximately 600 bp was excised from the gel and extracted using a MINELUTE® Gel Extraction Kit. The fragment was inserted into pCR®2.1 (Invitrogen, Carlsbad, Calif., USA) using a TOPO® TA Cloning Kit (Invitrogen, Carlsbad, Calif., USA) and ONE SHOT® TOP10 competent cells were transformed with 2 µl of the TOPO® TA cloning reaction. Plasmid DNA from eight of the resulting transformants was digested with Eco RI and Bgl II in separate reactions and the inserts for three transformants with the correct restriction digestion patterns were confirmed by DNA sequencing. One clone with the desired sequence was selected and designated pWTY1470-09-05.

A 608 bp Bgl II fragment harboring the tri5 gene 5' repeat was liberated from pWTY1470-09-05 by digestion with Bgl II, purified by 1.0% agarose gel electrophoresis using TBE buffer, excised from the gel, and extracted using a MINELUTE® Gel Extraction Kit.

Figure 4:
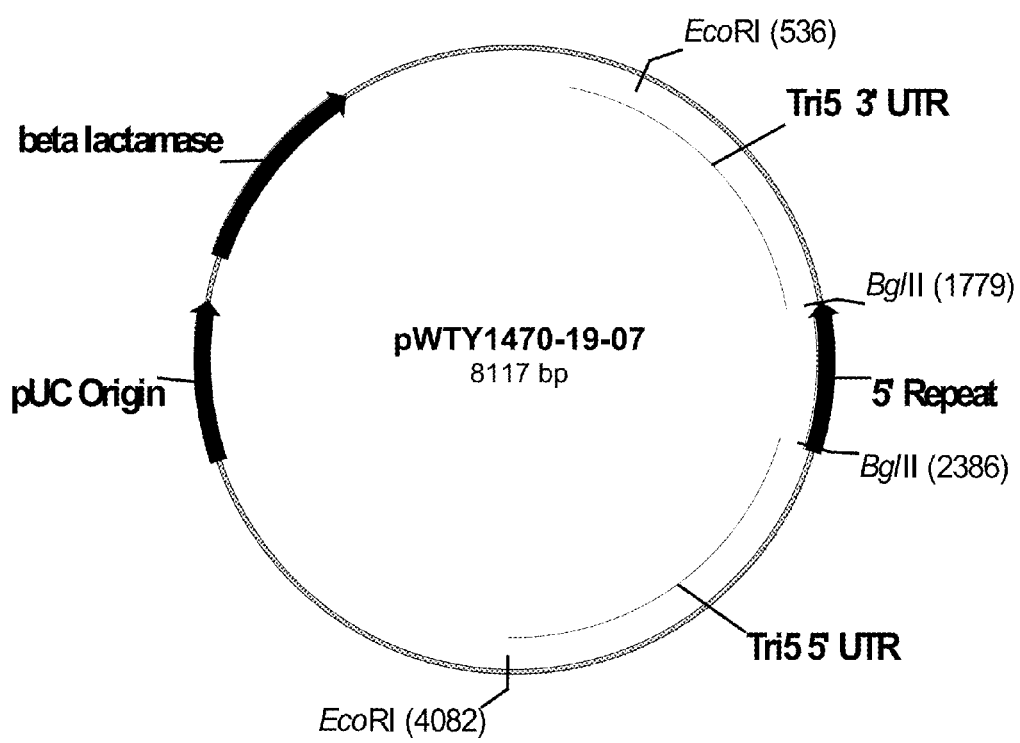
FIG. 4 shows a restriction map of pWTY1470-19-07.

Plasmid pJRoy40 was linearized by digestion with Bgl II, after which it was dephosphorylated using shrimp alkaline phosphatase (Roche Diagnostics Corporation, Indianapolis, Ind., USA) according to the manufacturer's instructions, and purified using a QIAQUICK® PCR Purification Kit (QIAGEN Inc., Valencia, Calif., USA). Linearized pJRoy40 and the gel-purified Bgl II fragment were ligated together using T4 DNA ligase (New England Biolabs Inc., Ipswich, Mass., USA) according to the manufacturer's instructions. Transformation of *E. coli* SURE® chemically competent cells (Stratagene, La Jolla, Calif., USA) was performed according to the manufacturer's directions. One transformant was confirmed by DNA sequencing to contain the desired vector, i.e., harboring the tri5 5' and 3' flanking sequences and a repeat of a portion of the 5' flanking sequence. The resulting plasmid was designated pWTY1470-19-07 (FIG. 4).

Example 5

Construction of Plasmid pWTY1515-02-01

Plasmid pWTY1470-19-07 was subjected to in vitro mutagenesis using a QUIKCHANGE® Site-Directed Mutagenesis Kit according to the manufacturer's instructions and forward and reverse primers shown below.

```
Forward primer:
                                        (SEQ ID NO: 29)
5'-CAAGTAACAGACGCGACAGCTTGCAAAATCTTCGTTATCTGTG-3'

Reverse primer:
                                        (SEQ ID NO: 30)
5'-CACAGATAACGAAGATTTTGCAAGCTGTCGCGTCTGTTACTTG-3'
```

The mutagenesis removed the Bgl II site at 1779 bp and rendered the Bgl II site at 2386 bp unique and usable in subsequent manipulations to insert fragments harboring thymidine kinase (tk) and hygromycin phosphotransferase (hpt) gene cassettes. The mutagenesis reaction was used to transform the kit-supplied *E. coli* XL10-GOLD® Ultra-competent cells (Stratagene, La Jolla, Calif., USA) according to the manufacturer's suggested protocol.

Figure 5:
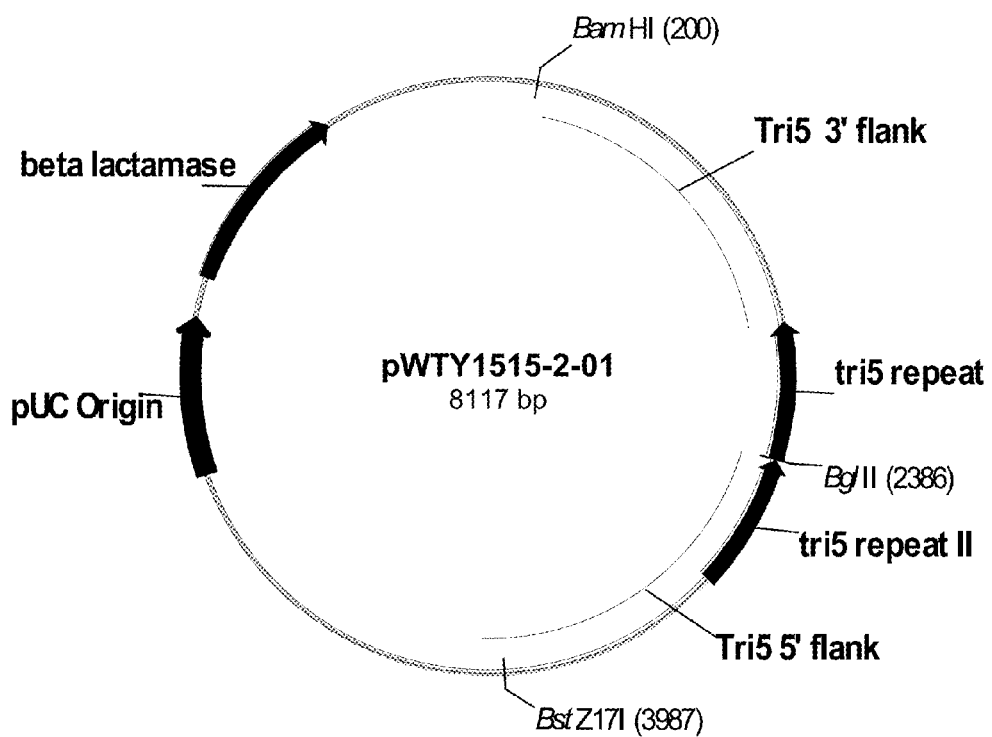
FIG. 5 shows a restriction map of pWTY1515-2-01.

One transformant harboring the mutations indicated above, as verified by sequence analysis, was designated pWTY1515-2-01 (FIG. 5) and used as the backbone in Example 8.

Example 6

Construction of Plasmid pJaL574

Figure 6:
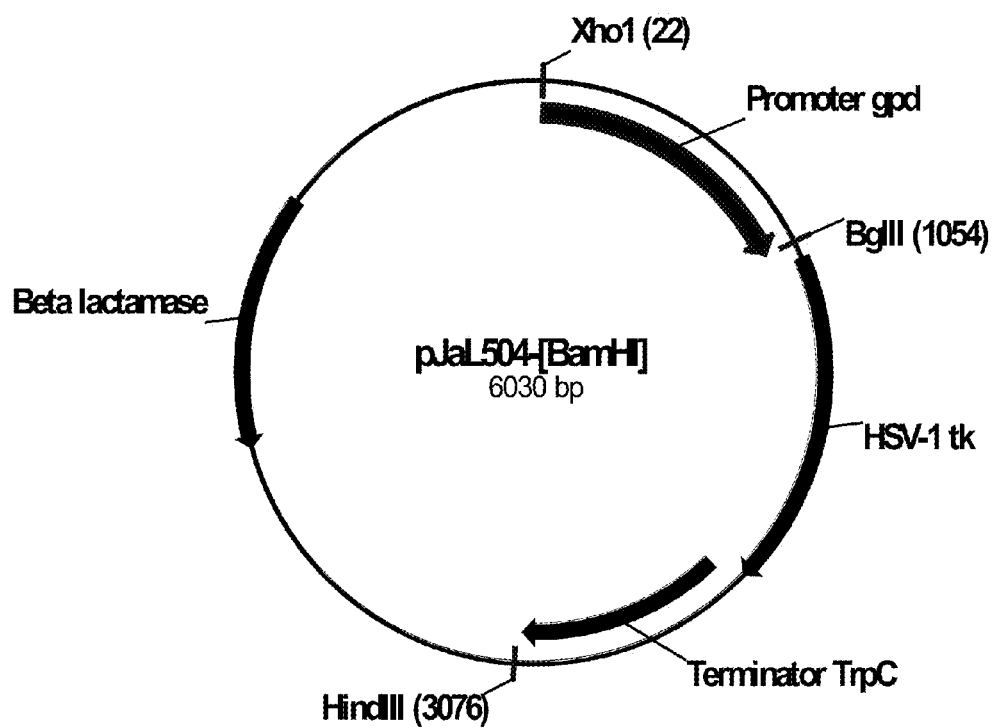
FIG. 6 shows a restriction map of pJaL504-[Bam HI].

Plasmid pDV8 (U.S. Pat. No. 6,806,062) harbors the Herpes simplex virus type 1 thymidine kinase (HSV1-TK; tk) gene (SEQ ID NO: 31 for the DNA sequence and SEQ ID NO: 32 for the deduced amino acid sequence) as a 1.2 kb Bgl II/Bam HI fragment inserted between a 1.0 kb Xho I/Bgl II fragment of the *Aspergillus nidulans* glyceraldehyde-3-phosphate dehydrogenase (gpdA) promoter and a 1.8 kb Bam HI/Hind III fragment harboring the tri-functional *Aspergillus nidulans* indoleglycerolphosphate synthase, phosphoribosylanthranilate isomerase, and glutamine amidotransferase (trpC) transcriptional terminator. Plasmid pDV8 was digested with Bam HI, extracted with phenol-chloroform, ethanol precipitated, and then filled in using Klenow polymerase (Stratagene, La Jolla, Calif., USA). The digested plasmid was re-ligated using a QUICK LIGATION™ Kit following the manufacturer's protocol, treated with a MINELUTE® Gel Extraction Kit, and the resulting ligation products cloned into pCR®4Blunt-TOPO® (Invitrogen, Carlsbad, Calif., USA) using a TOPO® Blunt Cloning Kit according to the manufacturer's instructions. The cloning reaction was transformed into ONE SHOT® chemically competent TOP10 cells according to the manufacturer's directions. Plasmid DNA was extracted from eight of the resulting transformants using a BIOROBOT® 9600 (QIAGEN Inc, Valencia, Calif., USA) and screened by restriction digestion using Xho I/Bam HI and Xho I/Hind III. DNA sequencing of plasmid DNA from two transformants with the correct restriction digestion pattern confirmed that both harbored the desired sequence. One was named pJaL504-[Bam HI] (FIG. 6).

Figure 7:
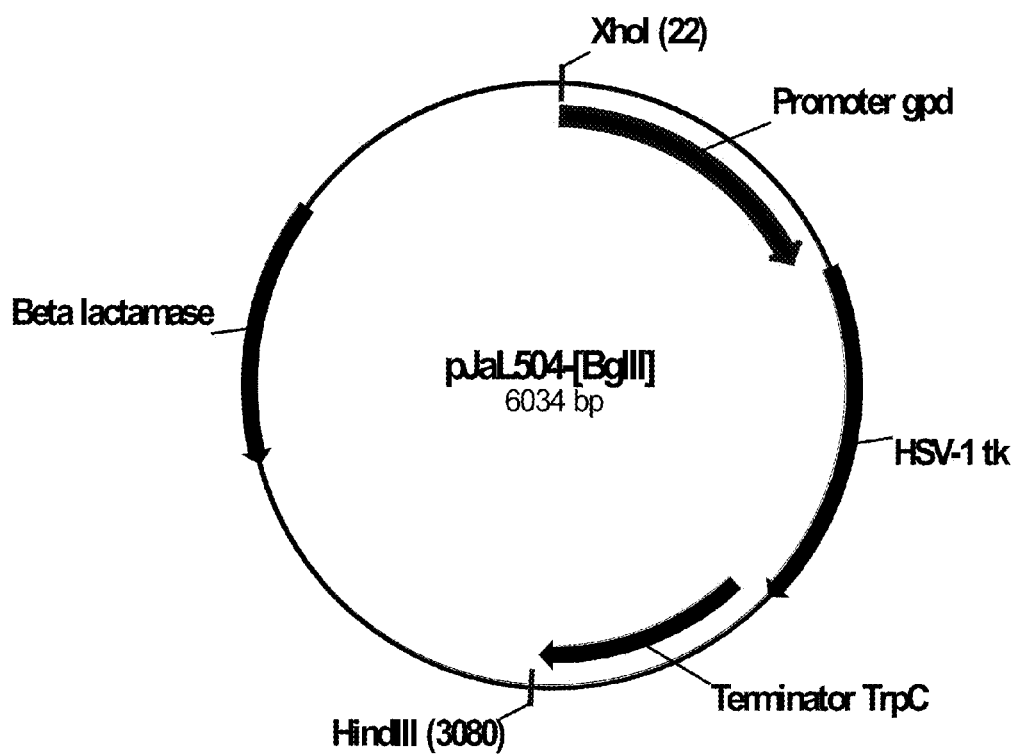
FIG. 7 shows a restriction map of pJaL504-[Bgl II].

Plasmid pJaL504-[Bam HI] was digested with Bgl II, extracted with phenol-chloroform, ethanol precipitated, and then filled in using Klenow polymerase. The digested plasmid was re-ligated using a QUICK LIGATION™ Kit following the manufacturer's protocol, treated with a MINELUTE® Reaction Cleanup Kit, and the resulting ligation cloned into pCR®4Blunt-TOPO® using a TOPO® Blunt Cloning Kit according to the manufacturer's instructions. The cloning reaction was transformed into ONE SHOT® chemically competent E. coli TOP10 cells according to the manufacturer's directions. Plasmid DNA was extracted from eight of the resulting transformants using a BIOROBOT® 9600 and screened by restriction digestion using Xho I/Bgl II and Xho I/Hind III. DNA sequencing of plasmid DNA from two transformants with the correct restriction digestion pattern confirmed that both harbored the desired sequence. One was named pJaL504-[Bgl II] (FIG. 7). Punt et al. (1990, Gene 3: 101-109) have previously shown that 364 bp of the Aspergillus nidulans gpdA promoter could be deleted without affecting the strength of the promoter. Based on these authors' observations, primer #172450 shown below was designed to truncate the Aspergillus nidulans gpdA promoter and reduce the size of the vector.

```
Primer 172450:
                                          (SEQ ID NO: 33)
5'-GACGAATTCTCTAGAAGATCTCTCGAGGAGCTCAAGCTTCTGTACA

GTGACCGGTGACTC-3'
```

The underlined sequence corresponds to gpdA promoter sequence. The remaining sequence is a handle harboring the following restriction sites: Eco RI, Xba I, Bgl II, Xho I, and Hind III.

For truncating the Aspergillus nidulans trpC terminator (again to reduce vector size), primer #172499, shown below, was designed harboring an Eco RI handle.

```
    Primer 172499:
                                          (SEQ ID NO: 34)
       5'-GACGAATTCCGATGAATGTGTGTCCTG-3'
```

The underlined sequence corresponds to the trpC terminator sequence. Amplification using primers 172499 and 172450 truncates the promoter by 364 bp and the trpC terminator sequence by 239 bp.

PCR was performed with the above two primers using pJaL504-[Bgl II] as template to generate a 2,522 bp fragment composed of a truncated version of the A. nidulans gpdA promoter, the coding sequence of the HSV1-TK gene, and a truncated version of the A. nidulans trpC terminator.

The amplification reaction consisted of 5 µl of 10× Buffer (Promega Corporation, Madison, Wis., USA), 0.4 µl of 25 mM dNTPs, 1.25 µl of primer 172450 (100 ng/µl), 1.25 µl of primer 172499 (100 ng/µl), 0.5 µl of pJaL504-[Bgl II] (100 ng/µl), 2 µl of Pfu DNA polymerase (Promega Corporation, Madison, Wis., USA) (2.5 U/µl), and 39.6 µl of sterile distilled water. The amplification reaction was incubated in a ROBOCYCLER® programmed for 1 cycle at 95° C. for 45 seconds; and 28 cycles each at 95° C. for 45 seconds, 57° C. for 45 seconds, and 72° C. for 5 minutes. A final extension was performed at 72° C. for 10 minutes at 72° C.

Figure 8:
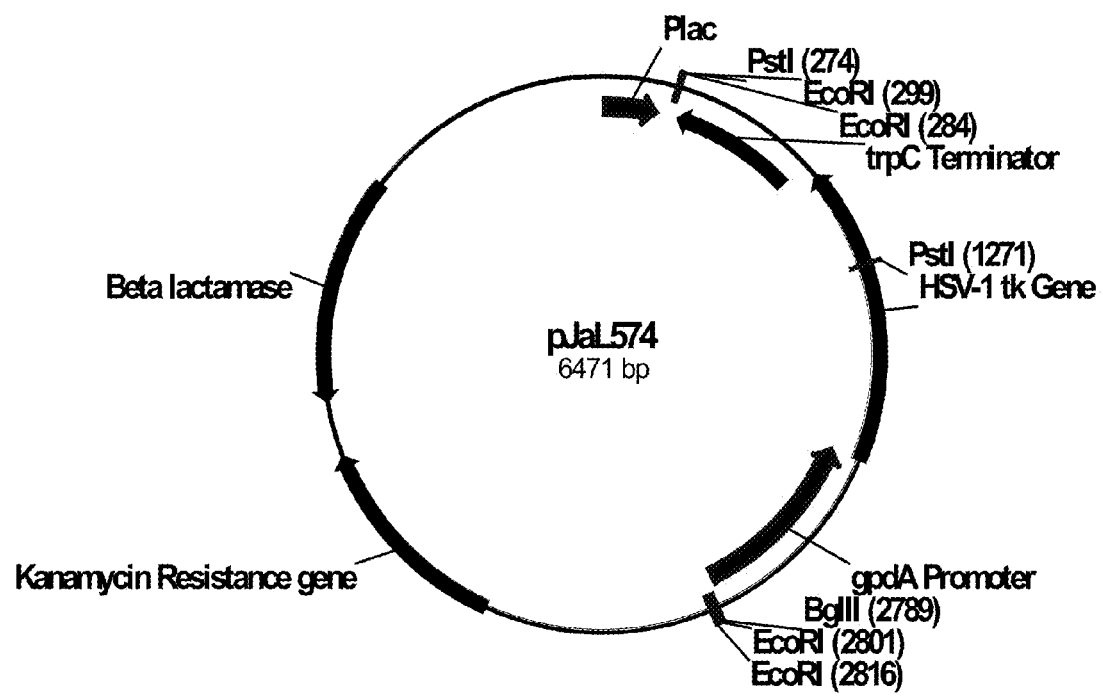
FIG. 8 shows a restriction map of pJaL574.

The amplification reaction was subjected to 1% agarose gel electrophoresis using low melting temperature agarose in 50 mM Tris-50 mM boric acid-1 mM disodium EDTA (TBE) buffer. A 2,522 bp fragment was excised from the gel and extracted using a QIAQUICK® Gel Extraction Kit. The gel-purified DNA was then inserted into pCR®4Blunt-TOPO® using a TOPO® Blunt Cloning Kit according to the manufacturer's instructions. The cloning reaction was transformed into ONE SHOT® chemically competent TOP10 cells according to the manufacturer's directions. Plasmid DNA was extracted from eight of the resulting transformants using a BIOROBOT® 9600 and screened by restriction digestion using Eco RI and Bgl II. DNA sequencing of plasmid DNA from two transformants with the correct restriction digestion pattern confirmed that both harbored the desired sequence. One was designated pJaL574 (FIG. 8).

Example 7

Construction of Plasmid pWTY1449-02-01

Figure 9:
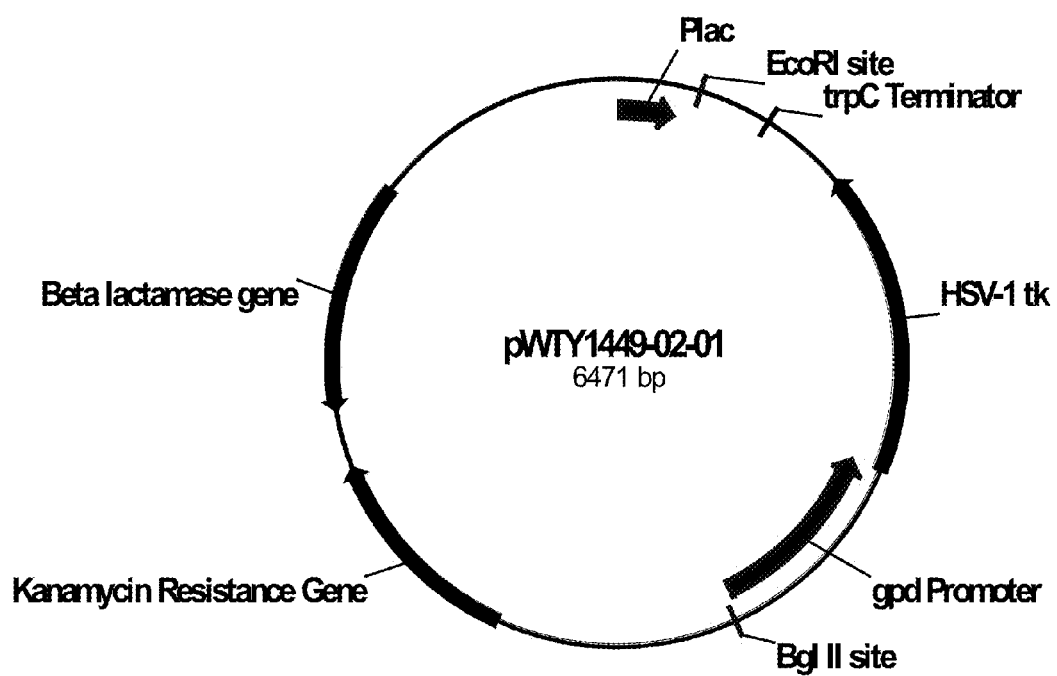
FIG. 9 shows a restriction map of pWTY1449-02-01.

Plasmid pJaL574 was transformed into competent E. coli SCS110 cells (Stratagene, La Jolla, Calif., USA) following the manufacturer's recommended protocol. Plasmid DNA was extracted from twenty-four of the resulting transformants using a BIOROBOT® 9600, and then subjected to analytical digestion using Eco RI and Bgl II. Subsequent DNA sequence analysis resulted in the identification of a clone with the correct sequence, which was designated pWTY1449-02-01 (FIG. 9).

Example 8

Generation of the Tris Deletion Vector pJfyS1579-21-16

An E. coli hygromycin phosphotransferase (hpt) gene cassette was PCR amplified from plasmid pEmY23 using an ADVANTAGE® GC Genomic PCR Kit (Clontech, Palo Alto, Calif., USA) and gene-specific forward and reverse primers shown below. The underlined portion in the reverse primer is a Bgl II site for cloning.

```
Forward primer:
                                          (SEQ ID NO: 35)
5'-TTGAACTCTCAGATCCCTTCATTTAAACGGCTTCACGGGC-3'

Reverse primer:
                                          (SEQ ID NO: 36)
5'-CAGATAACGAAGATCTACGCCCTTGGGGTACCCAATATTC-3'
```

The amplification reaction contained 362 ng of pEmY23 as DNA template, 200 μm dNTP's, 1.1 mM magnesium acetate, 0.4 μM primers, 1×GC Reaction Buffer (Clontech, Palo Alto, Calif., USA), 0.5 M GC Melt (Clontech, Palo Alto, Calif., USA), and 1×GC Genomic Polymerase Mix (Clontech, Palo Alto, Calif., USA) in a final volume of 50 μl. The amplification reaction was incubated in an EPPENDORF® MASTERCYCLER® (Eppendorf, Munich, Germany) programmed for 1 cycle at 95° C. for 2 minutes; 25 cycles each at 94° C. for 30 seconds and 66° C. for 3 minutes; and 1 cycle at 66° C. for 3 minutes; and hold at 4° C.

Figure 10:
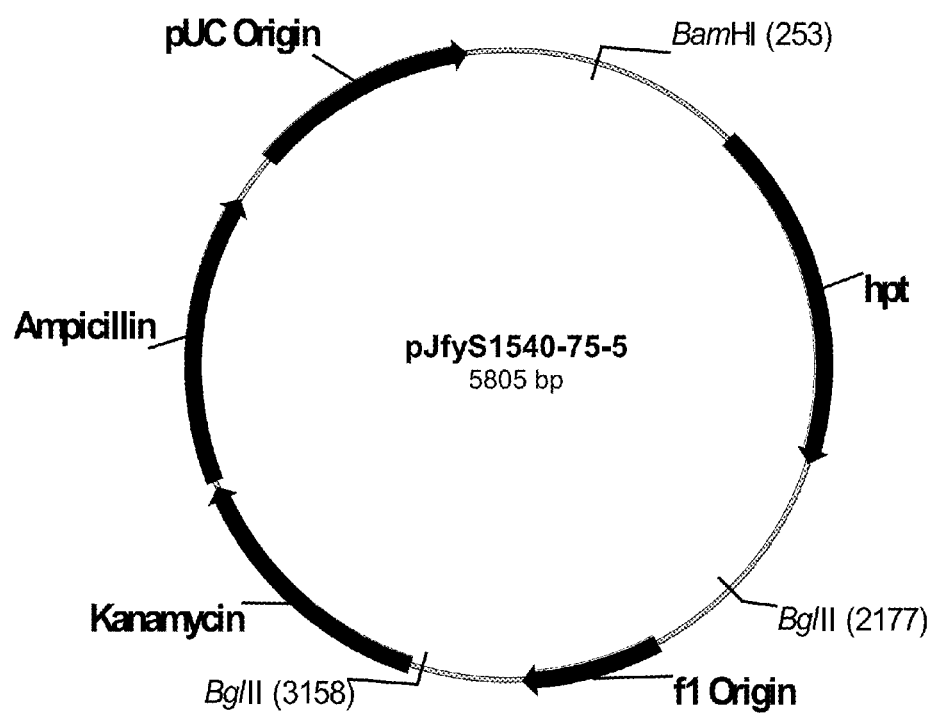
FIG. 10 shows a restriction map of pJfyS1540-75-5.

PCR products were separated by 1% agarose gel electrophoresis using TAE buffer. A fragment of approximately 1.9 kb was excised from the gel and extracted using a MINIELUTE® Gel Extraction Kit. The fragment was cloned into pCR®2.1 using a TOPO® TA Cloning Kit according to the manufacturer's instructions. ONE SHOT® TOP10 competent cells were transformed with 2 μl of the TOPO® TA reaction. Sequence analysis of plasmid DNA from 8 transformants confirmed that there were no deviations from the expected sequence and the plasmid was designated pJfyS1540-75-5 (FIG. 10).

Figure 11:
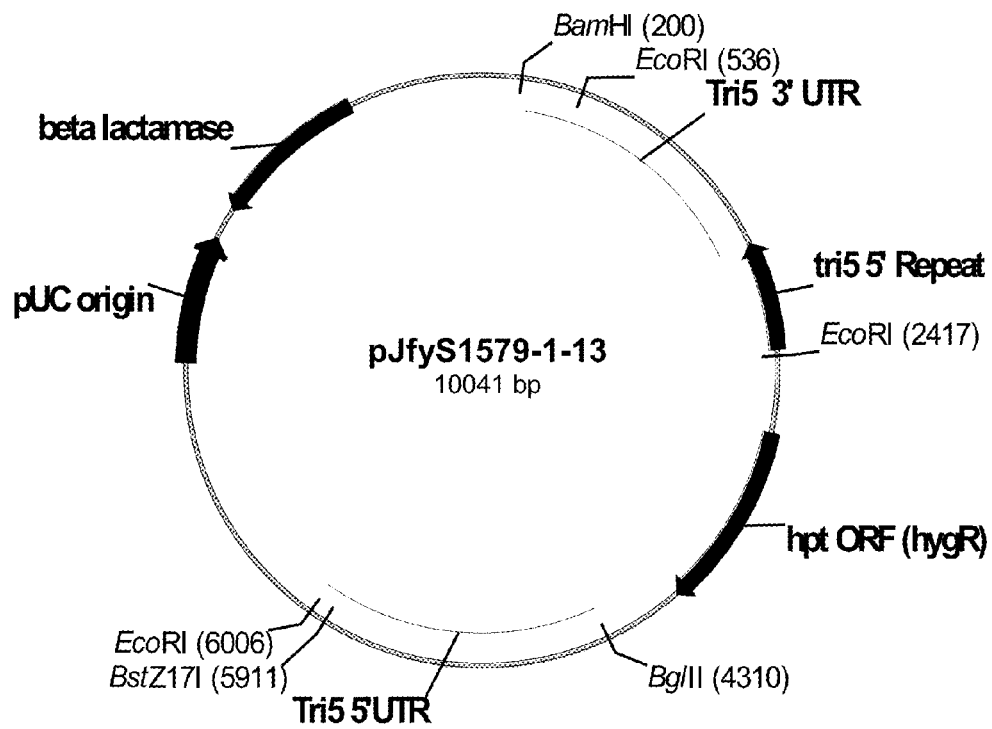
FIG. 11 shows a restriction map of pJfyS1579-1-13.

The hpt insert was liberated from pJfyS1540-75-5 by digestion with Bam HI and Bgl II and purified by 1% agarose gel electrophoresis in TAE buffer. A fragment of 1.9 kb was excised and extracted using a MINIELUTE® Gel Extraction Kit. A Rapid DNA Ligation Kit was used to ligate the fragment to Bgl II-linearized empty tri5 deletion vector pWTY1515-2-01 (Example 5) which had been dephosphorylated using calf intestine phosphatase. E. coli SURE® chemically competent cells were transformed with the ligation reaction and plasmid DNA from 24 of the resulting transformants was analyzed by restriction digestion with Eco RI to confirm the orientation of the insert. One of the transformants harboring the insert in the desired orientation was selected and designated pJfyS1579-1-13 (FIG. 11).

A Herpes simplex virus thymidine kinase (tk) gene (SEQ ID NO: 31 for the DNA sequence and SEQ ID NO: 32 for the deduced amino acid sequence) was PCR amplified using pWTY1449-02-01 as template and gene specific forward and reverse primers shown below. The bold sequence represents the introduced Bgl II site.

Forward primer:
(SEQ ID NO: 37)
5'-GCCGACTACTAGATCGACCGGTGACTCTTTCTGGCATGCG-3'

Reverse primer:
(SEQ ID NO: 38)
5'-CAGATAACGAAGATCTGAGAGTTCAAGGAAGAAACAGTG-3'

The amplification reaction contained 1× HERCULASE® reaction buffer (Stratagene, La Jolla, Calif., USA), 200 μM dNTPs, 55 ng of pWTY1449-02-01, 0.2 μM primers, 2% DMSO, and 2.5 units of HERCULASE® DNA polymerase (Stratagene, La Jolla, Calif., USA) in a final volume of 50 μl. The amplification reaction was incubated in an EPPENDORF® MASTERCYCLER® programmed for 1 cycle at 95° C. for 1 minute; 25 cycles each at 94° C. for 30 seconds, 60° C. for 30 seconds, and 68° C. for 2 minutes and 45 seconds; and 1 cycle at 68° C. for 2 minutes and 45 seconds; and a hold at 4° C.

Figure 12:
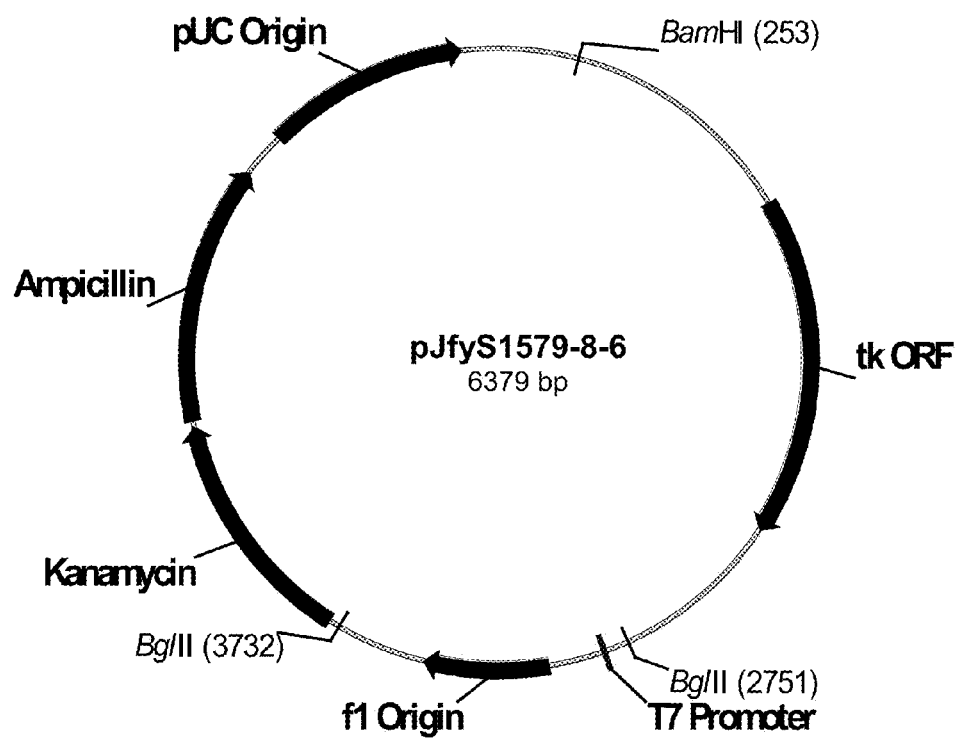
FIG. 12 shows a restriction map of pJfyS1579-8-6.

PCR products were separated by 1% agarose gel electrophoresis using TAE buffer. A fragment of approximately 2.8 kb was excised from the gel and purified using a MINIELUTE® Gel Extraction Kit. The fragment was cloned into pCR®2.1 using a TOPO® TA Cloning Kit. ONE SHOT® TOP10 competent cells were transformed with 2 μl of the TOPO® TA reaction. Sequence analysis of plasmid DNA from one of the transformants identified a mutation in the tk coding sequence (C1621 G) resulting in an amino acid change of glycine to alanine. This mutation was corrected using a QUIKCHANGE® II XL Site-Directed Mutagenesis Kit (Stratagene, La Jolla, Calif., USA) according to the manufacturer's instructions and forward and reverse primers shown below. The lower case letter indicates the desired change. Sequence analysis of 16 clones resulted in the selection of one which was designated pJfyS1579-8-6 (FIG. 12).

Forward primer:
5'-CCCTGTTTCGGGgCCCCGAGTTGCTGG-3'  (SEQ ID NO: 39)

Reverse primer:
5'-CCAGCAACTCGGGGcCCCGAAACAGGG-3'  (SEQ ID NO: 40)

Figure 13:
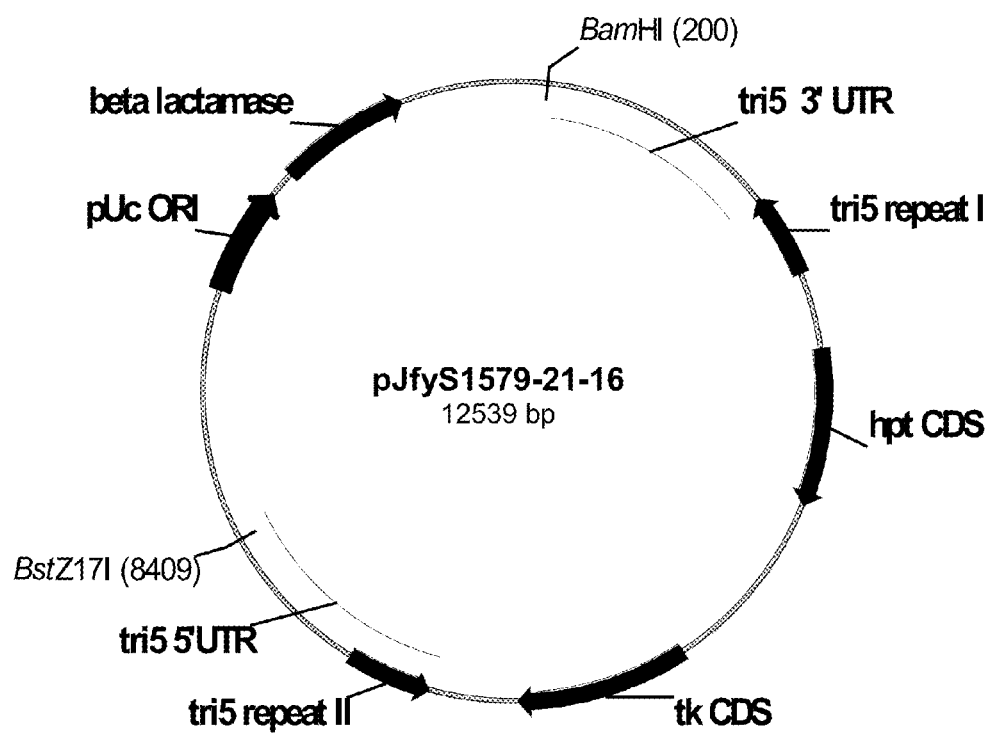
FIG. 13 shows a restriction map of pJfyS1579-21-16.

Plasmid pJfyS1579-8-6 was digested with Bam HI and Bgl II to liberate the 2.8 kb tk fragment and the fragment was purified as described above. This fragment was ligated to pJfyS1579-1-13, which had been linearized with Bgl II and treated with calf intestine phosphatase, using a QUICK LIGATION™ Kit and used to transform E. coli SURE® chemically competent cells according to the manufacturer's protocol. The resulting plasmid was designated pJfyS1579-21-16 (FIG. 13) and used as the tri5 deletion cassette.

Example 9

Construction of a Universal Deletion Vector Harboring the Thymidine Kinase (tk) Negative Selection Marker and Hygromycin Phosphotransferase (hpt) Positive Selection Marker A universal deletion vector harboring both the thymidine kinase (tk) and hygromycin phosphotransferase (hpt) markers was constructed to facilitate assembly of subsequent deletion plasmids. Flanking sequences for 5' and 3' regions of the gene targeted for deletion can be easily ligated to the vector following digestion of the latter with Pme I or Asc I (for 5' flanking sequences) and Sbf I or Swa I (for 3' flanking sequences).

In order to PCR amplify the direct repeats derived from the 5' flanking region of the *Fusarium venenatum* pyrG gene, 50 picomoles of the primers shown below were used in two PCR reactions containing 50 ng of pDM156.2, 1×Pfx Amplification Buffer (Invitrogen, Carlsbad, Calif., USA), 6 μl of a 10 mM blend of dNTPs, 2.5 units of PLATINUM® Pfx DNA polymerase (Invitrogen, Carlsbad, Calif., USA), and 1 μl of 50 mM MgSO₄ in a total volume of 50 μl.
Primers:

Repeat #1
Sense Primer:
(SEQ ID NO: 41)
5'-GTTTAAACGGCGCGCC CGACAAAACAAGGCTACTGCAGGCAGG-3'
Antisense Primer:
(SEQ ID NO: 42)
5'-TTGTCGCCCGGG AATACTCCAACTAGGCCTTG-3'

Repeat #2
Sense Primer:
(SEQ ID NO: 43)
5'-AGTATTCCCGGG CGACAAAACAAGGCTACTGCA-3'
Antisense Primer:
(SEQ ID NO: 44)
5'-ATTTAAATCCTGCAGG AATACTCCAACTAGGCCTTG-3'

The amplification reactions were incubated in an EPPENDORF® MASTERCYCLER® programmed as follows. For repeat #1: 1 cycle at 98° C. for 2 minutes; and 5 cycles each at 94° C. for 30 seconds, 55° C. for 30 seconds, and 68° C. for 1 minute. This was followed by 35 cycles each at 94° C. for 30 seconds, 59° C. for 30 seconds, and 68° C. for 1 minute. For repeat #2 the cycling parameters were: 1 cycle at 98° C. for 2 minutes; and 5 cycles each at 94° C. for 30 seconds, 55° C. for 30 seconds, and 68° C. for 1 minute. This was followed by 35 cycles each at 94° C. for 30 seconds, 56° C. for 30 seconds, and 68° C. for 1 minute. After the 35 cycles both reactions (i.e., repeats #1 and #2) were incubated at 68° C. for 10 minutes and then cooled at 10° C. until being further processed.

PCR products from both reactions were separated by 0.8% GTG-agarose (Cambrex Bioproducts, East Rutherford, N.J., USA) gel electrophoresis using TAE buffer. For repeat #1 and repeat #2, fragments of approximately 0.26 kb were excised from the gels and purified using Ultrafree®-DA spin cups (Millipore, Billerica, Mass., USA) according to the manufacturer's instructions. Ten microliters of each purified repeat were then used in a single overlapping PCR reaction containing 1×Pfx Amplification Buffer, 6 μl of a 10 mM blend of dATP, dTTP, dGTP, and dCTP, 2.5 units of PLATINUM® Pfx DNA polymerase, and 1 μl of 50 mM MgSO$_4$ in a total volume of 50 μl. The amplification reaction was incubated in an EPPENDORF® MASTERCYCLER® programmed for 1 cycle at 98° C. for 2 minutes; and 5 cycles each at 94° C. for 30 seconds, 50° C. for 30 seconds, and 68° C. for 1 minute. The reaction was then mixed with a pre-warmed solution containing 50 picomoles of the sense primer for repeat #1 and 50 picomoles of the anti-sense primer for repeat #2, 1×Pfx Amplification Buffer, 6 μl of a 10 mM dNTPs, 2.5 units of PLATINUM® Pfx DNA polymerase, and 1 μl of 50 mM MgSO$_4$ in a final volume of 50 μl.

The new 100 μl amplification reaction was incubated in an EPPENDORF® MASTERCYCLER® programmed for 35 cycles each at 94° C. for 30 seconds, 58° C. for 30 seconds, and 68° C. for 1 minute. After 35 cycles, the reaction was incubated at 68° C. for 10 minutes and then cooled at 10° C. until being further processed. A 0.5 kb PCR product (harboring the repeat assembly) was isolated by 0.8% GTG-agarose gel electrophoresis as described above.

Figure 14:
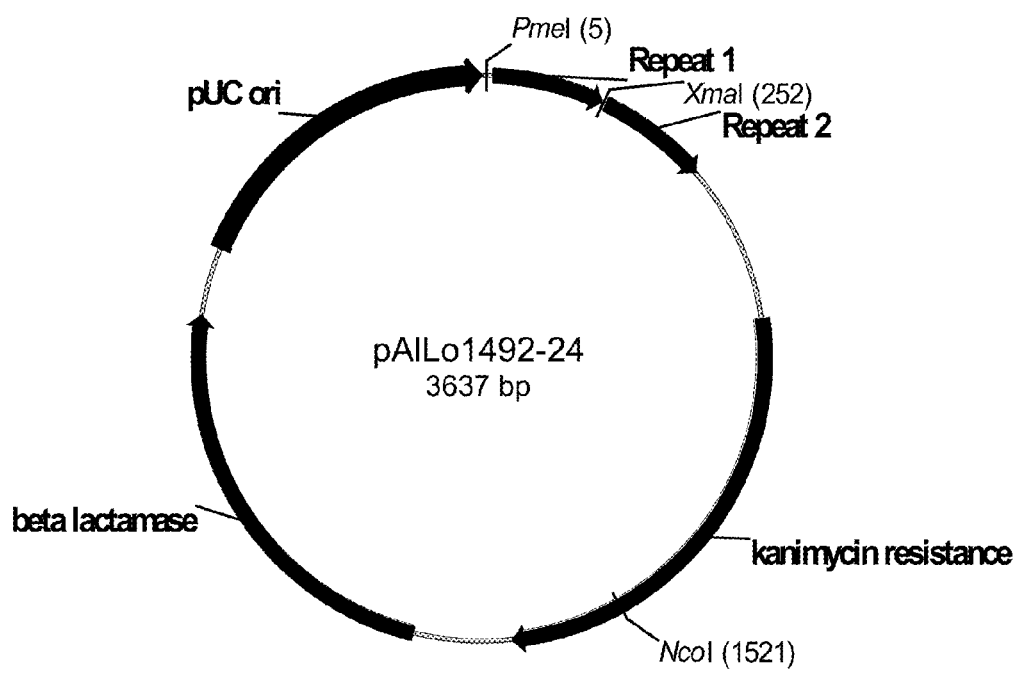
FIG. 14 shows a restriction map of pAILo1492-24.

Plasmid pCR4 (Invitrogen, Carlsbad, Calif., USA) was used as the source of the vector backbone for the construction of the universal deletion vector. To remove the non-essential portions of the pCR4 DNA, 2.5 μg of plasmid pTter61C (WO 2005/074647) were digested sequentially with Bsp LU11 I and Bst XI. The digested vector was then treated with Antarctic phosphatase (New England Biolabs Inc., Ipswich, Mass., USA). The 3.1 kb digested backbone was isolated by 0.8% GTG-agarose gel electrophoresis as described above. The purified repeat assembly was then ligated to the purified vector backbone with a Rapid Ligation Kit (Roche Diagnostics Corporation, Indianapolis, Ind., USA). The ligation reaction consisted of: 75 ng of purified vector backbone and 3 μl of the purified repeat assembly. One microliter of this ligation reaction was used to transform chemically competent SOLOPACK® Supercompetent cells (Stratagene, Carlsbad, Calif., USA) using the manufacturer's protocol. Twenty-four transformants were analyzed by Nco I/Pme I restriction digestion. Twenty-three out of twenty four transformants had the expected restriction digestion pattern. Clone pFvRs #10 was selected at random for sequencing to confirm that there were no PCR-induced errors. Sequencing analysis showed that the repeat assembly in clone pFvRs #10 had the expected sequence, and was designated pAILo1492-24 (FIG. 14).

The cassette harboring the hygromycin phosphotransferase (hpt) gene was PCR amplified from pEmY23 using the gene-specific forward and reverse primers shown below. The underlined sequence represents a Xma I site and the bold letters represent a Bgl II site. The four "a"s at each 5' end allow for subsequent digestion of the terminal ends of the PCR product.

```
Forward primer:
                                      (SEQ ID NO: 45)
5'-aaaacccgggCCTTCATTTAAACGGCTTCACGGGC-3'

Reverse primer:
                                      (SEQ ID NO: 46)
5'-aaaacccgggAGATCTACGCCCTTGGGGTACCCAATATTC-3'
```

The amplification reaction contained 60 ng of pEmY23, 200 μm dNTPs, 1 mM magnesium acetate, 0.4 μM primers, 1×Pfx Amplification Buffer, 0.5 M GC Melt, and 2.5 units of PLATINUM® Pfx DNA polymerase in a final volume of 50 μl. The reaction was incubated in an EPPENDORF® MASTERCYCLER® programmed for 1 cycle at 95° C. for 2 minutes; 10 cycles each at 94° C. for 30 seconds, 60° C. for 30 seconds, and 68° C. for 1 minute 50 seconds; and 1 cycle at 68° C. for 7 minutes followed by holding at 4° C.

Figure 15:
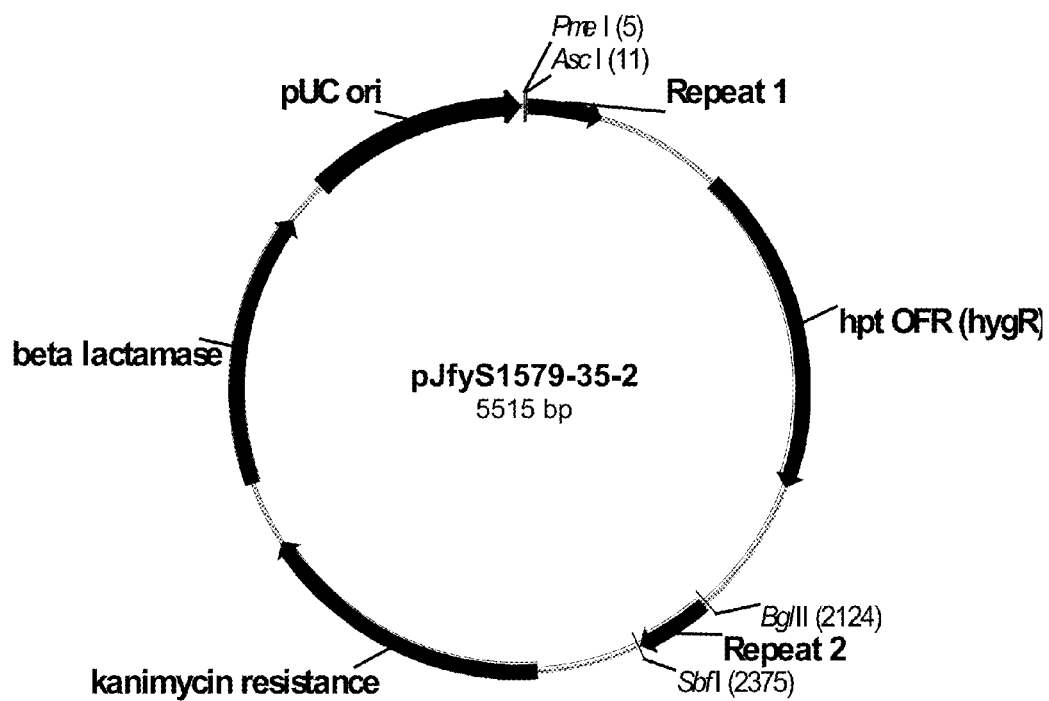
FIG. 15 shows a restriction map of pJfyS1579-35-2.

PCR products were separated by 1% agarose gel electrophoresis using TAE buffer. A fragment of approximately 1.8 kb was excised from the gel and extracted using a MINIELUTE® Gel Extraction Kit. The gel-purified PCR product was subsequently digested with Xma I and run on a 1% agarose gel and gel-purified again as above. A QUICK LIGATION™ Kit was used to ligate the hpt PCR product to Xma I-linearized pAILo1492-24, which had been treated with calf intestine phosphatase. The resulting plasmid was designated pJfyS1579-35-2 (FIG. 15) and was used as the recipient for the insertion of the thymidine kinase gene.

Figure 16:
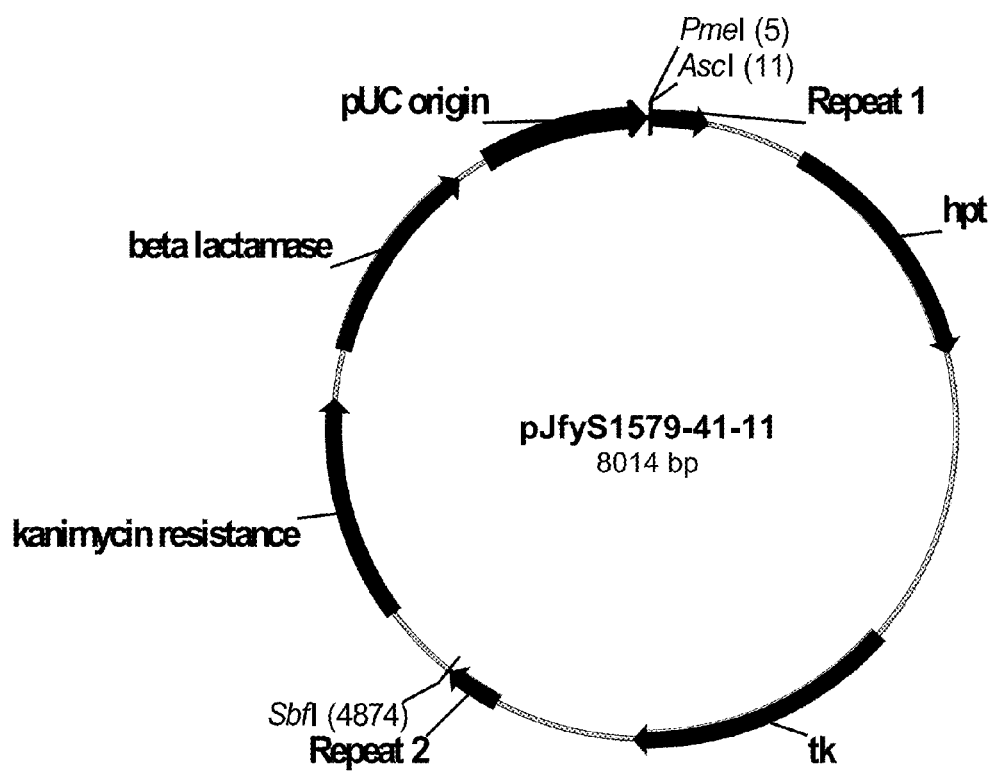
FIG. 16 shows a restriction map of pJfyS1579-41-11.

The source of the Herpes simplex virus tk cassette was plasmid pJfyS1579-8-6 (Example 8), from which the insert was liberated by digestion with Bam HI and Bgl II. The digestion products were separated by 1% agarose gel electrophoresis using TAE buffer, and a fragment corresponding to the 2.8 kb tk gene insert was excised and extracted using a MINELUTE® Gel Extraction Kit. A QUICK LIGATION™ Kit was used to ligate the tk gene cassette to Bgl II-linearized pJfyS1579-35-2, which had been treated with calf intestine phosphatase. The resulting plasmid was designated pJfyS1579-41-11 (FIG. 16).

Example 10

Trichoderma reesei Strain 981-O-8 Genomic DNA Extraction

Trichoderma reesei strain 981-O-8 was grown in 50 ml of YEG medium in a baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

Example 11

Construction of Trichoderma reesei Subtilisin-Like Serine Protease Gene Deletion Plasmid pDAtw18

To construct a Trichoderma reesei subtilisin-like serine protease gene deletion cassette, a 1.4 kb fragment of the downstream non-coding region of the *Trichoderma reesei* subtilisin-like serine protease gene (SEQ ID NO: 1 for the DNA sequence and SEQ ID NO: 2 for the deduced amino acid sequence) was PCR amplified using oligonucleotides 067375 and 067376 shown below.

```
Primer 067375:
                                   (SEQ ID NO: 47)
5'-AAAAAACCTGCAGGGATGTAAGAGGGTTTCTTGAGGGGT-3'

Primer 067376:
                                   (SEQ ID NO: 48)
5'-AAAAAACCTGCAGGGCGGCCGCTGATAGTAGACATGATACTG-3'
```

Underlined letters represent a Sbf I site added to the sense and antisense primers to facilitate cloning of the amplified fragment and the bold region represents a Not I site introduced for later restriction digestion to remove a β-lactamase gene for fungal transformation.

The amplification reaction was composed of 300 ng of the *Trichoderma reesei* strain 981-O-8 genomic DNA (Example 10), 300 μM dNTPs, 50 pmol of primer 067375, 50 pmol of primer 067376, 1× reaction buffer, 1 mM MgSO$_4$ and 2.5 units of PLATINUM® Pfx DNA polymerase (Invitrogen Corp., Carlsbad, Calif., USA). The reaction was incubated in an EPPENDORF® MASTERCYCLER® 5333 (Eppendorf Scientific, Inc., Westbury, N.Y., USA) programmed for 1 cycle at 98° C. for 5 minutes; 30 cycles each at 98° C. for 30 seconds, 58° C. for 30 seconds, and 72° C. for 1.6 minutes; and 1 cycle at 72° C. for 15 minutes. A 1442 bp PCR fragment was isolated by 1% agarose gel electrophoresis using TAE buffer, excised from the gel, and extracted using a MINELUTE® Gel Extraction Kit. The 1442 bp PCR product was cloned into pCR®2.1 TOPO® (Invitrogen Corp., Carlsbad, Calif., USA) and transformed into Chemically Competent *E. coli* cells according to the manufacturer's instructions. Transformants were selected on 2×YT agar plates supplemented with 100 μg of ampicillin per ml and incubated at 37° C. for 16 hours. The DNA sequence of the cloned fragment was verified by DNA sequencing with M13 forward and reverse primers. The resulting plasmid was designated pClone10.

Similarly, a 1.5 kb fragment of the upstream non-coding region of the *Trichoderma reesei* subtilisin-like serine protease gene (SEQ ID NO: 1 for the DNA sequence and SEQ ID NO: 2 for the deduced amino acid sequence) was PCR amplified using primers 067377 and 067374 shown below.

```
Primer 067377:
                                   (SEQ ID NO: 40)
5'-AAAAAAGGCGCGCCGCGGCCGCAATGGATAGCTAATAATCAA-3'

Primer 067374:
                                   (SEQ ID NO: 50)
5'-AAAAAAGGCGCGCCACTGTGGGAGGGCTGTATGGACA-3'
```

Underlined letters represent an Asc I site added to the sense and antisense primers to facilitate the cloning of the amplified fragment and the bold region represents a Not I site The PCR amplification was performed under the same conditions described above except primers 067377 and 067374 were used. A 1530 bp PCR fragment was isolated by 1% agarose gel electrophoresis using TAE buffer, excised from the gel, and extracted using a MINELUTE® Gel Extraction Kit. The 1530 bp amplified fragment was cloned into pCR®2.1 TOPO® vector and transformed into Chemically Competent *E. coli* cells according to the manufacturer's instructions. Transformants were selected on 2×YT agar plates supplemented with 100 μg of ampicillin per ml and incubated at 37° C. for 16 hours. The DNA sequence of the cloned fragment was verified by DNA sequencing with M13 forward and reverse primers. The resulting plasmid was designated pClone1.

Plasmid pClone1 was digested with Asc I and the digestion purified by 1% agarose gel electrophoresis in TAE buffer. A 1415 bp fragment containing the upstream non-coding region of the *Trichoderma reesei* subtilisin-like serine protease gene fragment was excised from the gel and extracted using a MINELUTE® Gel Extraction Kit. This insert was ligated to Asc I digested and calf intestinal phosphatase (CIP) dephosphorylated pJfyS1579-41-11 (Example 9) using a QUICK LIGATION™ Kit (New England Biolabs, Beverly, Mass., USA) according to the manufacturer's suggested protocol. Restriction analysis was used to identify transformants containing the insert in the desired orientation and sequence analysis was performed to confirm the absence of PCR errors. The resulting plasmid was designated pClone14.

Figure 17:
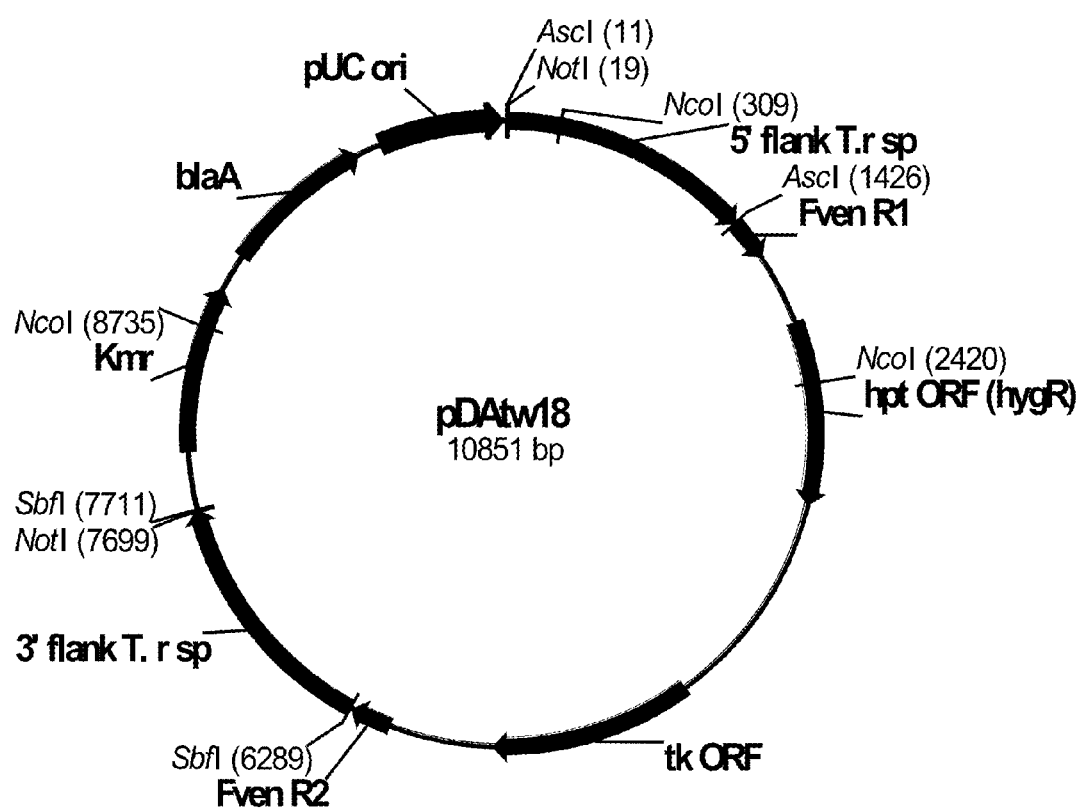
FIG. 17 shows a restriction map of pDAtw18.

The final *Trichoderma reesei* subtilisin-like serine protease gene deletion cassette, pDAtw18 (FIG. 17), was created by digesting pClone10 with Sbf I to release the 1.5 kb downstream non-coding region of the *Trichoderma reesei* subtilisin-like serine protease gene fragment, which was then ligated to Sbf I digested and calf intestinal phosphatase (CIP) dephosphorylated pClone14 using a QUICK LIGATION™ Kit according to the manufacturer's suggested protocol. A linear 7.7 kb fragment containing the TrSpΔ::hpt/tk allele could then be generated by digestion with Not I.

Example 12

*Trichoderma reesei* Protoplast Generation and Transformation

Protoplast preparation and transformation were performed using a modified protocol by Penttila et al., 1987, *Gene* 61: 155-164. Briefly, *Trichoderma reesei* strain 981-O-8 was cultivated in 25 ml of YP medium supplemented with 2% (w/v) glucose and 10 mM uridine at 27° C. for 17 hours with gentle agitation at 90 rpm. Mycelia were collected by filtration using a Millipore Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes NS, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended to a final concentration of 1×10$^8$ protoplasts/ml in STC. Excess protoplasts were stored in a Cryo 1° C. Freezing Container (Nalgene, Rochester, N.Y., USA) at −80° C.

Approximately 10 mg of each of the deletion cassettes described in the following examples were digested with either Not I (Examples 13 and 20) or Hind III/Bgl II (Example 17). Each digestion reaction was purified by 1% agarose gel electrophoresis in TAE buffer, a DNA band was excised from the gel, and extracted using a QIAQUICK® Gel Extraction Kit. The resulting purified DNA was added to 100 μl of the protoplast solution and mixed gently. PEG buffer (250 μl) was added, mixed, and incubated at 34° C. for 30 minutes. STC (3 ml) was then added, mixed, and plated onto PDA medium supplemented with 1 M sucrose. After incubation at 28° C. for 16 hours, 15 ml of an overlay PDA medium supplemented with 100 μg of hygromycin B per ml was added to each plate. The plates were incubated at 28° C. for 4-6 days.

Example 13

Generation of Subtilisin-Like Serine Protease Gene Deletion *Trichoderma reesei* Strain DAtw18-97

*Trichoderma reesei* strain 981-O-8 protoplasts were transformed with Not I-linearized pDAtw18 using the method described in Example 12 to delete the subtilisin-like serine protease gene. One hundred and sixty-six transformants were selected on PDA plates containing 25 μg of hygromycin B per ml. The transformants were sub-cultured to PDA plates to generate spores. Each transformant was cultured in a 125 ml baffled shake flask containing 25 ml of cellulase-inducing medium at pH 6.0 and incubated at 28° C. for 7 days with agitation at 200 rpm. *Trichoderma reesei* strain 981-O-8 was run as a control. Culture broth samples were removed 7 days post-inoculation, centrifuged at 15,700×g for 5 minutes in a micro-centrifuge, and the supernatants transferred to new tubes.

A protease assay using a synthetic substrate, N-Succinyl-L-Ala-L-Ala-L-Pro-L-Phe-p-nitroanilide (AAPF) (Bachem AG, Bubendorf, Switzerland), was performed on the supernatants above to determine whether any of the transformants were deleted for the subtilisin-like serine protease gene. The substrate was initially dissolved in dimethyl sulfoxide at a concentration of 100 mg/ml. The dissolved substrate was then diluted 50-fold into 100 mM NaCl-100 mM MOPS pH 7.0. The reaction was initiated by adding 10 μl of each transformant supernatant to 100 μl of the diluted substrate in a flat-bottomed 96-well plate (Corning Inc., Acton, Mass., USA). The reaction plate was incubated at 50° C. for 3 hours and then the absorbance at 405 nm was measured using a SPECTRAMAX® Microplate Reader (Molecular Devices, Sunnyvale, Calif., USA). Protease activities of the *Trichoderma reesei* DAtw18 transformants were compared to that of parent strain *Trichoderma reesei* strain 981-O-8.

Fifteen transformants displaying lower extracellular protease activities compared to *Trichoderma reesei* strain 981-O-8 were then analyzed by Southern analysis. Genomic DNA from each of the 15 transformants was extracted as described in Example 11 and 2 μg of each were digested with 20 units of Nco I-HF™ (New England Biolabs, Inc., Ipswich, Mass., USA) for 16 hours at 37° C. Digested DNA was fractionated by 0.7% agarose gel electrophoresis using TAE buffer for 4 hours and blotted onto a NYTRAN™ SuperCharge membrane (Schleicher & Schuell BioScience, Keene, N.H., USA) using a TURBOBLOTTER™ (Schleicher & Schuell BioScience, Keene, N.H., USA) for 16 hours following the manufacturer's recommendations. The membrane was hybridized with a 502 bp digoxigenin-labeled subtilisin-like serine protease gene probe, which was synthesized by incorporation of digoxigenin-11-dUTP by PCR using primers 067911 (sense) and 067912 (antisense) shown below.

```
Primer 067911 (sense):
GCGGTCATTTACAGTGCCTCGAATA    (SEQ ID NO: 51)

Primer 996117 (antisense):
CTGCTCTGTTAGCAATCCTCAAGCA    (SEQ ID NO: 52)
```

The amplification reaction (50 μl) was composed of 1× ThermoPol Reaction Buffer, 5 μl of PCR DIG Labeling Mix, 10 ng of pDAtw18, 0.3 μM primer 067911, 0.3 μM primer 067912, and 2.5 units of Taq DNA polymerase. The reactions were incubated in an EPPENDORF® MASTERCYCLER® 5333 programmed for 30 cycles each at 95° C. for 30 seconds, 56° C. for 30 seconds, and 72° C. for 40 seconds (15 minute final extension). Five microliters of the PCR product was size-selected by 1.5% agarose gel electrophoresis using TAE buffer, stained with ethidium bromide, and visualized under a UV transilluminator. Incorporation of digoxigenin was indicated by increase in molecular mass.

Hybridization was performed in DIG Easy Hyb buffer (Roche Molecular Biochemicals, Indianapolis, Ind., USA) at 42° C. for 17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. Southern analysis indicated that all 15 transformants contained a single integration of the deletion cassette at the subtilisin-like serine protease gene locus without any further integration of the deletion fragment at other loci. One strain designated *Trichoderma reesei* DAtw18-97 was chosen for subsequent transformations.

Example 14

Construction of Plasmid pSaMe-AaXYL

Plasmid pSaMe-AaXYL was constructed to comprise the *Trichoderma reesei* cellobiohydrolase I gene promoter and terminator and the *Aspergillus aculeatus* GH10 xylanase coding sequence.

Cloning of the *Aspergillus aculeatus* xylanase followed the overall expression cloning protocol as outlined in H. Dalbøge et al., 1994, *Mol. Gen. Genet.* 243: 253-260.

RNA was isolated from *Aspergillus aculeatus* CBS 101.43 mycelium. Poly(A)$^+$ RNA was isolated from total RNA by chromatography on oligo(dT)-cellulose. Double-stranded cDNA was synthesized as described by Maniatis et al. (Molecular cloning: a laboratory manual. Cold Spring Harbor Laboratory Press, 1982). After synthesis the cDNA was treated with mung bean nuclease, blunt-ended with T4 DNA polymerase, and ligated to non-palindromic Bst XI adaptors (Invitrogen, Carlsbad, Calif., USA). The cDNA was size fractionated by 1% agarose gel electrophoresis using TAE buffer where fragments ranging from 600 bp to 4000 bp were used in the library construction. The DNA was ligated into Bst XI-digested pYES 2.0 between the GAL1 promoter and the iso-1-cytochrome c terminator and transformed into *Escherichia coli* MC1061 cells (Stratagene, La Jolla, Calif., USA. The library was plated onto LB plates and incubated overnight at 37° C. The colonies were scraped from the plates and resuspended in LB medium supplemented with 100 μg of ampicillin per ml. Plasmid DNA was isolated using a Plasmid Midi Kit (QIAGEN Inc., Valenicia, Calif., USA). The purified plasmid DNA was pooled.

The purified plasmid DNA mixture was transformed into *Saccharomyces cerevisiae* W3124 cells (MATa; ura 3-52; leu 2-3, 112; his 3-D200; pep 4-1137: prc1::HIS3; prb1::LEU2; cir+; van den Hazel et al., 1992, *Eur. J. Biochem.* 207: 277-283). Cultivation, transformation and media were as described by Guthrie et al., 1991, *Meth. Enzymol.* Vol 194, Academic Press. The transformed cells were plated onto synthetic complete agar containing 2% glucose for 3 days at 30° C. After 3 days the colonies were replica plated to SC medium (Sherman, 2002, *Methods Enzymol.* 350: 3-41) with 2% galactose and incubated for 4 days at 30° C. Xylanase expressing colonies were identified by 1% agarose overlay with 0.1% AZCL-Birch-Xylan at pH 4.5 (Dalboge, 2006, *FEMS Microbiology Reviews* 21: 29-42). Colonies expressing xylanase activity were surrounded by a blue zone. Plasmid DNA, rescued from the positive colonies, contained a DNA insert of approximately 1.3 kb. Sequencing of the isolated gene fragment revealed a 1218 bp open reading frame encoding a polypeptide with a theoretical molecular weight of 43.0 kDa. The cDNA fragment was subcloned into the *Aspergillus* expression vector pHD464 (Dalboge and Heldt-Hansen, 1994, *Mol. Gen. Genet.* 243, 253-260) digested with Bam HI and Xho I by cutting the clone with Bam HI and Xho I and isolating the 1.2 kb cDNA insert (Christgau et al., 1996, *Biochem. J.* 319: 705-712) to generate plasmid pA2X2.

The *Aspergillus aculeatus* GH10 xylanase coding sequence was PCR amplified using plasmid pA2x2 as template and primers 153505 and 153506 shown below using standard methods to yield an approximately 1.2 kb fragment. The 1.2 kb fragment was digested with Bam HI and Xho I (introduced in the PCR primers) and cloned into vector pCaHj527 (WO 2004/099228). The resulting plasmid was designated pMT2155 in which the cDNA was under transcriptional control of the neutral amylase II (NA2) promoter from *A. niger* and the AMG terminator from *A. niger*.

```
Primer 153505:
                                     (SEQ ID NO: 53)
5'-TCTTGGATCCACCATGGTCGGACTGCTTTCAATCACC-3'

Primer 153506:
                                     (SEQ ID NO: 54)
5'-TTAACTCGAGTCACAGACACTGCGAGTAATAGTC-3'
```

Two synthetic oligonucleotide primers shown below were designed to PCR amplify the *Aspergillus aculeatus* GH10 gene from plasmid pMT2155 and introduce flanking regions for insertion into expression vector pMJ09 (WO 2005/056772). Bold letters represent coding sequence and the remaining sequence is homologous to the insertion sites of pMJ09.

```
Forward Primer:
                                     (SEQ ID NO: 55)
5'-cggactgcgcaccatggtcggactgctttcaat-3'

Reverse Primer:
                                     (SEQ ID NO: 56)
5'-tcgccacggagcttatcacagacactgcgagtaat-3'
```

The amplification reaction was composed of 50 picomoles of each of the primers above, 50 ng of pMT2155, 1 µl of 10 mM blend of dATP, dTTP, dGTP, and dCTP, 5 µl of 10× ACCUTAQ™ DNA Polymerase Buffer (Sigma-Aldrich, St. Louis, Mo., USA), and 5 units of ACCUTAQ™ DNA Polymerase (Sigma-Aldrich, St. Louis, Mo., USA), in a final volume of 50 µl. An EPPENDORF® MASTERCYCLER® 5333 was used to amplify the DNA fragment programmed for 1 cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

The reaction products were isolated by 1.0% agarose gel electrophoresis using TAE buffer where a 1.2 kb product band was excised from the gel and purified using a QIAQUICK® Gel Extraction Kit according to the manufacturer's instructions.

Figure 18:
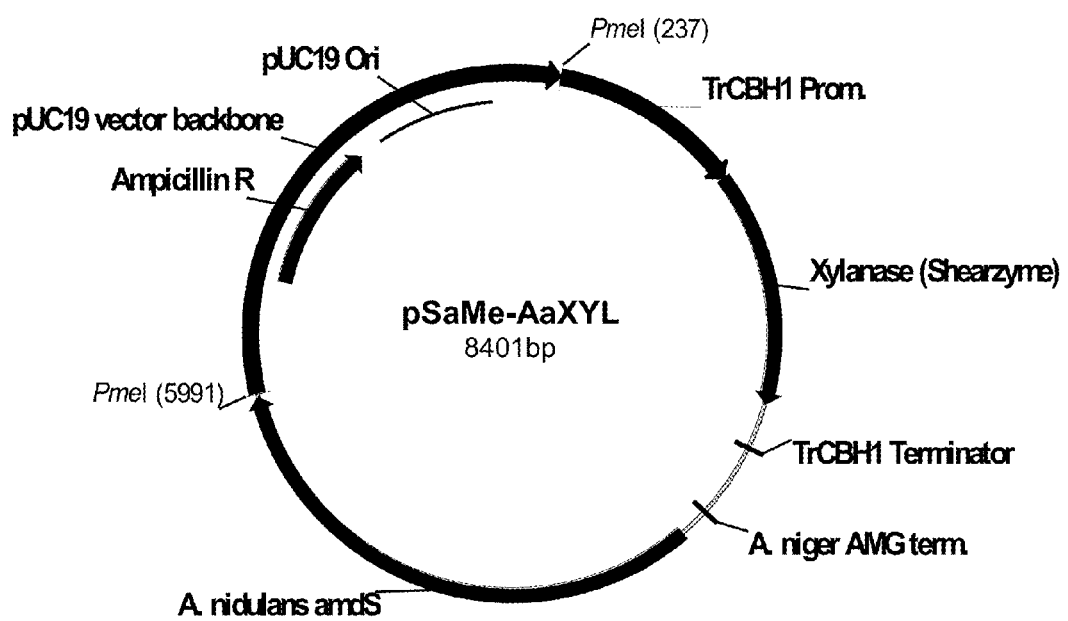
FIG. 18 shows a restriction map of pSaMe-AaXYL.

The fragment was then cloned into pMJ09 using an IN-FUSION™ Cloning Kit (Clontech, Inc., Palo Alto, Calif., USA). The vector was digested with Nco I and Pac I and purified by agarose gel electrophoresis as described above. The 1.2 kb gene fragment and the digested vector were ligated together in a reaction resulting in the expression plasmid pSaMe-AaXYL in which transcription of the Family GH10 gene was under the control of the *T. reesei* cbh1 promoter. The ligation reaction (50 µl) was composed of 1× IN-FUSION™ Buffer (Clontech, Inc., Palo Alto, Calif., USA), 1×BSA, 1 µl of IN-FUSION™ enzyme (diluted 1:10) (Clontech, Inc., Palo Alto, Calif., USA), 100 ng of pAILo2 digested with Nco I and Pac I, and 100 ng of the *Aspergillus aculeatus* GH10 xylanase purified PCR product. The reaction was incubated at room temperature for 30 minutes. One µl of the reaction was used to transform *E. coli* XL10 SOLOPACK® Gold cells (Stratagene, La Jolla, Calif., USA) according to the manufacturer. An *E. coli* transformant containing pSaMe-AaXYL (FIG. 18) was detected by restriction enzyme digestion and plasmid DNA was prepared using a BIOROBOT® 9600. DNA sequencing of the *Aspergillus aculeatus* GH10 gene from pSaMe-AaXYL was performed using dye-terminator chemistry (Giesecke et al., 1992, *Journal of Virology Methods* 38: 47-60) and primer walking strategy.

Example 15

*Aspergillus aculeatus* GH10 Xylanase Expression in Subtilisin-Like Serine Protease Deficient Strain DAtw18-97

Protoplasts were generated from subtilisin-like serine protease deficient strain *Trichoderma reesei* DAtw18-97 according to the procedure described in Example 12 and transformed with *Trichoderma reesei* expression construct pSaMe-AaXYL (Example 14) containing the *Aspergillus aculeatus* GH10 xylanase coding sequence to determine the stability of *A. aculeatus* xylanase GH10 expressed by *T. reesei* DAtw18-97. Transformation was performed by adding approximately 3 µg of Pme I digested and gel-purified pSaMe-AaXYL to 100 µl of protoplast solution and mixing gently. PEG buffer (250 µl) was added, mixed, and incubated at 37° C. for 30 minutes. STC (3 ml) was then added, mixed, and plated onto COVE plates. The plates were incubated at 28° C. for 7-10 days. After a single round of spore purification on COVE2 plates, 20 transformants were grown in small-scale shake flasks containing 25 ml of cellulase-inducing medium for 5 days at 28° C., after which supernatant were collected by centrifugation at 15,700×g for 10 minutes in a micro-centrifuge.

Expression of the *Aspergillus aculeatus* GH10 xylanase was analyzed using 8-16% CRITERION™ Tris-HCl gels (Bio-Rad Laboratories, Hercules, Calif., USA) with a CRITERION™ Cell (Bio-Rad Laboratories, Hercules, Calif., USA). Five µl of day 5 samples were suspended in 2× concentration of Laemmli Sample Buffer (Bio-Rad Laboratories, Hercules, Calif., USA) and heated at 95° C. for 5 minutes in the presence of 5% β-mercaptoethanol. All samples were loaded onto the CRITERION™ Tris-HCl gels and subjected to electrophoresis in 1× Tris/Glycine/SDS running buffer (Bio-Rad Laboratories, Hercules, Calif., USA). The resulting gels were stained with BIO-SAFE™ Coomassie Stain (Bio-Rad Laboratories, Hercules, Calif., USA). SDS-PAGE profiles of the cultures showed the presence of predominately the full-length *Aspergillus aculeatus* GH10 xylanase protein but also a smaller fragment present in lower quantities. The results suggested that deletion of the subtilisin-like serine protease gene for the production of *Aspergillus aculeatus* GH10 xylanase did not completely prevent proteolysis of the protein.

Example 16

Construction of *Trichoderma reesei* Aspartic Protease Gene Deletion Plasmid pAgJg111

The deletion vector pAgJg111 was constructed to disrupt expression of a *Trichoderma reesei* 42 kDa aspartic protease (SEQ ID NO: 3 for the DNA sequence and SEQ ID NO: 4 for the deduced amino acid sequence) in *Trichoderma reesei* strain 981-O-8. Plasmid pAgJg110 was generated first by amplifying the aspartic protease coding region plus and minus 600 bp upstream and downstream of the coding region using primers 066694 (sense) and 066695 (antisense) shown below.

```
Primer 066694 (sense):
ACGAATGGTCAAAGGACTATGTATCAT       (SEQ ID NO: 57)

Primer 066695 (antisense):
CACATACCCAGAGTCAGGCCCTGCG         (SEQ ID NO: 58)
```

The aspartic protease region was amplified by PCR in a reaction composed of 316 ng of *Trichoderma reesei* strain 981-O-8 genomic DNA (Example 10), 1 µl of Herculase II Fusion DNA Polymerase (Stratagene, LaJolla, Calif., USA), 50 pmol of primer 066694, 50 pmol of primer 066695, 5 µl of 10 mM dNTPs, 5 µl of 5× Herculase II reaction buffer (Stratagene, LaJolla, Calif., USA), and 35 µl of water. The reaction was incubated in an EPPENDORF® MASTERCYCLER® 5333 programmed for 1 cycle at 95° C. for 2 minutes; 30 cycles each at 95° C. for 20 seconds, 60° C. for 20 seconds, and 72° C. for 1 minute 30 seconds; 1 cycle at 72° C. for 3 minutes; and a 4° C. hold. A 2.5 kb PCR fragment was purified by 1% agarose gel electrophoresis using TAE buffer, excised from the gel, and extracted using a QIAQUICK® Gel Extraction Kit according to the manufacturer's instructions.

The gel purified PCR fragment was treated with Taq DNA polymerase to add 3' A-overhangs to the fragment in a reaction composed of 5 µl of the purified PCR fragment, 1 µl of the 10× Thermopol Buffer (New England Biolabs, Inc, Ipswich, Mass., USA), 0.5 µl of 10 mM dNTPs, 0.5 µl of Taq DNA polymerase, and 3 µl of water. The reaction was incubated at 72° C. for 15 minutes. The aspartic protease gene fragment was cloned into pCR®2.1-TOPO® according to the manufacturer's instruction to generate pAgJg110. The cloning reaction was composed of 2 µl of the aspartic protease PCR fragment, 1 µl of Salt Solution (Invitrogen, Carlsbad, Calif., USA), 2 µl of water, and 1 µl of pCR®2.1-TOPO®.

To construct plasmid pAgJg111, pAgJg110 was digested with Bmg I and BstE II in a reaction composed of 5 µg of pAgJg110 DNA, 3 µl of Bmg I, 3 µl of BstE II, 10 µl 10×NEB Buffer 3 (New England Biolabs, Inc, Ipswich, Mass., USA), 1 µl 100×BSA, and 53 µl of water. The digestion of pAgJg110 was incubated at 37° C. for 1 hour, and then at 60° C. for 1 hour. The digested pAgJg110 was then blunt ended by adding 10 µl of 10 mM dNTPs, and 12.5 units of DNA Polymerase I, Large (Klenow) Fragment (New England Biolabs, Inc, Ipswich, Mass., USA). The reaction was incubated at 37° C. for 15 minutes. The digested blunt ended pAgJg110 was purified by 1% agarose gel electrophoresis using TAE buffer, excised from the gel, and extracted using a QIAQUICK® Gel Extraction Kit according to the manufacturer's instructions.

Plasmid pHT (Cummings et al., 1999, *Current Genetics* 36: 371-382) was digested with Hind III and Ava I in a reaction composed of 1.86 µg of pHT DNA, 3 µl of Hind III, 3 µl of Ava I, 10 µl of 10×NEB Buffer 2 (New England Biolabs, Inc, Ipswich, Mass., USA), and 51 µl of water at 37° C. for 2.5 hours and then blunt ended by adding 10 µl of 10 mM dNTPs and 12.5 µl units of DNA Polymerase I, Large (Klenow) Fragment and incubating at 37° C. for 15 minutes. The digested blunt ended pHT was purified by 1% agarose gel electrophoresis using TAE buffer and a 1.9 kb fragment was excised from the gel and extracted using a QIAQUICK® Gel Extraction Kit according to the manufacturer's instructions.

Figure 19:
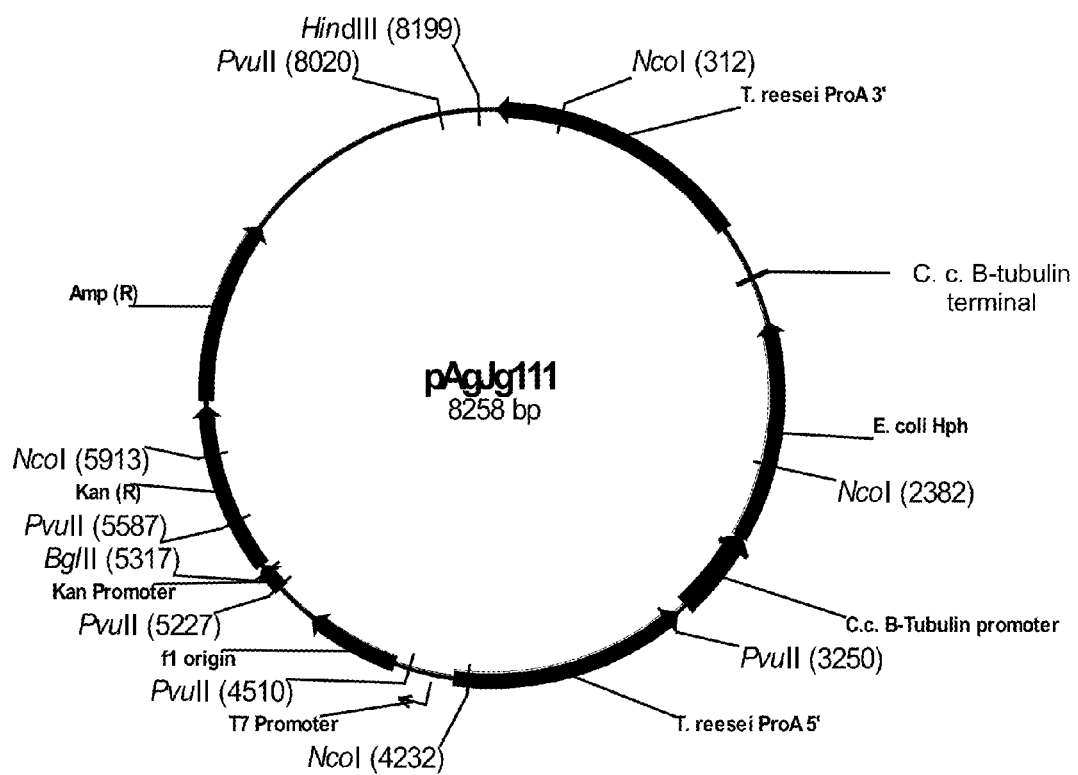
FIG. 19 shows a restriction map of pAgJg111.

The resulting fragments from pAgJg110 and pHT were ligated together to form pAgJg111 (FIG. 19) using T4 DNA Ligase in reaction composed of 88 ng of pHT fragment, 106 ng of pAgJg110 fragment, 1.5 µl of 10×T4 DNA Ligase Buffer (New England Biolabs, Inc, Ipswich, Mass., USA), 1 µl of T4 DNA Ligase (New England Biolabs, Inc, Ipswich, Mass., USA), and 0.5 µl of water.

Example 17

Generation of Aspartic Protease Gene Deletion *Trichoderma reesei* Strain AgJg111-50

*Trichoderma reesei* strain 981-O-8 protoplasts were transformed with Hind III/Bgl I-linearized pAgJg111 using the method described in Example 12 to delete the aspartic protease gene. Ninety transformants were selected on PDA plates containing 25 µg of hygromycin B per ml. The transformants were sub-cultured to PDA plates to generate spores.

Possible candidates of *Trichoderma reesei* strain 981-O-8 containing the pAgJg111 deletion vector in the aspartic protease locus, thereby disrupting the expression of the aspartic protease, were screened by Fungal Colony PCR using a modified protocol of Suzuki et al., 2006, *J. Bioscience and Bioengineering* 102: 572-574. A small amount of spores from each candidate was suspended in 25 µl of TE buffer and heated on high in a microwave oven for 1 minute. The microwaved spore suspension was used as a template in a PCR reaction to screen for the aspartic protease deletion. The reaction was composed of 1 µl of the spore suspension, 1 µl of 10 mM dNTPs, 12.5 µl of 2× ADVANTAGE® GC-Melt LA Buffer (Clontech, Mountain View, Calif., USA), 25 pmol of primer 066694 (16), 25 pmol of primer 066695 (Example 16), 1.25 units of ADVANTAGE® GC Genomic LA Polymerase Mix (Clontech, Mountain View, Calif., USA), and 9.25 µl water. The reaction was incubated in an EPPENDORF® MASTERCYCLER® programmed for 1 cycle at 95° C. for 10 minutes; 35 cycles each at 95° C. for 30 seconds, 60° C. for 30 seconds, and 72° C. for 4 minutes 30 seconds; 1 cycle at 72° C. for 5 minutes; and a 4° C. hold. The primers used in this screen were originally used to amplify the aspartic protease region. If the deletion vector was inserted into the aspartic protease locus, the amplified PCR fragment should be larger than the wild-type fragment since it contains the hph cassette used to disrupt the aspartic protease gene. The candidates that exhibited one larger band in the first Fungal Colony PCR screen were subjected to a second PCR screen using the primers shown below.

```
Primer 068331 (sense):
ATATCTCTCTCGAGGCCTGCTTATT        (SEQ ID NO: 59)

Primer 067947 (antisense):
CTACATCGAAGCTGAAAGCACGAGA        (SEQ ID NO: 60)
```

Primer 068331 is upstream of the 5' region of the aspartic protease gene contained in the deletion strain, and primer 067947 is in the hph cassette. Only those candidates that contain the aspartic protease disruption would produce a PCR fragment. The amplification reaction was composed of 1 µl of genomic DNA from the candidate (extracted according to Example 10), 1 µl of 10 mM dNTPs, 12.5 µl of 2× ADVANTAGE® GC-Melt LA Buffer, 25 pmol of primer 068331, 25 pmol of primer 067947, 0.25 µl 1.25 units of ADVANTAGE® GC Genomic LA Polymerase Mix, and 9.25 µl of water. The reaction was incubated in an EPPENDORF® MASTERCYCLER® programmed for 1 cycle at 95° C. for 2 minutes; 30 cycles each at 95° C. for 30 seconds, 55° C. for 30 seconds, and 72° C. for 2 minutes; 1 cycle at 72° C. for 5 minutes; and a 4° C. hold.

Southern blot analysis was performed to confirm the disruption of the aspartic protease gene by plasmid pAgJg111. Genomic DNA was extracted from the deletion strain and *Trichoderma reesei* strain 981-O-8 as described in Example 10. Two µg of genomic DNA from the deletion strain and *Trichoderma reesei* strain 981-O-8, as well as 1 ng of plasmid DNA from pAgJg111, were digested with Nco I and Pvu II. *T. reesei* strain 981-O-8 and pAgJg111 were included in the Southern blot as controls. The genomic DNA digestion reaction was composed of 2 µg of genomic DNA, 1 µl of Nco I, 1 µl of Pvu II, 5 µl of 10×NEB Buffer 2, and water to 50 µl. Both genomic DNA digestions were incubated at 37° C. for approximately 14-16 hours. Plasmid pAgJg111 was digested in a reaction composed of 1 ng of pAgJg111 DNA, 0.5 µl of Nco I, 0.5 µl of Pvu II, 2 µl of 10×NEB Buffer 2, and water to 20 µl. The digestion was incubated at 37° C. for approximately 1 hour.

The digestions were submitted to 0.7% agarose gel electrophoresis using TAE buffer and blotted onto NYTRAN® SuperCharge blotting membrane using a TURBOBLOTTER® for 14-16 hours following the manufacturer's recommendations. The membrane was hybridized with a 500 bp digoxigenin-labeled *Trichoderma reesei* 42 kDa aspartic protease probe, which was synthesized by incorporation of digoxigenin-11-dUTP by PCR using primers 068128 (sense) and 068129 (antisense) shown below.

```
Primer 068128 (sense):
AGTCAGGTTCAGCAGATCGCCAGGGATGG  (SEQ ID NO: 61)

Primer 068129 (antisense):
GTGGTTCTCCAACGCCGCCAGCAGC      (SEQ ID NO: 62)
```

The amplification reaction was composed of 5 µl of 10× ThermoPol Reaction Buffer, 2.5 µl of PCR DIG Labeling Mix, 2 ng of pAgJg111, 50 pmol of primer 068128, 50 pmol of primer 068129, 2.5 µl of 10 mM dNTPs, 5 units of Taq DNA polymerase, and 35.5 µl of water. The reactions were incubated in an EPPENDORF® MASTERCYCLER® 5333 programmed for 1 cycle at 95° C. for 2 minutes; 30 cycles each at 95° C. for 30 seconds, 60° C. for 30 seconds, and 72° C. for 40 seconds; 1 cycle at 72° C. for 15 minutes; and a 4° C. hold. The PCR reaction product was purified by 1% agarose gel electrophoresis using TAE buffer, excised from the gel, and extracted using a QIAQUICK® Gel Extraction Kit according to the manufacturer's instructions. Incorporation of digoxigenin was indicated by increase in molecular mass.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. The strain containing the aspartic protease deletion was designated *Trichoderma reesei* AgJg111-50.

Example 18

*Aspergillus aculeatus* GH10 Xylanase Expression in Aspartic Protease Deficient Strain AgJg111-50

To determine whether deletion of the 42 kDa aspartic protease was effective in eliminating degradation of the *Aspergillus aculeatus* GH10 xylanase, plasmid pSaMe-AaXYL (Example 14), which contains the *Aspergillus aculeatus* GH10 xylanase coding sequence, was transformed into *Trichoderma reesei* AgJg111-50. Protoplasts of *T. reesei* AgJg111-50 were generated as described in Example 12 and transformed with plasmid pSaMe-AaXYL. Twenty transformants containing the *Aspergillus aculeatus* GH10 xylanase were randomly selected from COVE plates and cultured in 125 ml shake flasks containing 25 ml of cellulase-inducing medium at pH 6.0 inoculated with spores of the transformants and incubated at 28° C. for 5 days with agitation at 200 rpm. *Trichoderma reesei* strain 981-O-8 and *Trichoderma reesei* AgJg111-50 were both run as controls. Culture broth samples were removed 5 days post-inoculation, centrifuged at 15,700×g for 10 minutes in a micro-centrifuge, and the supernatants transferred to new tubes.

The supernatants were analyzed by SDS-PAGE using an 8-16% CRITERION™ Tris-HCl gels with a CRITERION™ Cell. Five µl of day 5 samples were suspended in 2× concentration of Laemmli Sample Buffer and heated at 95° C. for 5 minutes in the presence of 5% β-mercaptoethanol. All samples were loaded onto the SDS-PAGE gels and subjected to electrophoresis in 1× Tris/Glycine/SDS running buffer. The resulting gels were stained with BIO-SAFE™ Coomassie Stain. SDS-PAGE analysis suggested that deletion of the aspartic protease gene for the production of *Aspergillus aculeatus* GH10 xylanase did not completely prevent proteolysis of the protein. The aspartic protease deletion strain *T. reesei* AgJg111-50 did not exhibit any unusual expression patterns of any protein and behaved similarly to the parent strain, *Trichoderma reesei* strain 981-O-8.

Example 19

Construction of *Trichoderma reesei* Trypsin-Like Serine Protease Gene Deletion Plasmid pAgJg116

The deletion vector pAgJg116 was constructed to disrupt expression of a *Trichoderma reesei* 25 kDa trypsin-like serine protease gene (SEQ ID NO: 5 for the DNA sequence and SEQ ID NO: 6 for the deduced amino acid sequence). Plasmid pAgJg116 was generated by first amplifying 5' and 3' flanking regions and cloning them into the vector pCR®2.1-TOPO®. The 5' flanking region contains a region upstream of the 25 kDa serine protease coding region and part of the 25 kDa trypsin-like serine protease coding region. The 5' flanking region was amplified using the primers 067518 (sense) and 067519 (antisense) shown below. Primer 067518 was engineered to contain Asc I and Not I sites on the 5' end of the primer. Primer 067519 was engineered to contain an Asc I site on the 5' end of the primer.

```
Primer 067518 (sense):
                                       (SEQ ID NO: 63)
AAAGGCGCGCCGCGGCCGCGAAGAAGAAGAAGAACGTGAAAGAG Primer 067519 (antisense):
                                       (SEQ ID NO: 64)
AAAGGCGCGCCCGGTCGAGCCGGCCACGGGGTCGGA
```

The 5' region of the trypsin-like serine protease was amplified by PCR in a reaction composed of 175 µg of *T. reesei* genomic DNA (Example 10), 1 µl of Herculase II Fusion DNA Polymerase, 50 pmol of primer 067518, 50 pmol of primer 067519, 5 µl of 10 mM dNTPs, 5 µl of 5× Herculase II reaction buffer (Stratagene, LaJolla, Calif., USA), and 31 µl of water. The reaction was incubated in an EPPENDORF® MASTERCYCLER® programmed for 1 cycle at 95° C. for 2 minutes; 30 cycles each at 95° C. for 20 seconds, 60° C. for 20 seconds, and 72° C. for 45 seconds; 1 cycle at 72° C. for 3 minutes; and a 4° C. hold. A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 µl of the purified PCR fragment, 1 µl of the 10× Thermopol Buffer, 0.5 µl of 10 mM dNTPs, 0.5 µl of Taq DNA polymerase, and 3 µl of water. The reaction was incubated at 72° C. for 15 minutes. The 5' region of the trypsin-like serine protease fragment was cloned into pCR®2.1-TOPO® in a reaction composed of 2.5 µl of the 5' trypsin-like serine protease region PCR fragment, 1 µl of Salt Solution, 1.5 µl of water, and 1 µl of pCR®2.1-TOPO®. The resulting plasmid was designated 5'SP-TOPO.

The 3' region of the trypsin-like serine protease fragment was cloned into pCR®2.1-TOPO® using primers 067520 (sense) and 067521 (antisense) shown below. Primer 067520 was engineered to contain a Sbf I site on the 5' end of the primer. Primer 067521 was engineered to contain Sbf I and Not I sites on the 5' end of the primer.

```
Primer 067520 (Sense):
                                       (SEQ ID NO: 65)
AAACCTGCAGGTCACCACCGCTGGCTGGTAAGCATCATC Primer 067521 (Antisense):
                                       (SEQ ID NO: 66)
AAACCTGCAGGCGGCCGCACAAAGCTAGGAGTCTTGACGTGAT
```

The 3' region of the trypsin-like serine protease gene was amplified by PCR in a reaction composed of 175 µg of *T. reesei* genomic DNA (Example 10), 1 µl of Herculase II Fusion DNA Polymerase, 50 pmol of primer 067520, 50 pmol of primer 067521, 5 µl of 10 mM dNTPs, 5 µl of 5× Herculase II reaction buffer, and 31 µl of water. The reaction was incubated in an EPPENDORF® MASTERCYCLER® programmed for 1 cycle at 95° C. for 2 minutes; 30 cycles each at 95° C. for 20 seconds, 60° C. for 20 seconds, and 72° C. for 45 seconds; 1 cycle at 72° C. for 3 minutes; and a 4° C. hold. A 1.5 kb PCR fragment was purified by 1% agarose gel electrophoresis using TAE buffer, excised from the gel, and extracted using a QIAQUICK® Gel Extraction Kit according to the manufacturer's instructions. The gel purified PCR fragment was treated with Taq DNA polymerase to add 3' A-overhangs to the fragment in a reaction composed of 5 µl of the purified PCR fragment, 1 µl of the 10× Thermopol Buffer, 0.5 µl of 10 mM dNTPs, 0.5 µl of Taq DNA polymerase, and 3 µl of water. The reaction was incubated at 72° C. for 15 minutes. The 5' region of the trypsin-like serine protease fragment was cloned into pCR®2.1-TOPO® according to the manufacturer's instruction in a reaction composed of 2.5 µl of the 5' trypsin-like serine protease region PCR fragment, 1 µl of Salt Solution, 1.5 µl of water, and 1 µl of pCR®2.1-TOPO®. The resulting plasmid was designated 3'SP-TOPO.

Plasmid 5'SP-TOPO was digested with Asc I and cloned into Asc I digested plasmid pJfyS1579-41-11 (Example 9) in a reaction composed of 12.4 µg of digested 5'SP-TOPO plasmid DNA, 5 µl of Asc I, 10 µl of 10×NEB Buffer 4 (New England Biolabs, Inc, Ipswich, Mass., USA), and 55 µl of water. The restriction enzyme digestion was incubated at 37° C. for 2 hours. The digestion was purified by 1% agarose gel electrophoresis using TAE buffer, where a 1.5 kb fragment was excised from the gel and extracted using a QIAQUICK® Gel Extraction Kit according to the manufacturer's instructions. The Asc I digested 5'SP-TOPO fragment was ligated to the Asc I digested pJfyS1579-49-11 in a reaction composed of 282 ng of Asc I digested 5'SP-TOPO, 120 ng of Asc I digested pJfyS1579-49-11, 2 µl of Quick Ligase (New England Biolabs, Inc, Ipswich, Mass., USA), 15 µl of 2× Quick Ligase Buffer (New England Biolabs, Inc, Ipswich, Mass., USA), and 2 µl of water. The ligation reaction was incubated at room temperature for 15 minutes. The resulting plasmid was designated pJfyS1579+5'SP.

Figure 20:
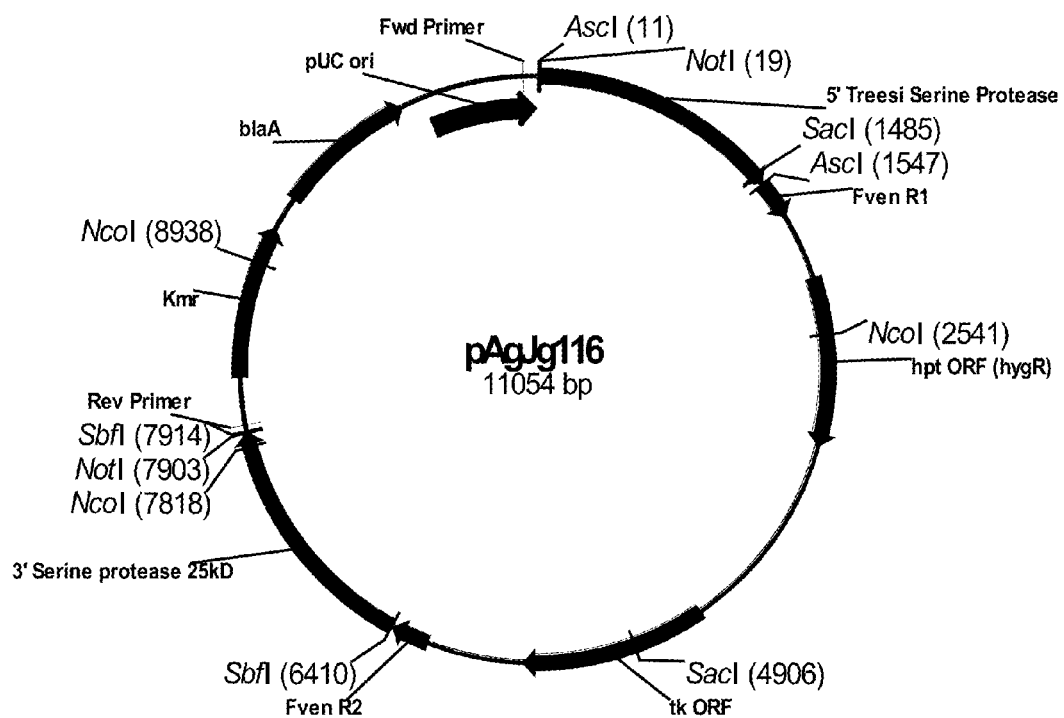
FIG. 20 shows a restriction map of pAgJg116.

To construct plasmid pAgJg116, plasmids 3'SP-TOPO and pJfyS1579+5'SP were digested with Sbf I. The digestions were composed of 7.5 µg of pJfyS1579+5'SP or 12.5 µg of 3'SP-TOPO, 5 µl of Sbf I, 10 µl of 10×NEB Buffer 4, and 55 µl of water. Both digestion reactions were incubated at 37° C. overnight. Two µl of calf intestinal alkaline phosphatase (CIP) was added to the pJfyS1579+5'SP digestion reaction and incubated at 37° C. for an additional hour. A 9.5 kb fragment from pJfyS1579+5SP/Sbf I and a 1.5 kb fragment from 3SP-TOPO/Sbf I were purified by 0.8% agarose gel electrophoresis using TAE buffer, excised from the gel, and extracted using a QIAQUICK® Gel Extraction Kit according to the manufacturer's instructions. The Sbf I digested 3'SP-TOPO fragment was ligated to the Sbf I digested pJfyS1579+5'SP fragment in a reaction composed of 767 ng of Sbf I digested 3'SP-TOPO, 380 ng of Sbf I digested pJfyS1579+5'SP, 2 µl of Quick Ligase, 15 µl of 2× Quick Ligase Buffer, and 1 µl of water. The ligation reaction incubated at room temperature for 20 minutes. The resulting plasmid was designated pAgJg116 (FIG. 20).

Example 20

Generation of Trypsin-Like Serine Protease Gene Deletion *Trichoderma reesei* Strain AgJg116-19

*Trichoderma reesei* strain 981-O-8 protoplasts were transformed with Not I-linearized pAgJg116 using the method described in Example 12 to delete the trypsin-like serine protease gene. Ninety transformants were selected on PDA plates containing 25 µg of hygromycin B per ml. The transformants were sub-cultured to PDA plates to generate spores.

Transformants of *Trichoderma reesei* strain 981-O-8 containing the deletion vector pAgJg116 were cultured in 125 ml shake flasks containing 25 ml of cellulase-inducing medium at pH 6.0 inoculated with spores of the transformants and incubated at 28° C. for 5 days with agitation at 200 rpm. *Trichoderma reesei* strain 981-O-8 was run as a control. Culture broth samples were removed 5 days post-inoculation, centrifuged at 15,700×g for 10 minutes in a micro-centrifuge, and the supernatants transferred to new tubes.

The supernatants of each transformant were assayed for protease activity using the synthetic substrate Val-Leu-Lys 4-nitroanilide (Bachem AG, Bubendorf, Switzerland). The substrate was initially dissolved in dimethyl sulfoxide at a concentration of 100 mg/ml. The dissolved substrate was then diluted 200-fold into 100 mM NaCl-100 mM MOPS pH 7.0. The reaction was initiated by adding 10 µl of each transformant supernatant to 100 µl of the diluted substrate in a flat-bottomed 96-well plate. The reaction plate was incubated at 50° C. for 30 minutes and then the absorbance at 405 nm was measured using a SPECTRAMAX® Microplate Reader. Transformants exhibiting little to no protease activity were subjected to a PCR screen using the primers shown below.

```
Primer 068155 (sense):
GCTGTTTGGCCCTCGAAACTGCCGG       (SEQ ID NO: 67)

Primer 067947 (antisense):
CTACATCGAAGCTGAAAGCACGAGA       (SEQ ID NO: 68)
```

Primer 068155 is upstream of the 5' region of the trypsin-like serine protease gene contained in the deletion strain, and primer 067947 is in the hph cassette. Only those candidates that contain the trypsin-like serine protease disruption would produce a PCR fragment. The PCR screen was performed by Fungal Colony PCR according to the modified protocol described in Example 17. A small amount of spores from each candidate was suspended in 25 µl of TE buffer and heated on high in a microwave oven for 1 minute. The microwaved spore suspension was used as a template in a PCR reaction to screen for the aspartic protease deletion. The reaction was composed of 1 µl of the spore suspension, 1 µl of 10 mM dNTPs, 12.5 µl of 2× ADVANTAGE® GC-Melt LA Buffer, 25 pmol of primer 068155, 25 pmol of primer 067947, 1.25 units of ADVANTAGE® GC Genomic LA Polymerase Mix, and 9.25 µl water. The reaction was incubated in an EPPENDORF® MASTERCYCLER® programmed for 1 cycle at 95° C. for 10 minutes; 35 cycles each at 95° C. for 30 seconds, 60° C. for 30 seconds, and 72° C. for 2 minutes 30 seconds; 1 cycle at 72° C. for 5 minutes; and a 4° C. hold.

Southern blot analysis was performed to confirm the disruption of the 25 kDa trypsin-like serine protease gene by the vector pAgJg116. Genomic DNA was extracted from the deletion strains and Trichoderma reesei strain 981-O-8 according to Example 10. Two µg of genomic DNA from the deletion strains and Trichoderma reesei strain 981-O-8, along with 1 ng of plasmid DNA from pAgJg116 were digested with Nco I and Sac I. Trichoderma reesei strain 981-O-8 and pAgJg116 were included in the Southern blot as controls. The genomic DNA was digested in a reaction composed of 2 µg of genomic DNA, 1 µl of Nco I, 1 µl of Sac I, 5 µl of 10×NEB Buffer 1 (New England Biolabs, Inc, Ipswich, Mass., USA), 0.5 µl of 100×BSA, and water in a 50 µl reaction. Both digests were incubated at 37° C. for approximately 14-16 hours. Plasmid pAgJg116 was digested in a reaction composed of 1 ng of pAgJg116 DNA, 0.5 µl of Nco I, 0.5 µl of Sac I, 2 µl of 10×NEB Buffer 1, 0.2 µl of 100×BSA, and water in a 20 µl reaction. The digestion was incubated at 37° C. for approximately 1 hour and 30 minutes.

The digests were submitted to 0.7% agarose gel electrophoresis using TAE buffer and blotted onto NYTRAN® SuperCharge blotting membrane using a TURBOBLOTTER® for 14-16 hours following the manufacturer's recommendations. The membrane was hybridized with a 500 bp digoxigenin-labeled Trichoderma reesei 25 kDa trypsin-like serine protease probe, which was synthesized by incorporation of digoxigenin-11-dUTP during PCR using primers 068128 (sense) and 068129 (antisense) shown below.

```
Primer 068233 (sense):
CAACCCAAAGATATCGCCAGATCCA       (SEQ ID NO: 69)

Primer 068234 (antisense):
ACGATAAACTCCCCCACGGCTGAAG      (SEQ ID NO: 70)
```

The amplification reaction was composed of 5 µl of 10× ThermoPol Reaction Buffer, 2.5 µl of PCR DIG Labeling Mix, 2 ng of pAgJg116, 50 pmol of primer 068233, 50 pmol of primer 068234, 2.5 µl of 10 mM dNTPs, 5 units of Taq DNA polymerase, and 35.5 µl water. The reaction was incubated in an EPPENDORF® MASTERCYCLER® programmed for 1 cycle at 95° C. for 2 minutes; 30 cycles each 95° C. for 30 seconds, 60° C. for 30 seconds, and 72° C. for 40 seconds; 1 cycle at 72° C. for 15 minutes; and a 4° C. hold. The PCR product was size-selected by 1.5% agarose gel electrophoresis using TAE buffer, excised from the gel, and extracted using a QIAQUICK® Gel Extraction Kit according to the manufacturer's instructions. Incorporation of digoxigenin was indicated by increase in molecular mass.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay following the manufacturer's instructions. Several transformants were confirmed to contain the trypsin-like serine protease deletion. One transformant was selected and designated Trichoderma reesei AgJg116-19.

Example 21

Aspergillus aculeatus GH10 Xylanase Expression in Trypsin-Like Serine Protease Deficient Strain AgJg116-19

To determine whether deletion of the 25 kDa trypsin-like serine protease was effective in preventing degradation of recombinantly expressed Aspergillus aculeatus GH10 xylanase, plasmid pSaMe-AaXYL (Example 14), which contains the Aspergillus aculeatus GH10 xylanase coding sequence, was transformed into the Trichoderma reesei AgJg116-19 strain. Protoplasts of Trichoderma reesei AgJg116-19 were generated as described in Example 12 and transformed with plasmid pSaMe-AaXYL. Thirty-six transformants containing the Aspergillus aculeatus GH10 xylanase were randomly selected from COVE plates and cultured in 125 ml shake flasks containing 25 ml of cellulase-inducing medium at pH 6.0 inoculated with spores of the transformants and incubated at 28° C. for 5 days with agitation at 200 rpm. Trichoderma reesei strain 981-O-8 and Trichoderma reesei AgJg116-19 were both run as controls. Culture broth samples were removed 5 days post-inoculation, centrifuged at 15,700×g for 10 minutes in a micro-centrifuge, and the supernatants transferred to new tubes.

The supernatants were analyzed by SDS-PAGE using an 8-16% CRITERION™ Tris-HCl gels with a CRITERION™ Cell. Five µl of day 5 samples were suspended in 2× concentration of Laemmli Sample Buffer and heated at 95° C. for 5 minutes in the presence of 5% 3-mercaptoethanol. All samples were loaded onto the SDS-PAGE gels and subjected to electrophoresis in 1× Tris/Glycine/SDS running buffer. The resulting gels were stained with BIO-SAFE™ Coomassie Stain. SDS-PAGE analysis indicated that none of the transformants expressing the Aspergillus aculeatus GH10 xylanase produced any trace of degradation of the xylanase.

Also, the trypsin-like serine protease deletion strain *Trichoderma reesei* AgJg116-19 did not exhibit any unusual expression patterns of any protein and behaved similarly to the parent strain, *Trichoderma reesei* strain 981-O-8. The deletion of the 25 kDa trypsin-like serine protease gene in *Trichoderma reesei* strain 981-O-8 appeared effective in eliminating degradation of the *Aspergillus aculeatus* GH10 xylanase.

Example 22

Construction of a *Trichoderma reesei* Ku70 Gene Deletion Plasmid pAgJg115

The deletion vector pAgJg115 was constructed to disrupt the *Trichoderma reesei* ku70 gene. Disruption of the ku70 was required to increase the efficiency of gene targeting in *Trichoderma reesei*.

Plasmid pAgJg115 was generated by first amplifying 5' and 3' flanking regions and cloning them into the vector pCR®2.1-TOPO®. The 1.5 kb 5' flank contains a region upstream of the ku70 gene as well as part of the ku70 coding sequence. The 5' flanking region was amplified using primers 067491 (sense) and 067492 (antisense) shown below. Primer 067491 was engineered to contain Asc I and Not I sites on the 5' end of the primer. Primer 067492 was engineered to contain an Asc I site on the 5' end of the primer.

```
Primer 067491 (sense):
                                      (SEQ ID NO: 71)
5'-AAAGGCGCGCCGCGGCCGCCCATGGTGAGAAGCCGGGTTCGGGAG-3'

Primer 067492 (antisense):
                                      (SEQ ID NO: 72)
5'-AAAGGCGCGCC AGCCCTTGACAGTGATCTTGAGTCC-3'
```

The 5' region of the ku70 gene was amplified by PCR in a reaction composed of 175 µg of *T. reesei* genomic DNA, 1 µl of Herculase II Fusion DNA Polymerase, 50 pmol of primer 067491, 50 pmol of primer 067492, 5 µl of 10 mM dNTPs, 10 µl of 5× Herculase II Reaction buffer (Stratagene), and 31 µl of water. The reaction was incubated in an EPPENDORF® MASTERCYCLER® programmed for 1 cycle at 95° C. for 2 minutes; 30 cycles each at 95° C. for 20 seconds, 61° C. for 20 seconds, and 72° C. for 45 seconds; 1 cycle at 72° C. for 3 minutes; and a 4° C. hold.

A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 µl of the purified PCR fragment, 1 µl of the 10× Thermopol Buffer, 0.5 µl of 10 mM dNTPs, 1 µl of Taq DNA polymerase, and 3 µl of water. The reaction was incubated at 72° C. for 15 minutes. The 5' region of the ku70 fragment was cloned into pCR®2.1-TOPO® in a reaction composed of 2.5 µl of the 5' flank ku70 PCR fragment, 1 µl of Salt Solution, 1 µl of water, and 1 µl of pCR®2.1-TOPO® and 2 µl of the reaction was transformed into ONE SHOT® TOP10 Chemically Competent *E. coli* cells (Invitrogen, Inc., Carlsbad, Calif., USA) according to the manufacturer's instructions. Transformants were selected on 2×YT agar plates supplemented with 100 µg of ampicillin per ml and incubated at 37° C. for 16 hours. The resulting plasmid was designated 5'ku70-TOPO.

The 3' region of the ku70 fragment was cloned into pCR®2.1-TOPO® using primers 067493 (sense) and 067494 (antisense) shown below. Primer 067493 was engineered to contain a Sbf I site on the 5' end of the primer. Primer 067494 was engineered to contain Sbf I and Not I sites on the 5' end of the primer.

```
Primer 067493 (Sense):
                                      (SEQ ID NO: 73)
5'-AAACCTGCAGGACAACATTGTGCATCGGCAAACGCC-3'

Primer 067494 (Antisense):
                                      (SEQ ID NO: 74)
5'-AAACCTGCAGGCGGCCGCAAAGTGCCGGGGGTGCCCCAAGTCG-3'
```

The 3' region of the ku70 gene was amplified by PCR in a reaction composed of 175 µg of *T. reesei* genomic DNA, 1 µl of Herculase II Fusion DNA Polymerase, 50 pmol of primer 067493, 50 pmol of primer 067494, 5 µl of 10 mM dNTPs, 10 µl of 5× Herculase II Reaction buffer, and 31 µl of water. The reaction was incubated in an EPPENDORF® MASTERCYCLER® programmed for 1 cycle at 95° C. for 2 minutes; 30 cycles each at 95° C. for 20 seconds, 61° C. for 20 seconds, and 72° C. for 45 seconds; 1 cycle at 72° C. for 3 minutes; and a 4° C. hold.

A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 µl of the purified PCR fragment, 1 µl of the 10× Thermopol Buffer, 0.5 µl of 10 mM dNTPs, 1 µl of Taq DNA polymerase, and 3 µl of water. The reaction was incubated at 72° C. for 15 minutes. The 3' region of the ku70 fragment was cloned into pCR®2.1-TOPO® in a reaction composed of 2.5 µl of the 3' flank ku70 PCR fragment, 1 µl of Salt Solution, 1 µl of water, and 1 µl of pCR®2.1-TOPO® and 2 µl of the reaction was transformed into ONE SHOT® TOP10 Chemically Competent *E. coli* cells according to the manufacturer's instructions. Transformants were selected on 2×YT agar plates supplemented with 100 µg of ampicillin per ml and incubated at 37° C. for 16 hours. The resulting plasmid was designated 3'ku70-TOPO.

Plasmid 5'ku70-TOPO was digested with Asc I in order to be cloned into Asc I digested plasmid pJfyS1579-41-11 (Example 9) in a reaction composed of 14.6 µg of 5'ku70-TOPO plasmid DNA, 5 µl of Asc I, 10 µl of 10×NEB Buffer 4, and 55 µl of water. The restriction enzyme digestion was incubated at 37° C. for approximately 14-16 hours. The digestion was purified by 1% agarose gel electrophoresis using TAE buffer, where a 1.5 kb fragment was excised from the gel and extracted using a QIAQUICK® Gel Extraction Kit according to the manufacturer's instructions. The Asc I digested 5'ku70-TOPO fragment was ligated to the Asc I digested pJfyS1579-49-11 in a reaction composed of 329.6 ng of Asc I digested 5'ku70-TOPO, 120 ng of Asc I digested pJfyS1579-49-11, 2 µl of Quick Ligase, 15 µl of 2× Quick Ligase Buffer, and 2 µl of water. The ligation reaction was incubated at room temperature for 15 minutes and 4 µl of the ligation reaction was transformed into ONE SHOT® TOP10 Chemically Competent *E. coli* cells according to the manufacturer's instructions. Transformants were selected on 2×YT agar plates supplemented with 100 µg of ampicillin per ml and incubated at 37° C. for 16 hours. The resulting plasmid was designated pJfyS1579+5ku70.

Figure 21:
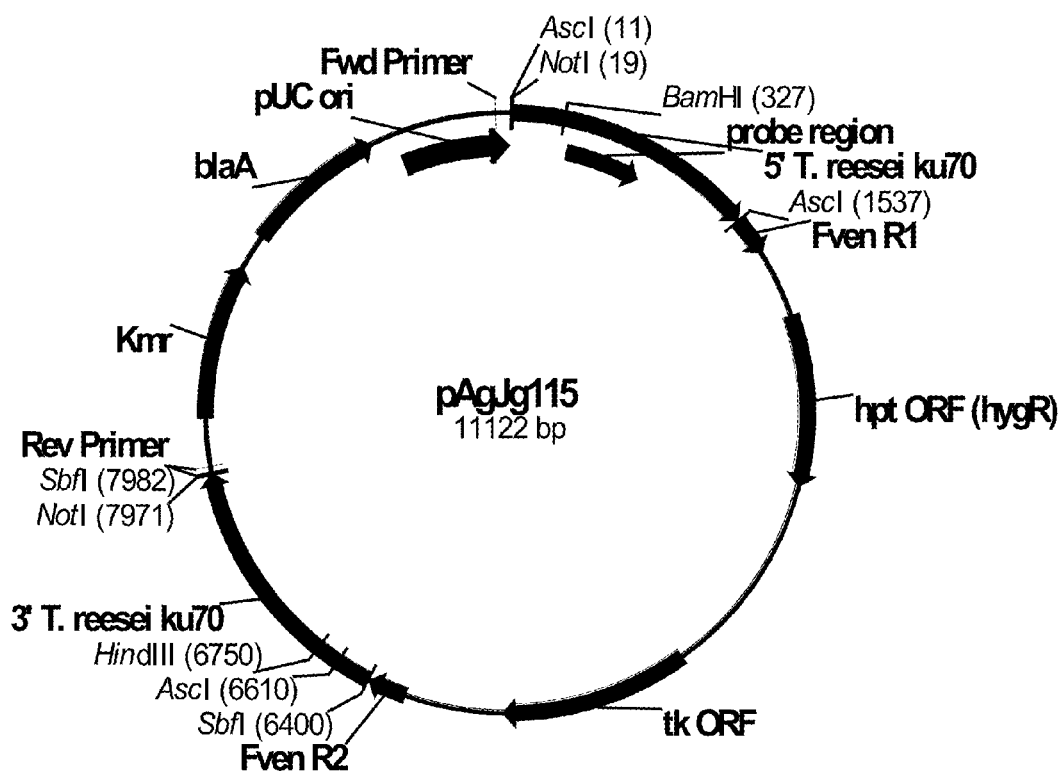
FIG. 21 shows a restriction map of pAgJg115.

To construct plasmid pAgJg115, plasmids 3'ku70-TOPO and pJfyS1579+5ku70 were digested with Sbf I. The digestion of pJfyS1579+5ku70 was composed of 3.98 µg of pJfyS1579+5ku70, 5 µl of Sbf I, 30 µl of 10×NEB Buffer 4, and 165 µl of water. The digestion of 3'ku70-TOPO was composed of 13.8 µg of 3'ku70-TOPO, 5 µl of Sbf I, 10 µl of 10×NEB Buffer 4, and 55 µl of water Both digestion reactions were incubated at 37° C. for 4 hours. A 9.5 kb fragment from pJfyS1579+5ku70/Sbf I and a 1.5 kb fragment from 3'ku70-TOPO/Sbf I were purified by 1% agarose gel electrophoresis using TAE buffer, excised from the gels, and extracted using a QIAQUICK® Gel Extraction Kit according to the manufacturer's instructions. The Sbf I digested 3'ku70-TOPO fragment was ligated to the Sbf I digested pJfyS1579+5ku70 fragment in a reaction composed of 335.8 ng of Sbf I digested 3'ku70-TOPO, 69.76 ng of Sbf I digested pJfyS1579+5ku70, 2 µl of Quick Ligase, 20 µl of 2× Quick Ligase Buffer, and 2 µl of water. The ligation reaction incubated at room temperature for 20 minutes and 5 µl of the ligation reaction was transformed into ONE SHOT® TOP10 Chemically Competent E. coli cells according to the manufacturer's instructions. Transformants were selected on 2×YT agar plates supplemented with 100 µg of ampicillin per ml and incubated at 37° C. for 16 hours The resulting plasmid was designated pAgJg115 (FIG. 21).

Example 23

Generation of a Ku70 Gene Disruption in Trichoderma reesei

Trichoderma reesei strain 981-O-8 protoplasts were transformed with Not I-linearized pAgJg115 using the method previously described in Example 12. Transformations were plated onto PDA+1 M sucrose and then overlayed with a thin layer containing PDA+10 mM uridine+hygromycin (100 µg/ml). One hundred twenty-nine transformants were subcultured onto PDA plates to generate spores.

Possible candidates of Trichoderma reesei strain 981-O-8 containing the pAgJg115 deletion vector in the ku70 locus, thereby disrupting the ku70 gene, were screened by fungal spore PCR using a modified protocol of Suzuki et al., 2006, supra. A small amount of spores from each candidate was suspended in 25 µl of TE buffer and heated on high in a microwave oven for 1 minute. The microwaved spore suspension was used as a template in a PCR reaction to screen for the serine protease deletion. The reaction was composed of 1 µl of the spore suspension, 1 µl of 10 mM dNTPs, 12.5 µl of 2× ADVANTAGE® GC-Melt LA Buffer, 25 pmol of primer 067946, 25 pmol of primer 067947, 1.25 units of ADVANTAGE® GC Genomic LA Polymerase Mix, and 9.25 µl water. The reaction was incubated in an EPPENDORF® MASTERCYCLER® programmed for 1 cycle at 95° C. for 10 minutes; 35 cycles each at 95° C. for 30 seconds, 60° C. for 30 seconds, and 72° C. for 2 minutes 30 seconds; 1 cycle at 72° C. for 5 minutes; and a 4° C. hold. Primer 067946 is located upstream of the 5' flanking region and primer 067947 is located in the hpt marker; only the strains with the deletion cassette in the correct locus would yield a PCR product. Trichoderma reesei strain AgJg118-02 was identified in which the ku70 gene had been disrupted.

```
Primer 067946 (sense):
                                    (SEQ ID NO: 75)
5'-GCCAGGTGTCTGGCATGGCTGGCAAGCTGCGAC-3'

Primer 067947 (antisense):
                                    (SEQ ID NO: 76)
5'-CTACATCGAAGCTGAAAGCACGAGA-3'
```

Eight candidates were further evaluated by Southern blot analysis to confirm the disruption of the Trichoderma reesei ku70 gene. Genomic DNA was extracted from the deletion strains and Trichoderma reesei strain 981-O-8 as described in Example 10. Two µg of genomic DNA from the deletion strains and Trichoderma reesei strain 981-O-8, as well as 1 ng of plasmid DNA from pAgJg115, were digested with Hind III and Bam HI. T. reesei strain 981-O-8 and pAgJg115 were included in the Southern blot as controls. The genomic DNA digestion reaction was composed of 2 µg of genomic DNA, 1 µl of Hind III, 1 µl of Bam HI, 5 µl of 10×NEB Buffer 2, 0.5 µl of 100×BSA, and water to 50 µl. Both genomic DNA digestions were incubated at 37° C. for approximately 14-16 hours. Plasmid pAgJg115 was digested in a reaction composed of 1 ng of pAgJg111 DNA, 0.5 µl of Hind III, 0.5 µl of Bam HI, 2 µl of 10×NEB Buffer 2, 0.2 µl of 100×BSA, and water to 20 µl. The digestion was incubated at 37° C. for approximately 1 hour.

The digestions were submitted to 0.7% agarose gel electrophoresis using TAE buffer and blotted onto NYTRAN® SuperCharge blotting membrane using a TURBOBLOTTER® for 14-16 hours following the manufacturer's recommendations. The membrane was hybridized with a 500 bp digoxigenin-labeled Trichoderma reesei ku70 gene probe, which was synthesized by incorporation of digoxigenin-11-dUTP by PCR using primers 068067 (sense) and 068068 (antisense) shown below.

```
Primer 068067 (sense):
5'-CATCCACTCGGAGATGCTGA-3'    (SEQ ID NO: 77)

Primer 068068 (antisense):
5'-CGGAACTTGGTCTTTTCTGT-3'    (SEQ ID NO: 78)
```

The amplification reaction was composed of 5 µl of 10× ThermoPol Reaction Buffer, 2.5 µl of PCR DIG Labeling Mix, 2 ng of pAgJg115, 50 pmol of primer 068067, 50 pmol of primer 068068, 2.5 µl of 10 mM dNTPs, 5 units of Taq DNA polymerase, and 35.5 µl of water. The reactions were incubated in an EPPENDORF® MASTERCYCLER® 5333 programmed for 1 cycle at 95° C. for 2 minutes; 30 cycles each at 95° C. for 30 seconds, 55° C. for 30 seconds, and 72° C. for 40 seconds; 1 cycle at 72° C. for 15 minutes; and a 4° C. hold. The PCR reaction product was purified by 1% agarose gel electrophoresis using TAE buffer, excised from the gel, and extracted using a QIAQUICK® Gel Extraction Kit according to the manufacturer's instructions. Incorporation of digoxigenin was indicated by increase in molecular mass.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. The strain containing the ku70 gene disruption was designated Trichoderma reesei AgJg115-104.

The disruption construct pAgJg115 contains the E. coli hygromycin phosphotransferase (hpt) gene and the Herpes simplex virus thymidine kinase (tk) gene flanked by direct repeats. The direct repeats were inserted to facilitate the excision of the hpt and tk selectable markers.

Spores from T. reesei AgJg115-104 were plated onto Trichoderma minimal medium plates containing 1 µM 5-fluoro-2'-deoxyuridine (FdU) at concentrations of $1 \times 10^5$ and $1 \times 10^6$ and incubated at 28° C. Fifteen isolates were sub-cultured onto Trichoderma minimal medium plates containing 1 µM FdU and incubated at 28° C. The fifteen isolates were then tested for sensitivity to hygromycin by sub-culturing them onto PDA plates with 25 µg/ml hygrocmycin and incubating them at 28° C. None of the isolates grew on the hygromcyin plates, suggesting that the hpt and tk markers have been excised out of the strain.

To confirm the absence of the hpt and tk markers in *T. reesei* strain AgJg115-104, two isolates were evaluated by Southern blot. Genomic DNA was extracted from the marker-free disruption strains and *T. reesei* strain 981-O-8 as described in Example 10. Two µg of genomic DNA from the deletion strains and *Trichoderma reesei* strain 981-O-8 were digested with Hind III and Bam HI. *T. reesei* strain 981-O-8 was included in the Southern blot as a control. The genomic DNA digestion reaction was composed of 2 µg of genomic DNA, 1 µl of Hind III, 1 µl of Bam HI, 5 µl of 10×NEB Buffer 2, 0.5 µl of 100×BSA, and water to 50 µl. Both genomic DNA digestions were incubated at 37° C. for approximately 14-16 hours The digestions were submitted to 0.7% agarose gel electrophoresis using TAE buffer and blotted onto NYTRAN® SuperCharge blotting membrane using a TURBOBLOTTER® for 14-16 hours following the manufacturer's recommendations. The membrane was hybridized with a 500 bp digoxigenin-labeled *Trichoderma reesei* ku70 gene probe as described above.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. The marker free strain containing the ku70 gene disruption was designated *Trichoderma reesei* AgJg115-104-7B1.

Example 24

Generation of a Single Protease Deletion *Trichoderma reesei* Strain SMai-TrSP-30-22

*Trichoderma reesei* KU70-deficient strain AgJg115-104-7B1 protoplasts were transformed with Not I-linearized pDAtw18 (Example 11) using the method described in Example 12 to delete the *Trichoderma reesei* subtilisin-like serine protease gene. Thirty-six transformants were selected on PDA plates containing 10 µg of hygromycin B per ml. The transformants were sub-cultured to PDA plates to generate spores.

Fungal spore PCR using the modified protocol of Suzuki et al., 2006, supra was used to screen for transformants bearing putative deletion using a sense primer (067871) that was designed in the 5'-UTR of subtilisin-like serine protease gene and an antisense primer (067872) within the 3'-UTR.

```
Primer 067871 (Sense Primer):
                                    (SEQ ID NO: 79)
5'-ACTTCGGGGGATGGAAGTACATAAACTG-3'

Primer 067872 (AntiSense Primer):
                                    (SEQ ID NO: 80)
5'-CTCGATTCGCCATTAGATGTTTTATACCTG-3'
```

A 5 kb PCR product would be generated only upon the occurrence of a precise gene replacement at the subtilisin-like serine protease gene locus. If the cassette had integrated elsewhere in the genome, amplification of the wild-type 3 Kb subtilisin-like serine protease gene would result.

A small amount of spores from each candidate was suspended in 25 µl of TE buffer and heated on high in a microwave oven for 1 minute. The microwaved spore suspension was used as a template in a PCR reaction to screen for the subtilisin-like serine protease gene deletion. The reaction was composed of 1 µl of the spore suspension, 1 µl of 10 mM dNTPs, 12.5 µl of 2× ADVANTAGE® GC-Melt LA Buffer, 25 pmol of primer 067871, 25 pmol of primer 067872, 1.25 units of ADVANTAGE® GC Genomic LA Polymerase Mix, and 9.25 µl water. The reaction was incubated in an EPPENDORF® MASTERCYCLER® programmed for 1 cycle at 95° C. for 10 minutes; 35 cycles each at 94° C. for 30 seconds, 60° C. for 30 seconds, and 72° C. for 5 minutes 30 seconds; 1 cycle at 72° C. for 15 minutes; and a 4° C. hold.

*Trichoderma reesei* strain SMai-TrSP-30 was identified as deleted for the subtilisin-like serine protease gene.

The deletion construct pDAtw18 contains the positively-selectable hygromycin phosphoryl transferase (hpt) gene and the other encoding the negatively-selectable thymidine kinase (tk) gene, flanked by a direct repeats. The direct repeats were inserted to facilitate the excision of the hpt and tk selectable markers and generate a marker-free strain so it can be used as a host to delete a second protease gene.

Spores from *T. reesei* SMai-TrSP-30 were plated onto *Trichoderma* minimal medium plates containing 1 µM 5-fluoro-2'-deoxyuridine (FdU) at concentrations of $1\times10^5$ and $1\times10^6$ and incubated at 28° C. Twenty-three isolates were sub-cultured onto *Trichoderma* minimal medium plates containing 1 µM FdU and incubated at 28° C. All 23 isolates were then screened for the absence of the hpt and tk markers by fungal spore PCR in the same manner described in Example 26.

Southern blot analysis was performed to confirm the deletion of the subtilisin-like serine protease gene and the absence of the hpt and tk markers. Genomic DNA was extracted from the deletion strains and the *T. reesei* ku70 deletion strain AgJg115-104-7B1 as previously described in Example 10 and 2 µg of each were digested with 20 units of Nco I-HF™ for 16 hours at 37° C. Digested DNA was fractionated by 0.7% agarose gel electrophoresis using TAE buffer for 4 hours and blotted onto a NYTRAN™ SuperCharge membrane using a TURBOBLOTTER™ for 16 hours following the manufacturer's recommendations. The membrane was hybridized with a 502 bp digoxigenin-labeled subtilisin-like serine protease gene probe, which was synthesized by incorporation of digoxigenin-11-dUTP by PCR using primers 067911 (sense) and 067912 (antisense) described above.

The amplification reaction (50 µl) was composed of 1× ThermoPol Reaction Buffer, 5 µl of PCR DIG Labeling Mix, 10 ng of pDAtw18, 0.3 µM primer 067911, 0.3 µM primer 067912, and 2.5 units of Taq DNA polymerase. The reactions were incubated in an EPPENDORF® MASTERCYCLER® 5333 programmed for 30 cycles each at 95° C. for 30 seconds, 56° C. for 30 seconds, and 72° C. for 40 seconds (15 minute final extension). Five microliters of the PCR product was size-selected by 1.5% agarose gel electrophoresis using TAE buffer, stained with ethidium bromide, and visualized under a UV transilluminator. Incorporation of digoxigenin was indicated by increase in molecular mass.

Hybridization was performed in DIG Easy Hyb buffer (Roche Molecular Biochemicals, Indianapolis, Ind., USA) at 42° C. for 17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. The marker-free strain containing the subtilisin-like serine protease gene deletion was designated *Trichoderma reesei* SMai-TrSP-30-22.

Example 25

Construction of *Trichoderma reesei* Trypsin-Like Serine Protease Gene Deletion Plasmid pAgJg117

The deletion vector pAgJg117 was constructed to delete the *Trichoderma reesei* 25 kDa trypsin-like serine protease gene. Plasmid pAgJg117 was generated by first amplifying 5' and 3' flanking regions and cloning them into the vector pCR®2.1-TOPO®. The 5' flanking region contains a 1.5 kb region upstream of the 25 kDa serine protease coding region. The 5' flanking region was amplified using primers 068616 (sense) and 068617 (antisense) shown below. Primer 068616 was engineered to contain Asc I and Not I sites on the 5' end of the primer. Primer 068617 was engineered to contain an Asc I site on the 5' end of the primer.

```
Primer 068616 (sense):
                                   (SEQ ID NO: 81)
5'-AAAGGCGCGCCGCGGCCGCAAAACACACACAATAACCAACCCCCA-3'

Primer 068617 (antisense):
                                   (SEQ ID NO: 82)
5'-AAAGGCGCGCC TGCGATGGAGGAAAAGCTGCGAGGGATGA-3'
```

The 5' region of the trypsin-like serine protease was amplified by PCR in a reaction composed of 175 μg of *T. reesei* genomic DNA, 1 μl of PLATINUM® Pfx DNA polymerase, 50 pmol of primer 068616, 50 pmol of primer 068617, 1.5 μl of 10 mM dNTPs, 10 μl of 10×Pfx Amplification buffer, and 33.5 μl of water. The reaction was incubated in an EPPENDORF® MASTERCYCLER® programmed for 1 cycle at 98° C. for 3 minutes; 30 cycles each at 98° C. for 30 seconds, 60° C. for 30 seconds, and 72° C. for 1 minute 30 seconds; 1 cycle at 72° C. for 15 minutes; and a 4° C. hold. A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 μl of the purified PCR fragment, 1 μl of the 10× Thermopol Buffer, 0.5 μl of 10 mM dNTPs, 0.5 μl of Taq DNA polymerase, and 3 μl of water. The reaction was incubated at 72° C. for 15 minutes. The 5' region of the trypsin-like serine protease fragment was cloned into pCR®2.1-TOPO® in a reaction composed of 3 μl of the 5' trypsin-like serine protease region PCR fragment, 1 μl of Salt Solution, 1 μl of water, and 1 μl of pCR®2.1-TOPO®. The resulting plasmid was designated 5'Serine.

The 3' region of the trypsin-like serine protease fragment was cloned into pCR®2.1-TOPO® using primers 068618 (sense) and 068619 (antisense) shown below. Primer 068618 was engineered to contain a Sbf I site on the 5' end of the primer. Primer 0668619 was engineered to contain Sbf I and Not I sites on the 5' end of the primer.

```
Primer 068618 (Sense):          (SEQ ID NO: 83)
5'-AAACCTGCAGGGCGATTCCCTGTGTTGGCAACCAAA-3'

Primer 068619 (Antisense):      (SEQ ID NO: 84)
5'-AAACCTGCAGGCGGCCGCAAGAAATACTCAGGAAAGGTGCCCA-3'
```

The 3' region of the trypsin-like serine protease gene was amplified by PCR in a reaction composed of 175 μg of *T. reesei* genomic DNA, 1 μl of PLATINUM® Pfx DNA polymerase, 50 pmol of primer 068618, 50 pmol of primer 068619, 1.5 μl of 10 mM dNTPs, 10 μl of 10×Pfx Amplification buffer, and 33.5 μl of water. The reaction was incubated in an EPPENDORF® MASTERCYCLER® programmed for 1 cycle at 98° C. for 3 minutes; 30 cycles each at 98° C. for 30 seconds, 60° C. for 30 seconds, and 72° C. for 1 minute 30 seconds; 1 cycle at 72° C. for 15 minutes; and a 4° C. hold. A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 μl of the purified PCR fragment, 1 μl of the 10× Thermopol Buffer, 0.5 μl of 10 mM dNTPs, 0.5 μl of Taq DNA polymerase, and 3 μl of water. The reaction was incubated at 72° C. for 15 minutes. The 3' region of the trypsin-like serine protease fragment was cloned into pCR®2.1-TOPO® in a reaction composed of 3 μl of the 5' trypsin-like serine protease region PCR fragment, 1 μl of Salt Solution, 1 μl of water, and 1 μl of pCR®2.1-TOPO®. The resulting plasmid was designated 3'Serine.

Plasmid 5'Serine was digested with Asc I in order to be cloned into Asc I digested plasmid pJfyS1579-41-11 (Example 9) in a reaction composed of 12.4 μg of 5'Serine plasmid DNA, 5 μl of Asc I, 10 μl of 10×NEB Buffer 4, and 55 μl of water. The restriction enzyme digestion was incubated at 37° C. for 2 hours. The digestion was purified by 1% agarose gel electrophoresis using TAE buffer, where a 1.5 kb fragment was excised from the gel and extracted using a QIAQUICK® Gel Extraction Kit according to the manufacturer's instructions. The Asc I digested 5'Serine fragment was ligated to the Asc I digested pJfyS1579-49-11 in a reaction composed of 233.7 ng of Asc I digested 5'SP-TOPO, 160 ng of Asc I digested pJfyS1579-49-11, 3 μl of Quick Ligase, 25 μl of 2× Quick Ligase Buffer, and 3 μl of water. The ligation reaction was incubated at room temperature for 15 minutes. The resulting plasmid was designated 5'Serine+pJfyS1579.

Figure 22:
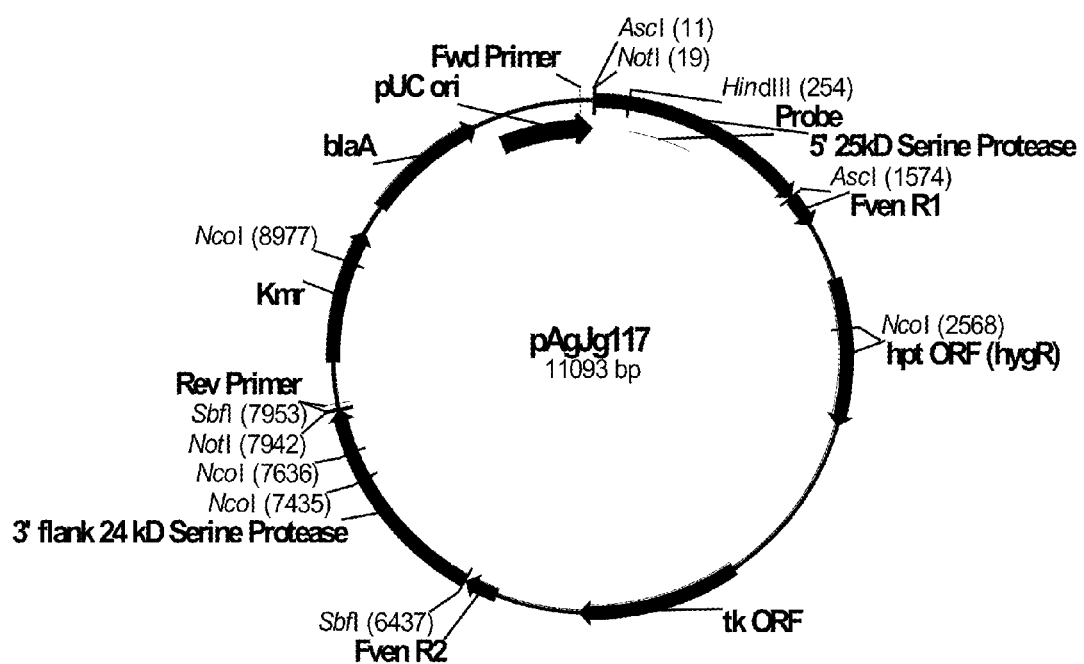
FIG. 22 shows a restriction map of pAgJg117.

To construct plasmid pAgJg117, plasmids 3'Serine and 5'Serine+pJfyS1579 were digested with Sbf I. The digestions were composed of 3.96 μg of 5'Serine+pJfyS1579 or 8.85 μg of 3'Serine, 4 μl of Sbf I, 10 μl of 10×NEB Buffer 4, and 56 μl of water. Both digestion reactions were incubated at 37° C. for two hours. One μl of calf intestinal alkaline phosphatase (CIP) was added to the 5'Serine+pJfyS1579 digestion reaction and incubated at 37° C. for an additional hour. A 9.5 kb fragment from 5'Serine+pJfyS1579 ISbf I and a 1.5 kb fragment from 3SP-TOPO/Sbf I were purified by 0.8% agarose gel electrophoresis using TAE buffer, excised from the gel, and extracted using a QIAQUICK® Gel Extraction Kit according to the manufacturer's instructions. The Sbf I digested 3'Serine fragment was ligated to the Sbf I digested 5'Serine+pJfyS1579 fragment in a reaction composed of 486 ng of Sbf I digested 3'Serine, 252 ng of Sbf I digested 5'Serine+pJfyS1579, 1 μl of Quick Ligase, 10 μl of 2× Quick Ligase Buffer, and 1.5 μl of water. The ligation reaction was incubated at room temperature for 20 minutes. The resulting plasmid was designated pAgJg117 (FIG. 22).

Example 26

Generation of a Double Protease Gene Deletion *Trichoderma reesei* Strain AgJg117-3-10A

*Trichoderma reesei* subtilisin-like serine protease gene deletion strain SMai-TrSP-30-22 protoplasts were generated and transformed with Not I-linearized pAgJg117 using the method previously described in Example 12 and plated onto PDA+1 M Sucrose+10 µg/ml of hygromycin. Six transformants were sub-cultured onto PDA plates to generate spores.

Possible candidates of *Trichoderma reesei* strain SMai-TrSP-30-22 containing the pAgJg117 deletion vector in the 25 kDa serine protease locus, thereby deleting the serine protease, were screened by fungal spore PCR using a modified protocol of Suzuki et al., 2006, supra. A small amount of spores from each candidate was suspended in 25 µl of TE buffer and heated on high in a microwave oven for 1 minute. The microwaved spore suspension was used as a template in a PCR reaction to screen for the serine protease deletion. The reaction was composed of 1 µl of the spore suspension, 1 µl of 10 mM dNTPs, 12.5 µl of 2× ADVANTAGE® GC-Melt LA Buffer, 25 pmol of primer 068980, 25 pmol of primer 067556, 1.25 units of ADVANTAGE® GC Genomic LA Polymerase Mix, and 9.25 µl water. The reaction was incubated in an EPPENDORF® MASTERCYCLER® programmed for 1 cycle at 95° C. for 10 minutes; 35 cycles each at 95° C. for 30 seconds, 55° C. for 30 seconds, and 72° C. for 5 minutes 45 seconds; 1 cycle at 72° C. for 15 minutes; and a 4° C. hold. The primers used in this screen were originally used as sequencing primers; primer 067556 is located at the end of the 5' flanking region and primer 068980 is located at the beginning of the 3' flanking region. If the deletion vector was inserted into the serine protease locus, the amplified PCR fragment should be larger than the wild-type fragment since it contains the hpt and tk cassette used to delete the serine protease gene. *Trichoderma reesei* strain AgJg117-3 was identified in which the serine protease had been deleted.

```
Primer 067556 (sense):            (SEQ ID NO: 85)
5'-CTTCTCTTTCTGGCATTGAC-3'

Primer 068980 (antisense):        (SEQ ID NO: 86)
5'-CTCGGAATCCTGCGGTTGCC-3'
```

The deletion construct pAgJg117 contains the *E. coli* hygromycin phosphotransferase (hpt) gene and the Herpes simplex virus thymidine kinase (tk) gene flanked by direct repeats. The direct repeats were inserted to facilitate the excision of the hpt and tk selectable markers and generate a marker-free strain so it can be used as a host to delete a third protease gene.

Spores from AgJg117-3 were plated onto *Trichoderma* minimal medium plates containing 1 µM 5-fluoro-2'-deoxyuridine (FdU) at concentrations of 1×10⁵ and 1×10⁶ and incubated at 28° C. Seventeen isolates were sub-cultured onto *Trichoderma* minimal medium plates containing 1 µM FdU and incubated at 28° C. Of the seventeen isolates, only seven had sporulated; those seven isolates were then sub-cultured onto PDA plates and incubated at 28° C. The seven isolates were then screened for the absence of the hpt and tk markers by fungal spore PCR in the same manner described above.

Southern blot analysis was performed to confirm the deletion of the 25 kDa serine protease gene and the absence of the hpt and tk markers. Genomic DNA was extracted from the deletion strain and *T. reesei* strain SMai-TrSP-30-22 as previously described in Example 10. Two µg of genomic DNA from the deletion strain, *T. reesei* strain SMai-TrSP-30-22, and *T. reesei* strain 981-O-8 were each digested with Hind III and Nco I. *T. reesei* strain 981-O-8 and *T. reesei* strain SMai-TrSP-30-22 were included in the Southern blot as controls. The genomic DNA digestion reaction was composed of 2 µg of genomic DNA, 1 µl of Nco I, 1 µl of Hind III, 3.5 µl of 10×NEB Buffer 2, and water to 35 µl. Both genomic DNA digestions were incubated at 37° C. for approximately 3.5 hours.

The digestions were submitted to 0.8% agarose gel electrophoresis using TAE buffer and blotted onto NYTRAN® SuperCharge blotting membrane using a TURBOBLOTTER® for approximately 5 hours following the manufacturer's recommendations. The membrane was hybridized with a 500 bp digoxigenin-labeled *T. reesei* 25 kDa serine protease probe, which was synthesized by incorporation of digoxigenin-11-dUTP by PCR using primers 069279 (sense) and 069280 (antisense) shown below.

```
Primer 069279 (sense):            (SEQ ID NO: 87)
5'-GGCGCCTCAATCCAGAAGGTCGCAC-3'

Primer 069280 (antisense):        (SEQ ID NO: 88)
5'-GTGTATGTAGTGAAACGAAGCATTCG-3'
```

The amplification reaction was composed of 5 µl of 10× ThermoPol Reaction Buffer, 2.5 µl of PCR DIG Labeling Mix, 1 ng of pAgJg117, 50 pmol of primer 069279, 50 pmol of primer 069280, 2.5 µl of 10 mM dNTPs, 5 units of Taq DNA polymerase, and 35.5 µl of water. The reactions were incubated in an EPPENDORF® MASTERCYCLER® 5333 programmed for 1 cycle at 95° C. for 2 minutes; 30 cycles each at 95° C. for 30 seconds, 55° C. for 30 seconds, and 72° C. for 40 seconds; 1 cycle at 72° C. for 15 minutes; and a 4° C. hold. The PCR reaction product was purified by 1% agarose gel electrophoresis using TAE buffer, excised from the gel, and extracted using a QIAQUICK® Gel Extraction Kit according to the manufacturer's instructions. Incorporation of digoxigenin was indicated by increase in molecular mass.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. The strain containing the 25 kDa serine protease deletion was designated *Trichoderma reesei* AgJg117-3-10A.

Example 27

Construction of a *Trichoderma reesei* Aspartic Protease Gene Deletion Plasmid pAgJg118

The deletion vector pAgJg118 was constructed to delete the *Trichoderma reesei* 42 kDa aspartic protease gene. Plasmid pAgJg118 was generated by first amplifying 5' and 3' flanking regions and cloning them into the vector pCR®2.1-TOPO®. The 5' flanking region contains a 1.5 kb region upstream of the 42 kDa aspartic protease coding region. The 5' flanking region was amplified using primers 068620 (sense) and 068621 (antisense) shown below. Primer 068620 was engineered to contain Asc I and Not I sites on the 5' end of the primer. Primer 068621 was engineered to contain an Asc I site on the 5' end of the primer.

```
Primer 068620 (sense):            (SEQ ID NO: 89)
5'-AAAGGCGCGCCGCGGCCGCTCGCTGTAACGAACTTCTGTCCGCA-3'

Primer 068621 (antisense):        (SEQ ID NO: 90)
5'-AAAGGCGCGCCCTTGAATATCGGAGAAGGTTGCTCACGG-3'
```

The 5' region of the aspartic protease gene was amplified by PCR in a reaction composed of 175 µg of *T. reesei* genomic DNA, 1 µl of PLATINUM® Pfx DNA polymerase, 50 pmol of primer 068620, 50 pmol of primer 068621, 1.5 µl of 10 mM dNTPs, 10 µl of 10×Pfx Amplification buffer, and 33.5 µl of water. The reaction was incubated in an EPPENDORF® MASTERCYCLER® programmed for 1 cycle at 98° C. for 3 minutes; 30 cycles each at 98° C. for 30 seconds, 60° C. for 30 seconds, and 72° C. for 1 minute 30 seconds; 1 cycle at 72° C. for 15 minutes; and a 4° C. hold. A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 µl of the purified PCR fragment, 1 µl of the 10× Thermopol Buffer, 0.5 µl of 10 mM dNTPs, 1 µl of Taq DNA polymerase, and 3 µl of water. The reaction was incubated at 72° C. for 15 minutes. The 5' region of the aspartic protease fragment was cloned into pCR®2.1-TOPO® in a reaction composed of 3 µl of the 5' aspartic protease region PCR fragment, 1 µl of Salt Solution, 1 µl of water, and 1 µl of pCR®2.1-TOPO®. The resulting plasmid was designated 5'Aspartic.

The 3' region of the aspartic protease fragment was cloned into pCR®2.1-TOPO® using primers 068622 (sense) and 068623 (antisense) shown below. Primer 068622 was engineered to contain a Sbf I site on the 5' end of the primer. Primer 068623 was engineered to contain Sbf I and Not I sites on the 5' end of the primer.

```
Primer 068622 (Sense):                    (SEQ ID NO: 91)
AAACCTGCAGGGCGGCGATGGTGGACTTGTTTATGA-3'

Primer 068623 (Antisense):                (SEQ ID NO: 92)
AAACCTGCAGGCGGCCGCAGCAAGTGAGTATCGAGTTTGTAGG-3'
```

The 3' region of the aspartic protease gene was amplified by PCR in a reaction composed of 175 µg of *T. reesei* genomic DNA, 1 µl of PLATINUM® Pfx DNA polymerase, 50 pmol of primer 068622, 50 pmol of primer 068623, 1.5 µl of 10 mM dNTPs, 10 µl of 10×Pfx Amplification buffer, and 33.5 µl of water. The reaction was incubated in an EPPENDORF® MASTERCYCLER® programmed for 1 cycle at 98° C. for 3 minutes; 30 cycles each at 98° C. for 30 seconds, 60° C. for 30 seconds, and 72° C. for 1 minute 30 seconds; 1 cycle at 72° C. for 15 minutes; and a 4° C. hold. A 1.5 kb PCR fragment was purified by 1% agarose gel electrophoresis using TAE buffer, excised from the gel, and extracted using QIAQUICK® Gel Extraction Kit according to the manufacturer's instructions. The gel purified PCR fragment was treated with Taq DNA polymerase to add 3' A-overhangs to the fragment in a reaction composed of 5 µl of the purified PCR fragment, 1 µl of the 10× Thermopol Buffer, 0.5 µl of 10 mM dNTPs, 1 µl of Taq DNA polymerase, and 3 µl of water. The reaction was incubated at 72° C. for 15 minutes. The 3' region of the aspartic protease fragment was cloned into pCR®2.1-TOPO® in a reaction composed of 3 µl of the 3' aspartic protease region PCR fragment, 1 µl of Salt Solution, 1 µl of water, and 1 µl of pCR®2.1-TOPO®. The resulting plasmid was designated 3'Aspartic.

Plasmid 5'Aspartic was digested with Asc I in order to be cloned into Asc I digested plasmid pJfyS1579-41-11 (Example 9) in a reaction composed of 6.45 µg of 5'Aspartic plasmid DNA, 5 µl of Asc I, 10 µl of 10×NEB Buffer 4, and 61 µl of water. The restriction enzyme digestion was incubated at 37° C. for 4 hours. The digestion was purified by 1% agarose gel electrophoresis using TAE buffer, where a 1.5 kb fragment was excised from the gel and extracted using a QIAQUICK® Gel Extraction Kit according to the manufacturer's instructions. The Asc I digested 5'Aspartic fragment was ligated to the Asc I digested pJfyS1579-49-11 in a reaction composed of 307.2 ng of Asc I digested 5'Aspartic, 160 ng of Asc I digested pJfyS1579-49-11, 3 µl of Quick Ligase, 25 µl of 2× Quick Ligase Buffer, and 3 µl of water. The ligation reaction was incubated at room temperature for 15 minutes. The resulting plasmid was designated 5'Aspartic+pJfyS1579.

Figure 23:
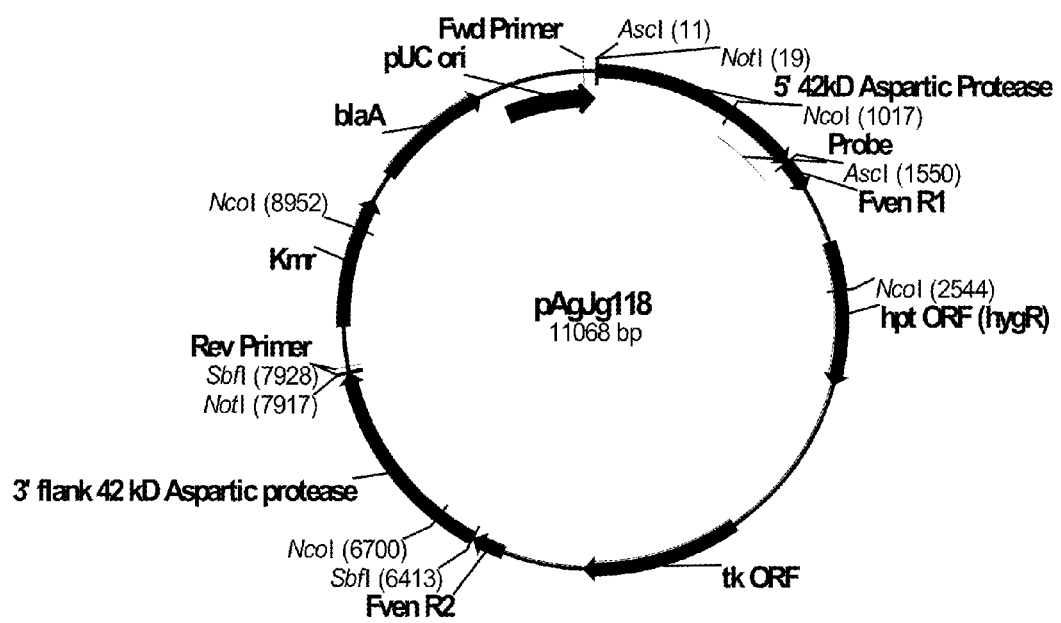
FIG. 23 shows a restriction map of pAgJg118.

To construct plasmid pAgJg118, plasmids 3'Aspartic and 5'Aspartic+pJfyS1579 were digested with Sbf I. The digestions were composed of 3.5 µg of 5'Aspartic+pJfyS1579 or 5.3 µg of 3'Aspartic, 4 µl of Sbf I, 10 µl of 10×NEB Buffer 4, and 56 µl of water. Both digestion reactions were incubated at 37° C. for 1.5 hours. One µl of calf intestinal alkaline phosphatase (CIP) was added to the 5'Aspartic+pJfyS1579 digestion reaction and incubated at 37° C. for an additional hour. A 9.5 kb fragment from 5'Aspartic+pJfyS1579/Sbf I and a 1.5 kb fragment from 3'Aspartic/Sbf I were purified by 0.8% agarose gel electrophoresis using TAE buffer, excised from the gel, and extracted using a QIAQUICK® Gel Extraction Kit according to the manufacturer's instructions. The Sbf I digested 3'Aspartic fragment was ligated to the Sbf I digested 5'Aspartic+pJfyS1579 fragment in a reaction composed of 349.5 ng of Sbf I digested 3'Aspartic, 122.35 ng of Sbf I digested 5'Aspartic+pJfyS1579, 2 µl of Quick Ligase, 20 µl of 2× Quick Ligase Buffer, and 3 µl of water. The ligation reaction incubated at room temperature for 20 minutes and 3 µl of the ligation reaction was transformed into SOLOPACK® Gold Ultracompetent *E. coli* cells according to the manufacturer's instructions. Transformants were selected on 2×YT agar plates supplemented with 100 µg of ampicillin per ml and incubated at 37° C. for 16 hours. The resulting plasmid was designated pAgJg118 (FIG. 23).

Example 28

Generation of a Triple Protease Gene Deletion *Trichoderma reesei* Strain AgJg118-02-2E

*Trichoderma reesei* double protease deletion strain AgJg117-3-10A protoplasts were transformed with Not I-linearized pAgJg118 using the method previously described in Example 12 and plated onto PDA plates plus 1 M sucrose with 10 µg of hygromycin per ml. Six transformants were subcultured onto PDA plates to generate spores.

Possible candidates of *T. reesei* strain AgJg117-3-10A containing the pAgJg118 deletion vector in the 42 kDa aspartic protease locus, thereby deleting the aspartic protease, were screened by fungal spore PCR using the modified protocol of Suzuki et al., 2006, supra. A small amount of spores from each candidate was suspended in 25 µl of TE buffer and heated on high in a microwave oven for 1 minute. The microwaved spore suspension was used as a template in a PCR reaction to screen for the serine protease deletion. The reaction was composed of 1 µl of the spore suspension, 1 µl of 10 mM dNTPs, 12.5 µl of 2× ADVANTAGE® GC-Melt LA Buffer, 25 pmol of primer 069858, 25 pmol of primer 069859, 1.25 units of ADVANTAGE® GC Genomic LA Polymerase Mix, and 9.25 µl water. The reaction was incubated in an EPPENDORF® MASTERCYCLER® programmed for 1 cycle at 95° C. for 10 minutes; 35 cycles each at 95° C. for 30 seconds, 60° C. for 30 seconds, and 72° C. for 5 minutes 30 seconds; 1 cycle at 72° C. for 15 minutes; and a 4° C. hold. Primer 069858 is located at the end of the 5' flanking region and primer 069859 is located at the beginning of the 3' flanking region. If the deletion vector was inserted into the aspartic protease locus, the amplified PCR fragment should be larger than the wild-type fragment since it contains the hpt and tk cassette used to delete the serine protease gene. *Trichoderma reesei* AgJg118-02 was identified in which the aspartic protease had been deleted.

```
Primer 069858 (sense):                    (SEQ ID NO: 93)
5'-TCGGGGAGGATGGCGCAAACCGACCTTCCTAAA-3'

Primer 069859 (antisense):                (SEQ ID NO: 94)
5'-GCACCTTACCCCTACGGACCACGAT-3'
```

The deletion construct pAgJg118 contains the *E. coli* hygromycin phosphotransferase (hpt) gene and the Herpes simplex virus thymidine kinase (tk) gene flanked by direct repeats. The direct repeats were inserted to facilitate the excision of the hpt and tk selectable markers and generate a clean deletion of the 42 kDa aspartic protease.

Spores from *T. reesei* AgJg118-02 were plated onto *Trichoderma* minimal medium plates containing 1 µM 5-fluoro-2'-deoxyuridine (FdU) at concentrations of $1 \times 10^5$ and $1 \times 10^6$ and incubated at 28° C. Ten isolates were sub-cultured onto PDA plates and incubated at 28° C. The ten isolates were then screened for the absence of the hpt and tk markers by fungal spore PCR in the same manner described above.

Southern blot analysis was performed to confirm the deletion of the 42 kDa aspartic protease gene and the absence of the hpt and tk markers. Genomic DNA was extracted from the deletion strain and *T. reesei* strain 981-O-8 as previously described in Example 10. Two µg of genomic DNA from the deletion strain and *T. reesei* strain 981-O-8 were digested with Nco I. *T. reesei* strain 981-O-8 was included in the Southern blot as a control. The genomic DNA digestion reaction was composed of 2 µg of genomic DNA, 1 µl of Nco I, 5 µl of 10×NEB Buffer 3, and water to 50 µl. Both genomic DNA digestions were incubated at 37° C. for approximately 14-16 hours.

The digestions were submitted to 0.8% agarose gel electrophoresis using TAE buffer and blotted onto NYTRAN® SuperCharge blotting membrane using a TURBOBLOTTER® for approximately 12-16 hours following the manufacturer's recommendations. The membrane was hybridized with a 500 bp digoxigenin-labeled *T. reesei* 42 kDa aspartic protease probe, which was synthesized by incorporation of digoxigenin-11-dUTP by PCR using primers 069860 (sense) and 069861 (antisense) shown below.

```
Primer 069860 (sense):                    (SEQ ID NO: 95)
5'-CTTCTATCTTGGGATGCTTCACGATACGTGA-3'

Primer 069861 (antisense):                (SEQ ID NO: 96)
5'-CGCGCCCTTGAATATCGGAGAAGGT-3'
```

The amplification reaction was composed of 5 µl of 10×Taq Buffer, 2.5 µl of PCR DIG Labeling Mix, 5 ng of pAgJg118, 10 pmol of primer 069860, 10 pmol of primer 069861, 2.5 µl of 10 mM dNTPs, 5 units of Taq DNA polymerase, and 36.5 µl of water. The reactions were incubated in an EPPENDORF® MASTERCYCLER® 5333 programmed for 1 cycle at 95° C. for 2 minutes; 30 cycles each at 95° C. for 30 seconds, 56° C. for 30 seconds, and 72° C. for 40 seconds; 1 cycle at 72° C. for 15 minutes; and a 4° C. hold. The PCR reaction product was purified by 1% agarose gel electrophoresis using TAE buffer, excised from the gel, and extracted using a QIAQUICK® Gel Extraction Kit according to the manufacturer's instructions. Incorporation of digoxigenin was indicated by increase in molecular mass.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions. The strain containing the aspartic protease deletion was designated *Trichoderma reesei* AgJg118-02-2E.

Example 29

Fermentation of *Trichoderma reesei* AgJg117-3-10a and *Trichoderma reesei* AgJg118-02-2E Spores of *Trichoderma reesei* AgJg117-3-10A and *Trichoderma reesei* AgJg118-02-2E from PDA plates were inoculated into 500 ml shake flasks, containing 100 ml of Shake Flask Medium. *Trichoderma reesei* strain 981-O-8 was run as a control under the same conditions. The flasks were placed into an orbital shaker at 28° C. for approximately 48 hours at which time 50 ml of the culture was added to an APPLIKON® three liter glass jacketed fermentor (Applikon Biotechnology, Inc., Foster City Calif. USA) that contains 1.8 liters of Fermentation Batch Medium. Fermentation Feed Medium was dosed at a rate of 0 to 4 g/l/hour for a period of 185 hours. The fermentation vessel was maintained at a temperature of 28° C. and pH was controlled using an APPLIKON® 1030 control system (Applikon Biotechnology, Inc., Foster City Calif. USA) to a set-point of 4.5+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered and stored at 5 to 10° C.

Example 30

Preparation of *Aspergillus aculeatus* strain CBS 186.67 GH3 Beta-Xylosidase

The *Aspergillus aculeatus* strain CBS 186.67 GH3 beta-xylosidase was recombinantly prepared according to the following procedure.

To generate genomic DNA for PCR amplification, *Aspergillus aculeatus* CBS 186.67 was propagated on PDA agar plates by growing at 26° C. for 7 days. Spores harvested from the PDA plates were inoculated into 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, Calif., USA). Briefly, a FastDNA® SPIN Kit for Soil (Qbiogene, Inc., Carlsbad, Calif., USA) was used in a FastPrep® 24 Homogenization System (MP Biosciences, Santa Ana, Calif., USA). Two ml of fungal material were harvested by centrifugation at 14,000×g for 2 minutes. The supernatant was removed and the pellet resuspended in 500 µl of deionized water. The suspension was transferred to a Lysing Matrix E FastPrep® tube (Qbiogene, Inc., Carlsbad, Calif., USA) and 790 µl of sodium phosphate buffer and 100 µl of MT buffer from the FastDNA® SPIN Kit were added to the tube. The sample was then secured in a FastPrep® Instrument (Qbiogene, Inc., Carlsbad, Calif., USA) and processed for 60 seconds at a speed of 5.5 m/sec. The sample was then centrifuged at 14,000×g for two minutes and the supernatant transferred to a clean EPPENDORF® tube. A 250 µl volume of PPS reagent from the FastDNA® SPIN Kit was added and then the sample was mixed gently by inversion. The sample was again centrifuged at 14,000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 µl volume of the supernatant was removed and discarded and then the remaining sample was resuspended in the matrix. The sample was then transferred to a SPIN filter tube from the FastDNA® SPIN Kit and centrifuged at 14,000×g for 1 minute. The catch tube was emptied and the remaining matrix suspension added to the SPIN filter tube. The sample was again centrifuged (14,000×g, 1 minute). A 500 µl volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14000×g for 2 minutes to "dry" the matrix of residual SEWS-M wash solution. The SPIN filter was placed in a fresh catch tube and allowed to air dry for 5 minutes at room temperature. The matrix was gently resuspended in 100 µl of DES (DNase/Pyrogen free water) with a pipette tip. The unit was centrifuged (14,000×g, 1 minute) to elute the genomic DNA followed by elution with 100 µl of 10 mM Tris, 0.1 mM EDTA, pH 8.0 by renewed centrifugation at 14000×g for 1 minute and the eluates were combined. The concentration of the DNA harvested from the catch tube was measured by a UV spectrophotometer at 260 nm.

The *Aspergillus aculeatus* beta-xylosidase gene was isolated by PCR using two cloning primers GH3-101f and GH3-101r, shown below, which were designed based on the publicly available *Aspergillus aculeatus* xyl2 full-length sequence (GenBank AB462375.1) for direct cloning using the IN-FUSION™ strategy.

```
Primer GH3-101f:                      (SEQ ID NO: 97)
5'-acacaactggggatccaccatggctgtggcggctcttgctctgc
tgg-3'

Primer GH3-101r:                      (SEQ ID NO: 98)
5'-agatctcgagaagcttaCTCATCCCCGCCACCCCTGCACCTC
C-3'
```

A PCR reaction was performed with genomic DNA prepared from *Aspergillus aculeatus* CBS 186.67 in order to amplify the full-length gene. The PCR reaction was composed of 1 µl of genomic DNA, 0.75 µl of primer GH3-101.1f (10 µM), 0.75 µl of primer GH3-101.1r (10 µM), 3 µl of 5×HF buffer (Finnzymes Oy, Finland), 0.25 µl of 50 mM $MgCl_2$, 0.3 µl of 10 mM dNTP, 0.15 µl of PHUSION® DNA polymerase (New England Biolabs, Ipswich, Mass., USA), and PCR-grade water up to 15 µl. The PCR reaction was performed using a DYAD® PCR machine (Bio-Rad Laboratories, Inc., Hercules, Calif., USA) programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.4 kb PCR product band was excised from the gel and purified using a GFX® PCR DNA and Gel Band Purification Kit (GE Healthcare Life Sciences, Piscataway, N.J., USA) according to manufacturer's instructions. DNA corresponding to the *Aspergillus aculeatus* beta-xylosidase gene was cloned into the expression vector pDAu109 (WO 2005042735) linearized with Bam HI and Hind III, using an IN-FUSION™ Dry-Down PCR Cloning Kit (BD Biosciences, Palo Alto, Calif., USA) according to the manufacturer's instructions.

A 2.5 µl volume of the diluted ligation mixture was used to transform ONE SHOT® chemically competent TOP10 cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit (Omega Bio-Tek, Inc., Norcross, Ga., USA) according to the manufacturer's instructions. The *Aspergillus aculeatus* beta-xylosidase gene sequence was verified by Sanger sequencing before heterologous expression.

The coding sequence is 2454 bp including the stop codon. The gene does not contain introns. The encoded predicted protein is 817 amino acids. Using the SignalP program (Nielsen et al., 1997, *Protein Engineering* 10: 1-6), a signal peptide of 17 residues was predicted. The predicted mature protein contains 800 amino acids.

Protoplasts of *Aspergillus oryzae* MT3568 were prepared as described in WO 95/02043. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene. One hundred microliters of protoplast suspension were mixed with 2.5-15 µg of the *Aspergillus* expression vector and 250 µl of 60% PEG 4000, 10 mM $CaCl_2$, and 10 mM Tris-HCl pH 7.5 were added and gently mixed. The mixture was incubated at 37° C. for 30 minutes and the protoplasts were spread on COVE sucrose (1 M) plates (Cove, 1996, *Biochim. Biophys. Acta* 133: 51-56) supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aculeatus aculeatus* beta-xylosidase. The screening was based on intensity of the band corresponding to the heterologous expressed protein determined by SDS-PAGE and activity of the enzyme on 4-nitrophenyl-beta-D-xylopyranoside (pNPX) as follows. Ten µl of culture broth was mixed with 90 µl of assay reagent containing 10 µl of 0.1% TWEEN® 20, 10 µl of 1 M sodium citrate pH 5, 4 µl of 100 mM of pNPX substrate (Sigma Aldrich, St. Louis, Mo., USA) solubilized in DMSO (0.4% final volume in stock solution), and filtered water. The assay was performed for 30 minutes at 37° C. and absorbance determined at 405 nm before and after addition of 100 µl of 1 M sodium carbonate pH 10. The highest absorbance values at 405 nm were correlated to the SDS-PAGE data for selection of the best transformant.

Spores of the best transformant designated *A. oryzae* EXP3611 were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-4C-1 medium for 4 days at 30° C. with shaking at 100 rpm. The fermentation broth was filtered using standard methods.

Protein concentration was determined using a Microplate BCA™ Protein Assay Kit (Thermo Fischer Scientific, Waltham, Mass., USA) in which bovine serum albumin was used as a protein standard.

Example 31

Storage Stability of Broths from *Trichoderma reesei* AgJg117-3-10A and *Trichoderma reesei* AgJg118-02-2E at Elevated Temperatures The broths of *Trichoderma reesei* AgJg117-3-10A, *Trichoderma reesei* AgJg118-02-2E, and *Trichoderma reesei* strain 981-O-8 (control) were evaluated for storage stability at elevated temperatures and compared to the stability of the parent strain. Fermentation broths obtained from Example 29 were sterile filtered (0.2 µM syringe filter, polyethersulfone membrane, GE Healthcare, Piscataway, N.J., USA), aliquoted into 1.8 mL Nunc CRYOTUBE™ Vials (Thermo Fisher Scientific, Waltham, Mass., USA) and flash frozen in liquid nitrogen. Vials were then stored at 40° C. or −80° C. (as a control) for two weeks. Following incubation, the samples were assayed for PCS hydrolysis activity.

Hydrolysis of PCS was conducted using 2.2 ml deep-well plates (Axygen, Union City, Calif., USA) in a total reaction volume of 1.0 ml. The hydrolysis was performed with 50 mg of PCS per ml of 50 mM sodium acetate pH 5.0 buffer containing 1 mM manganese sulfate and a dose response of the protease deletion strains and the parent strain (2, 4, 8, and 12 mg per gram of cellulose). Each reaction was supplemented with 5% addition by protein of an *Aspergillus aculeatus* beta-glucosidase (Example 30). Hydrolysis assays were performed in triplicate for 72 hours at 50° C. Following hydrolysis, samples were filtered with a 0.45 µm Multiscreen 96-well filter plate (Millipore, Bedford, Mass., USA) and filtrates analyzed for sugar content as described below.

Sugar concentrations of samples diluted in 0.005 M $H_2SO_4$ were measured after elution by 0.005 M $H_2SO_4$ with 0.05% w/w benzoic acid at a flow rate of 0.6 mL/min from a 4.6×250 mm AMINEX® HPX-87H column (Bio-Rad Laboratories, Inc., Hercules, Calif., USA) at 65° C. with quantitation by integration of glucose and cellobiose signal from refractive index detector (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction.

The degree of cellulose conversion was calculated using the following equation: % conversion=[glucose concentration+1.053×(cellobiose concentration)]/[(glucose concentration+1.053×(cellobiose concentration) in a limit digest]. The 1.053 factor for cellobiose takes into account the increase in mass when cellobiose is converted to glucose. Sixty mg of the *T. reesei* cellulolytic protein preparation per g of cellulose was used for the limit digest.

Figure 24:
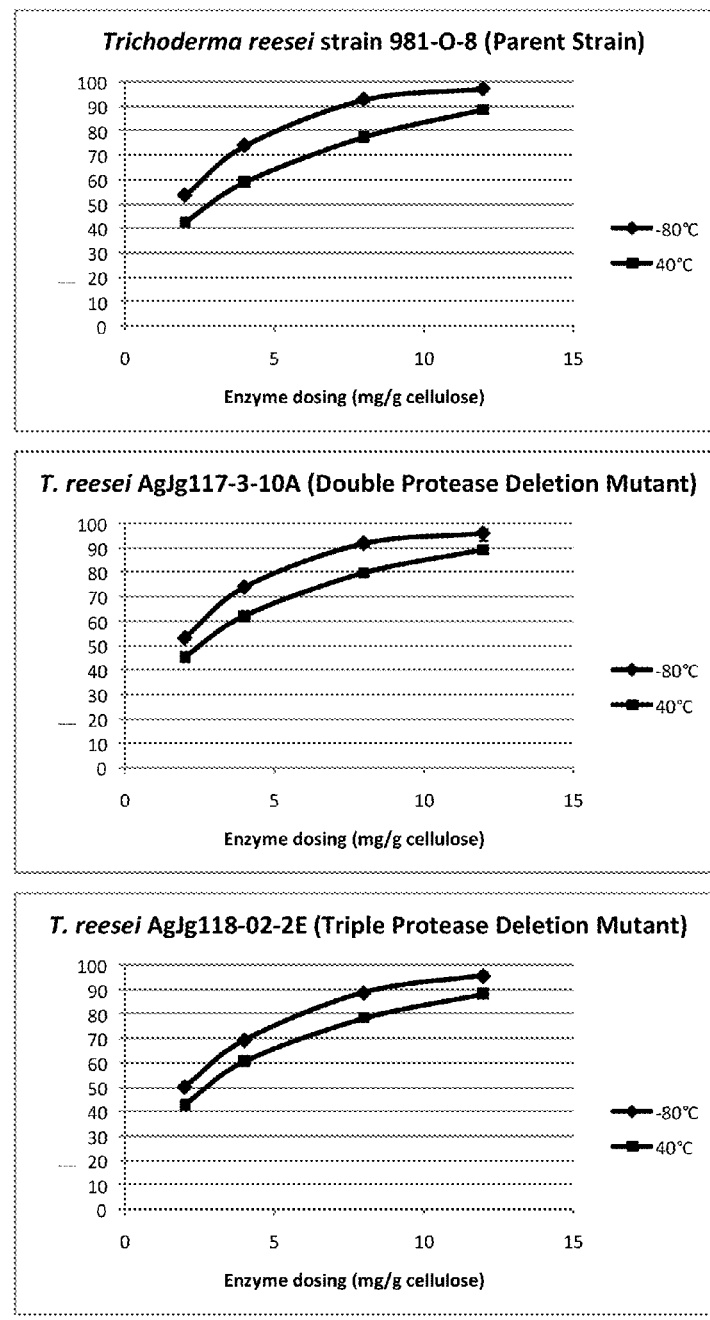
FIG. 24 shows residual cellulase activity at 40° C. for two weeks of the broths from *Trichoderma reesei* AgJg117-3-10A (double protease deletion mutant) and *Trichoderma reesei* AgJg118-02-2E (triple protease deletion mutant) compared to the broth of the parent strain *Trichoderma reesei* strain 981-O-8 under the same conditions.

The results shown in FIG. 24 demonstrated that residual cellulase activity at 40° C. for two weeks of the broths from *Trichoderma reesei* AgJg117-3-10A and *Trichoderma reesei* AgJg118-02-2E were superior compared to the broth of the *Trichoderma reesei* strain 981-O-8 under the same conditions. To reach 80% conversion of the substrate required a 1.76 fold increase in protein loading for the parent strain with the sample incubated at 40° C. as compared to the control sample incubated at −80° C. Under the same conditions, there is 1.43 and 1.61 fold increase in protein loading for the triple and double protease deletion strain broths, respectively. Consequently, the triple protease deletion strain broth showed a 19% improvement in storage stability for two weeks at 40° C. The double protease deletion broth showed an 8.5% improvement when stored at 40° C. for two weeks.

Example 32

Generation of the Subtilisin-Like Serine Protease Deletion Vector pJfyS152

The 5' flanking sequence of the *T. reesei* 981-O-8 subtilisin-like serine protease (pepC) gene (SEQ ID NO: 99 for the DNA sequence and SEQ ID NO: 100 for the deduced amino acid sequence) was amplified using PHUSION® Hot Start High-Fidelity DNA Polymerase (New England Biolabs, Ipswich, Mass., USA) and gene-specific forward and reverse primers shown below. The underlined portion is an Asc I site introduced for cloning and the region in italics represents an introduced extension corresponding to a homologous region of the site of vector insertion necessary for IN-FUSION® Cloning (Clontech, Palo Alto, Calif., USA).

Forward primer:                           (SEQ ID NO: 101)
5'-*tcacatggtttaaac*ggcgcgccGGTACTATATTAGAAAGGGGTTC
C-3'

Reverse primer:                           (SEQ ID NO: 102)
5'-*agccttgttttgtc*ggcgcgccGAAGAAGAGAAGAGGAGGAGGAT
G-3'

The amplification reaction contained 150 ng of *T. reesei* 981-O-8 genomic DNA, 200 µm dNTP's, 0.4 µM primers, 1× PHUSION® GC Buffer (New England Biolabs, Ipswich, Mass., USA), and 2 units of PHUSION® DNA polymerase in a final volume of 50 µl. The amplification reaction was incubated in an EPPENDORF® MASTERCYCLER® programmed for 1 cycle at 98° C. for 2 minutes; 30 cycles each at 98° C. for 30 seconds, 57° C. for 30 seconds, and 72° C. for 1 minute 30 seconds; and one cycle at 72° C. for 7 minutes. PCR products were separated by 1% agarose gel electrophoresis using TAE buffer and a 2.2 kb fragment was excised and agarose was extracted using a NUCLEOSPIN® Extract II Kit (Machery-Nagel, Dueren, Germany) according to the manufacturer's protocol.

The 2.2 kb PCR product was inserted into Asc I-digested pJfyS1579-41-11 (Example 9) using an IN-FUSION® ADVANTAGE® PCR Cloning Kit (Clontech, Palo Alto, Calif., USA) according to the manufacturer's protocol. The IN-FUSION® reaction contained 1×IN-FUSION® Reaction buffer (Clontech, Palo Alto, Calif., USA), 150 ng of pJfyS1579-41-11, 100 ng of PCR product, and 1 µl of IN-FUSION® Enzyme (Clontech, Palo Alto, Calif., USA) in a 10 µl reaction volume. The reaction was incubated for 15 minutes at 37° C. and 15 minutes at 50° C. To the reaction 40 µl of TE were added. Two 2 µl were used to transform ONE SHOT® TOP10 competent cells according to the manufacturer's protocol. Transformants were screened by sequencing and one clone containing the insert with no PCR errors was identified and named pJfyS152A. Plasmid pJfyS152A was used to insert the 3' flank of the pepC gene.

The 3' pepC flanking sequence was amplified from *T. reesei* 981-O-8 genomic DNA (Example 13) using PHUSION® Hot Start High-Fidelity DNA Polymerase and gene-specific forward and reverse primers shown below. The underlined portion is a Sbf I site introduced for cloning and the region in italics represents an introduced extension corresponding to a homologous region of the site of vector insertion necessary for IN-FUSION® Cloning, and the bold portion is an introduced Pme I site for later removal of the bacterial propagation portion of the plasmid Forward Primer: (SEQ ID NO: 103)
5'-cctagttggagtattcctgcagggTCTATCTCTTTTGAGTAGTCCCC
A-3'

Reverse primer: (SEQ ID NO: 104)
5'-tggccatatttaaatcctgcagggtttaaacAGCTAGTGACTCGCG
ATTTATCGT-3'

The amplification reaction contained 150 ng of *T. reesei* 981-O-8 genomic DNA, 200 µm dNTP's, 0.4 µM primers, 1× PHUSION® HF Buffer (New England Biolabs, Ipswich, Mass., USA) with 5 mM MgCl$_2$, and 2 units of PHUSION® DNA polymerase in a final volume of 50 µl. The amplification reaction was incubated in an EPPENDORF® MASTERCYCLER® programmed for 1 cycle at 98° C. for 2 minutes; 30 cycles each at 98° C. for 30 seconds, 56° C. for 30 seconds, and 72° C. for 1 minute 30 seconds; and one cycle at 72° C. for 7 minutes. PCR products were separated by 1% agarose gel electrophoresis using TAE buffer where a 2.2 kb fragment was excised and agarose was extracted using a NUCLEOSPIN® Extract II Kit according to the manufacturer's protocol.

Figure 25:
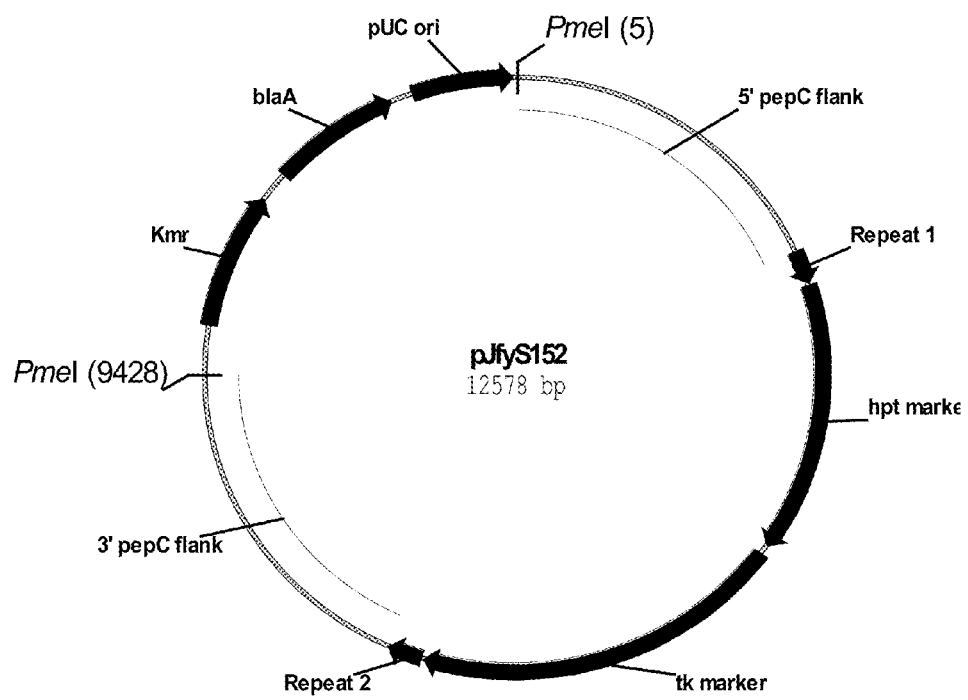
FIG. 25 shows a restriction map of pJfyS152.

The 2.2 kb PCR product was inserted into Sbf I-digested pJfyS152A using an IN-FUSION® ADVANTAGE® PCR Cloning Kit according to the manufacturers protocol. The IN-FUSION® reaction contained 1×IN-FUSION® Reaction buffer, 150 ng of pJfyS1579-41-11, 100 ng of the PCR product, and 1 µl of IN-FUSION® Enzyme in a 10 µl reaction volume. The reaction was incubated for 15 minutes at 37° C. and 15 minutes at 50° C. To the reaction 40 µl of TE were added and 2 µl was used to transform ONE SHOT® TOP10 competent cells according to the manufacturer's protocol. Transformants were screened by sequencing and one clone containing the insert with no PCR errors was identified and designated pJfyS152 (FIG. 25). Plasmid pJfyS152 was used to delete the pepC gene.

Example 33

Generation of Subtilisin-Like Serine
Protease-Deleted *Trichoderma reesei* Strain
*JfyS*152-1

Six transformants of *T. reesei* AgJg115-104-7B1 (Example 23) transformed with Pme I-digested and gel-purified pJfyS152 according to the procedure described in Example 12, were transferred from transformation plates with sterile inoculation loops to new plates containing PDA medium and grown at 28° C. for 7 days. All 6 transformants were then analyzed by Southern analysis. Genomic DNA from each of the 6 transformants was extracted as described in Example 21 and 2.5 µg of each were digested with 20 units of Nsi II and 20 units of Bgl II for 16 hours. Digestions were subjected to 0.9% agarose gel electrophoresis and blotted onto NYT-RAN® SuperCharge blotting membrane using a TURBOB-LOTTER® for approximately 12-16 hours following the manufacturer's recommendations. A PCR probe, hybridizing to the 3' flanking sequence of the pepC gene, was generated using a PCR DIG Probe Synthesis Kit according to the manufacturer's protocol with the following forward and reverse primers:

Forward primer: (SEQ ID NO: 105)
5'-TGATTTCGTGGACAGCGTTTCTCGC-3'

Reverse primer: (SEQ ID NO: 106)
5'-TTGCCTTACAGCTGGCAACAATGGCGTC-3'

The amplification reaction was incubated in an EPPENDORF® MASTERCYCLER® programmed for 1 cycle at 95° C. for 2 minutes; 30 cycles each at 94° C. for 30 seconds, 59° C. for 30 seconds, and 72° C. for 40 seconds, and one cycle at 72° C. for 7 minutes. PCR products were separated by 1% agarose gel electrophoresis using TAE buffer and a 0.3 kb fragment was excised and agarose was extracted using a NUCLEOSPIN® Extract II Kit according to the manufacturer's protocol. The incorporation of digoxygenin was confirmed by the molecular weight shift of the labelled probe which ran at approximately 0.5 kb.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions Southern analysis indicated that 3 of the 6 transformants harbored the deletion cassette in a single copy. The strain containing the pepC deletion was designated *Trichoderma reesei* JfyS152-1.

Example 34

Generation of the Pepsin-Like Aspartic Protease
Deletion Vector pJfyS153

The 5' flanking sequence of the *Trichoderma reesei* 981-O-8 pepsin-like aspartic protease gene (SEQ ID NO: 107 for the DNA sequence and SEQ ID NO: 108 for the deduced amino acid sequence) was amplified using PHUSION® Hot Start High-Fidelity DNA Polymerase New England Biolabs, Ipswich, Mass., USA) and gene-specific forward and reverse primers shown below. The underlined portion is an Asc I site introduced for cloning and the region in italics represents vector homology to the site of insertion for IN-FUSION®.

Forward primer: (SEQ ID NO: 109)
5'-*tcacatggtttaaac*ggcgcgccTTCCGGCTTCTTTTTATGTATAC
CT-3'

Reverse primer: (SEQ ID NO: 110)
5'-*agccttgttttgtc*ggcgcgccAAGCTAGGAACCAGCCTCTTTGT
A-3'

The amplification reaction contained 150 ng of *Trichoderma reesei* 981-O-8 genomic DNA, 200 µm dNTP's, 0.4 µM primers, 1× PHUSION® GC Buffer (New England Biolabs, Ipswich, Mass., USA) and 2 units of PHUSION® DNA polymerase (New England Biolabs, Ipswich, Mass., USA) in a final volume of 50 µl.

The amplification reaction was incubated in an EPPENDORF® MASTERCYCLER® programmed for 1 cycle at 95° C. for 2 minutes; 30 cycles each at 95° C. for 30 seconds, 57° C. for 30 seconds, and 72° C. for 1 minute 30 seconds; and one cycle at 72° C. for 7 minutes.

PCR products were separated by 1% agarose gel electrophoresis using TAE buffer and a 2.2 kb fragment was excised and agarose was extracted using a NUCLEOSPIN® Extract II Kit according to the manufacturer's protocol.

The 2.2 kb PCR product was inserted into Asc I-digested pJfyS1579-41-11 using an IN-FUSION® ADVANTAGE® PCR Cloning Kit according to the manufacturer's protocol. The IN-FUSION® reaction contained 1×IN-FUSION® Reaction buffer, 150 ng pJfyS1579-41-11, 100 ng PCR product and 1 µl IN-FUSION® Enzyme in a 10 µl reaction volume. The reaction was incubated for 15 minutes at 37° C. and 15 minutes at 50° C. To the reaction 40 µl of TE were added and 2 µl used to transform ONE SHOT® TOP 10 competent cells according to the manufacturer's protocol. Transformants were screened by sequencing and one clone containing the insert with no PCR errors was identified and designated pJfyS153A, and was used as the plasmid to insert the 3' flank of the pepsin-like aspartic protease gene.

The 3' flanking sequence of the pepsin-like aspartic protease gene was amplified from *Trichoderma reesei* 981-O-8 genomic DNA (Example 13) using PHUSION® Hot Start High-Fidelity DNA Polymerase (New England Biolabs, Ipswich, Mass., USA) and gene-specific forward and reverse primers shown below. The underlined portion is a Sbf I site introduced for cloning and the region in italics represents vector homology to the site of insertion for IN-FUSION®, and the bold portion is an introduced Pme I site for later removal of the bacterial propagation portion of the plasmid.

(SEQ ID NO: 111)
5'-*ctagttggagtatt*cctgcaggaGCCGAGCTCCTGAACGCTGAGAT
T-3'

Reverse primer: (SEQ ID NO: 112)
5'-*tggccatatttaaat*cctgcagGTTTAAACGAGGGAAAAGGGCCGC
TGCACGAT-3'

The amplification reaction contained 150 ng of *Trichoderma reesei* 981-O-8 genomic DNA, 200 µm dNTP's, 0.4 µM primers, 1× PHUSION® HF Buffer with 5 mM MgCl₂, and 2 units of PHUSION® DNA polymerase in a final volume of 50 µl.

The amplification reaction was incubated in an EPPENDORF® MASTERCYCLER® programmed for 1 cycle at 95° C. for 2 minutes; 30 cycles each at 95° C. for 30 seconds, 59° C. for 30 seconds, and 72° C. for 1 minute 30 seconds; and one cycle at 72° C. for 7 minutes.

PCR products were separated by 1% agarose gel electrophoresis using TAE buffer and a 1.5 kb fragment was excised and agarose was extracted using a NUCLEOSPIN® Extract II Kit according to the manufacturer's protocol.

Figure 26:
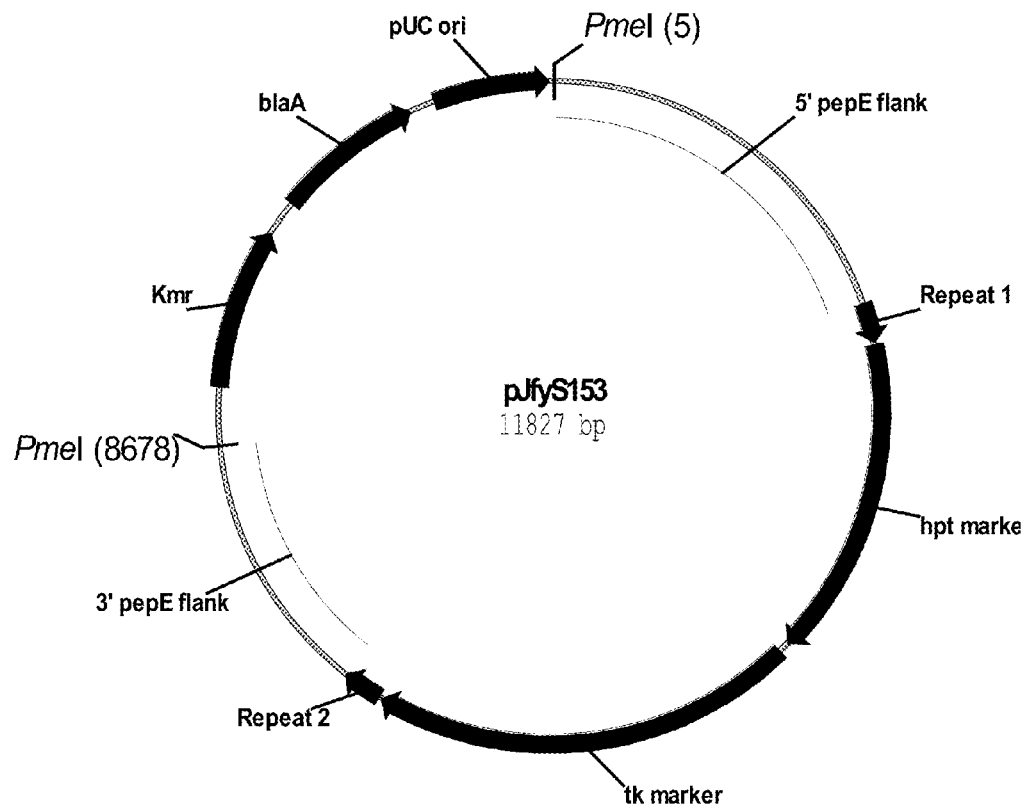
FIG. 26 shows a restriction map of pJfyS153.

The 1.5 kb PCR product was inserted into Sbf I-digested pJfyS153A using an IN-FUSION® ADVANTAGE® PCR Cloning Kit according to the manufacturer's protocol. The IN-FUSION® reaction contained 1×IN-FUSION® Reaction buffer, 150 ng of pJfyS1579-41-11, 100 ng of PCR product, and 1 µl of IN-FUSION® Enzyme in a 10 µl reaction volume. The reaction was incubated for 15 minutes at 37° C. and 15 minutes at 50° C. To the reaction 40 µl of TE were added and 2 µl used to transform ONE SHOT® TOP 10 competent cells according to the manufacturer's protocol (Invitrogen, Carlsbad, Calif., USA). Transformants were screened by sequencing and one clone containing the insert with no PCR errors was identified and designated pJfyS153 (FIG. 26), and was used to delete the pepsin-like aspartic protease gene.

Example 35

Generation of Pepsin-Like Aspartic Protease-Deleted *Trichoderma reesei* Strain JfyS153-6

Sixteen transformants of *Trichoderma reesei* AgJg115-104-7B1 (described in Example 23) were obtained when protoplasts were transformed with Pme I-digested and gel-purified pJfyS152 according to the procedure described in Example 12. All 16 were transferred from transformation plates with sterile inoculation loops to new plates containing PDA medium and grown at 28° C. for 4 days. The 16 transformants were analyzed by fungal spore PCR according to the method described in Example 23 with the following primers:

| Forward Primer:<br>5'-CGCGGAGGTGAGGTGTTGATGATG-3' | (SEQ ID NO: 113) |
|---|---|
| Reverse Primer 1 (wild-type):<br>5'-CGGCGGTCTTTAAGGTGATGTCGC-3' | (SEQ ID NO: 114) |
| Reverse Primer 2 (deleted):<br>5'-GTTTCAGGCAGGTCTTGCAACG-3' | (SEQ ID NO: 115) |

The reaction was incubated in an EPPENDORF® MASTERCYCLER® programmed for 1 cycle at 98° C. for 5 minutes; 35 cycles each at 98° C. for 20 seconds, 53° C. for 30 seconds, and 72° C. for 3 minutes 30 seconds; 1 cycle at 72° C. for 7 minutes; and a 4° C. hold. PCR reactions were subjected to 1% Agarose Gel electrophoresis in TAE buffer.

The PCR primers were designed so that if the wild-type gene was intact the Forward and Reverse Primer 1 would anneal resulting in a 2.5 kb fragment and if the gene was deleted the Forward and Reverse Primer 2 would anneal resulting in a 3.5 kb fragment. The fungal spore PCR suggested that only one of the 16 transformants contained the deletion showing only the 3.5 kb fragment. This strain was subsequently analyzed by Southern analysis.

Genomic DNA was extracted as described in Example 21 and 2 µg were digested with 21.4 units of Nco I and 21.4 units of Bgl II for 16 hours. Digestions were subjected to 0.9% agarose gel electrophoresis in TAE buffer and blotted onto NYTRAN® SuperCharge blotting membrane using a TURBOBLOTTER® for approximately 12-16 hours following the manufacturer's recommendations. A PCR probe, hybridizing to the 3' flanking sequence of the pepsin-like aspartic protease gene, was generated using a PCR DIG Probe Synthesis Kit according to the manufacturer's protocol (Roche Diagnostics, Indianapolis, Ind.) with the following forward and reverse primers:

| Forward primer:<br>5'-GAAGACAGTCCTACTGCTGCGGAG-3' | (SEQ ID NO: 116) |
|---|---|
| Reverse primer:<br>5'-GTAGCTCTCCCCGTATAATGCAGG-3' | (SEQ ID NO: 117) |

The amplification reaction was incubated in an EPPENDORF® MASTERCYCLER® programmed for 1 cycle at 95° C. for 2 minutes; 30 cycles each at 95° C. for 20 seconds, 57° C. for 30 seconds, and 72° C. for 40 seconds; and one cycle at 72° C. for 7 minutes.

PCR products were separated by 1.2% agarose gel electrophoresis using TAE buffer and a 0.6 kb fragment was excised and agarose was extracted using a Nucleospin Extract II® Kit according to the manufacturer's protocol. The incorporation of digoxygenin was confirmed by the molecular weight shift of the labelled probe which ran at approximately 0.6 kb.

Hybridization was performed in DIG Easy Hyb buffer at 42° C. for 15-17 hours. The membrane was then washed under high stringency conditions in 2×SSC plus 0.1% SDS for 5 minutes at room temperature followed by two washes in 0.5×SSC plus 0.1% SDS for 15 minutes each at 65° C. The probe-target hybrids were detected by chemiluminescent assay (Roche Molecular Biochemicals, Indianapolis, Ind., USA) following the manufacturer's instructions.

Southern analysis indicated that the strain harbored the deletion cassette in a single copy at the intended locus. The strain containing the pepsin-like protease deletion was designated *Trichoderma reesei* JfyS153-6.

The present invention is further described by the following numbered paragraphs:

[1] A mutant of a parent *Trichoderma* strain, comprising a polynucleotide encoding a polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions.

[2] The mutant of paragraph 1, which comprises a modification of the first subtilisin-like serine protease gene.

[3] The mutant of paragraph 1 or 2, which comprises a modification of the first aspartic protease gene.

[4] The mutant of any of paragraphs 1-3, which comprises a modification of the trypsin-like serine protease gene.

[5] The mutant of any of paragraphs 1-4, which comprises a modification of the second subtilisin-like serine protease gene.

[6] The mutant of any of paragraphs 1-5, which comprises a modification of the second aspartic protease gene.

[7] The mutant of paragraph 1-6, which comprises a modification of the first subtilisin-like serine protease gene, the first aspartic protease gene, the trypsin-like serine protease gene, the second subtilisin-like serine protease gene, and the second aspartic protease gene.

[8] The mutant of any of paragraphs 1-7, wherein the polypeptide is native or foreign to the *Trichoderma* strain.

[9] The mutant of any of paragraphs 1-8, wherein the *Trichoderma* strain is selected from the group consisting of *Trichoderma harzianum, Trichoderma koningii, Trichoderma longibrachiatum, Trichoderma reesei*, and *Trichoderma viride*.

[10] The mutant of any of paragraphs 1-9, wherein the *Trichoderma* strain is *Trichoderma reesei*.

[11] The mutant of any of paragraphs 1-10, which produces at least 25% less of the one or more (several) enzymes selected from the group consisting of the first subtilisin-like serine protease, the first aspartic protease, the trypsin-like serine protease, the second subtilisin-like serine protease, and the second aspartic protease compared to the parent *Trichoderma* strain when cultivated under identical conditions.

[12] The mutant of any of paragraphs 1-10, which is completely deficient in the one or more (several) enzymes selected from the group consisting of the first subtilisin-like serine protease, the first aspartic protease, the trypsin-like serine protease, the second subtilisin-like serine protease, and the second aspartic protease compared to the parent *Trichoderma* strain when cultivated under identical conditions.

[13] The mutant of any of paragraphs 1-12, wherein the first subtilisin-like serine protease gene is selected from the group consisting of: (a) polypeptide comprising or consisting of an amino acid sequence having at least 60%, e.g., at least 65%, at least 70%, at least 75%, at least 80%, at least 85%, at least 90%, at least 95%, or 100% sequence identity to SEQ ID NO: 2 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 1; (ii) the mature polypeptide coding sequence of SEQ ID NO: 1, (iii) the cDNA sequence of (i) or (ii), or (iv) a full-length complementary strand of (i), (ii), or (iii); and (c) a polypeptide encoded by a polynucleotide comprising or consisting of a nucleotide sequence having at least 60%, e.g., at least 65%, at least 70%, at least 75%, at least 80%, at least 85%, at least 90%, at least 95%, or 100% sequence identity to SEQ ID NO: 1 or the cDNA thereof, or the mature polypeptide coding sequence thereof.

[14] The mutant of any of paragraphs 1-13, wherein the first subtilisin-like serine protease comprises or consists of SEQ ID NO: 2 or the mature polypeptide thereof.

[15] The mutant of any of paragraphs 1-14, wherein the first aspartic protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 4 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 3; (ii) the mature polypeptide coding sequence of SEQ ID NO: 3, (iii) the cDNA sequence of (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 3 or the cDNA thereof, or the mature polypeptide coding sequence thereof.

[16] The mutant of any of paragraphs 1-15, wherein the first aspartic protease comprises or consists of SEQ ID NO: 4 or the mature polypeptide thereof.

[17] The mutant of any of paragraphs 1-16, wherein the trypsin-like serine protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 6 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 5; (ii) the mature polypeptide coding sequence of SEQ ID NO: 5, (iii) the cDNA sequence contained in (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 5 or the cDNA thereof, or the mature polypeptide coding sequence thereof.

[18] The mutant of any of paragraphs 1-17, wherein the trypsin-like serine protease comprises or consists of SEQ ID NO: 6 or the mature polypeptide thereof.

[19] The mutant of any of paragraphs 1-18, wherein the second subtilisin-like serine protease gene is selected from the group consisting of: (a) a polypeptide comprising or consisting of an amino acid sequence having at least 60%, e.g., at least 65%, at least 70%, at least 75%, at least 80%, at least 85%, at least 90%, at least 95%, or 100% sequence identity to SEQ ID NO: 100 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 99; (ii) the mature polypeptide coding sequence of SEQ ID NO: 99, (iii) the cDNA sequence of (i) or (ii), or (iv) a full-length complementary strand of (i), (ii), or (iii); and (c) a polypeptide encoded by a polynucleotide comprising or consisting of a nucleotide sequence having at least 60%, e.g., at least 65%, at least 70%, at least 75%, at least 80%, at least 85%, at least 90%, at least 95%, or 100% sequence identity to SEQ ID NO: 100 or the cDNA thereof, or the mature polypeptide coding sequence thereof.

[20] The mutant of any of paragraphs 1-19, wherein the second subtilisin-like serine protease comprises or consists of SEQ ID NO: 100 or the mature polypeptide thereof.

[21] The mutant of any of paragraphs 1-20, wherein the second aspartic protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 108 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 3; (ii) the mature polypeptide coding sequence of SEQ ID NO: 107, (iii) the cDNA sequence of (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 107 or the cDNA thereof, or the mature polypeptide coding sequence thereof.

[22] The mutant of any of paragraphs 1-21, wherein the second aspartic protease comprises or consists of SEQ ID NO: 108 or the mature polypeptide thereof.

[23] A method of producing a polypeptide, comprising: cultivating a mutant of a parent *Trichoderma* strain in a medium for the production of the polypeptide, wherein the mutant strain comprises a polynucleotide encoding the polypeptide and one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions; and recovering the polypeptide from the cultivation medium.

[24] The method of paragraph 23, wherein the mutant comprises a modification of the first subtilisin-like serine protease gene.

[25] The method of paragraph 23 or 24, wherein the mutant comprises a modification of the first aspartic protease gene.

[26] The method of any of paragraphs 23-25, wherein the mutant comprises a modification of the trypsin-like serine protease gene.

[27] The method of any of paragraphs 23-26, wherein the mutant comprises a modification of the second subtilisin-like serine protease gene.

[28] The method of any of paragraphs 23-27, wherein the mutant comprises a modification of the second aspartic protease gene.

[29] The method of any of paragraphs 23-28, wherein the mutant comprises a modification of the first subtilisin-like serine protease gene, the first aspartic protease gene, the trypsin-like serine protease gene, the second subtilisin-like serine protease gene, and the second aspartic protease gene.

[30] The method of any of paragraphs 23-29, wherein the polypeptide is native or foreign to the *Trichoderma* strain.

[31] The method of any of paragraphs 23-30, wherein the *Trichoderma* strain is selected from the group consisting of *Trichoderma harzianum, Trichoderma koningii, Trichoderma longibrachiatum, Trichoderma reesei*, and *Trichoderma viride*.

[32] The method of any of paragraphs 23-31, wherein the *Trichoderma* strain is *Trichoderma reesei*.

[33] The method of any of paragraphs 23-32, wherein the mutant strain produces at least 25% less of the one or more (several) enzymes selected from the group consisting of the first subtilisin-like serine protease, the first aspartic protease, the trypsin-like serine protease, the second subtilisin-like serine protease, and the second aspartic protease compared to the parent *Trichoderma* strain when cultivated under identical conditions.

[34] The method of any of paragraphs 23-32, wherein the mutant strain is completely deficient in the one or more (several) enzymes selected from the group consisting of the first subtilisin-like serine protease, the first aspartic protease, the trypsin-like serine protease, the second subtilisin-like serine protease, and the second aspartic protease compared to the parent *Trichoderma* strain when cultivated under identical conditions.

[35] The method of any of paragraphs 23-34, wherein the first subtilisin-like serine protease gene is selected from the group consisting of: (a) a polypeptide comprising or consisting of an amino acid sequence having at least 60%, e.g., at least 65%, at least 70%, at least 75%, at least 80%, at least 85%, at least 90%, at least 95%, or 100% sequence identity to SEQ ID NO: 2 or the mature polypeptide thereof; (b) a polypeptide encoded by a polynucleotide that hybridizes under at least low stringency conditions, at least medium stringency conditions, at least medium-high stringency conditions, high stringency conditions, or very high stringency conditions with (i) SEQ ID NO: 1; (ii) the mature polypeptide coding sequence of SEQ ID NO: 1, (iii) the cDNA sequence of (i) or (ii), or (iv) a full-length complementary strand of (i), (ii), or (iii); and (c) a polypeptide encoded by a polynucleotide comprising or consisting of a nucleotide sequence having at least 60%, e.g., at least 65%, at least 70%, at least 75%, at least 80%, at least 85%, at least 90%, at least 95%, or 100% sequence identity to SEQ ID NO: 1 or the cDNA thereof, or the mature polypeptide coding sequence thereof.

[36] The method of any of paragraphs 23-35, wherein the first subtilisin-like serine protease comprises or consists of SEQ ID NO: 2 or the mature polypeptide thereof.

[37] The method of any of paragraphs 23-36, wherein the first aspartic protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 4 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 3; (ii) the mature polypeptide coding sequence of SEQ ID NO: 3, (iii) the cDNA sequence of (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 3 or the cDNA thereof, or the mature polypeptide coding sequence thereof.

[38] The method of any of paragraphs 23-37, wherein the first aspartic protease comprises or consists of SEQ ID NO: 4 or the mature polypeptide thereof.

[39] The method of any of paragraphs 23-38, wherein the trypsin-like serine protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 6 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 5; (ii) the mature polypeptide coding sequence of SEQ ID NO: 5, (iii) the cDNA sequence contained in (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 5 or the cDNA thereof, or the mature polypeptide coding sequence thereof.

[40] The method of any of paragraphs 23-39, wherein the trypsin-like serine protease comprises or consists of SEQ ID NO: 6 or the mature polypeptide thereof.

[41] The method of any of paragraphs 23-40, wherein the second subtilisin-like serine protease gene is selected from the group consisting of: (a) a polypeptide comprising or consisting of an amino acid sequence having at least 60%, e.g., at least 65%, at least 70%, at least 75%, at least 80%, at least 85%, at least 90%, at least 95%, or 100% sequence identity to SEQ ID NO: 100 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 99; (ii) the mature polypeptide coding sequence of SEQ ID NO: 99, (iii) the cDNA sequence of (i) or (ii), or (iv) a full-length complementary strand of (i), (ii), or (iii); and (c) a polypeptide encoded by a polynucleotide comprising or consisting of a nucleotide sequence having at least 60%, e.g., at least 65%, at least 70%, at least 75%, at least 80%, at least 90%, at least 95%, or 100% sequence identity to SEQ ID NO: 100 or the cDNA thereof, or the mature polypeptide coding sequence thereof.

[42] The method of any of paragraphs 23-41, wherein the second subtilisin-like serine protease comprises or consists of SEQ ID NO: 100 or the mature polypeptide thereof.

[43] The method of any of paragraphs 23-42, wherein the second aspartic protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 108 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 107; (ii) the mature polypeptide coding sequence of SEQ ID NO: 107, (iii) the cDNA sequence of (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 107 or the cDNA thereof, or the mature polypeptide coding sequence thereof.

[44] The method of any of paragraphs 23-43, wherein the second aspartic protease comprises or consists of SEQ ID NO: 108 or the mature polypeptide thereof.

[45] A method for obtaining a mutant of a parent *Trichoderma* strain, comprising: modifying one or more (several) genes selected from the group consisting of a first subtilisin-like serine protease gene, a first aspartic protease gene, a trypsin-like serine protease gene, a second subtilisin-like serine protease gene, and a second aspartic protease gene; and identifying a mutant strain from step (a) wherein the one or more (several) genes selected from the group consisting of the first subtilisin-like serine protease gene, the first aspartic protease gene, and the trypsin-like serine protease gene are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions.

[46] The method of paragraph 45, wherein the mutant comprises a modification of the first subtilisin-like serine protease gene.

[47] The method of paragraph 45 or 46, wherein the mutant comprises a modification of the first aspartic protease gene.

[48] The method of any of paragraphs 45-47, wherein the mutant comprises a modification of the trypsin-like serine protease gene.

[49] The method of any of paragraphs 45-48, wherein the mutant comprises a modification of the second subtilisin-like serine protease gene.

[50] The method of any of paragraphs 45-49, wherein the mutant comprises a modification of the second aspartic protease gene.

[51] The method of any of paragraphs 45-50, wherein the mutant comprises a modification of the first subtilisin-like serine protease gene, the first aspartic protease gene, the trypsin-like serine protease gene, the second subtilisin-like serine protease gene, and the second aspartic protease gene.

[52] The method of any of paragraphs 45-51, wherein the polypeptide is native or foreign to the *Trichoderma* strain.

[53] The method of any of paragraphs 45-52, wherein the *Trichoderma* strain is selected from the group consisting of *Trichoderma harzianum, Trichoderma koningii, Trichoderma longibrachiatum, Trichoderma reesei*, and *Trichoderma viride*.

[54] The method of any of paragraphs 45-53, wherein the *Trichoderma* strain is *Trichoderma reesei*.

[55] The method of any of paragraphs 45-54, wherein the mutant strain produces at least 25% less of the one or more (several) enzymes selected from the group consisting of the first subtilisin-like serine protease, the first aspartic protease, the trypsin-like serine protease, the second subtilisin-like serine protease, and the second aspartic protease compared to the parent *Trichoderma* strain when cultivated under identical conditions.

[56] The method of any of paragraphs 45-54, wherein the mutant strain is completely deficient in the one or more (several) enzymes selected from the group consisting of the first subtilisin-like serine protease, the first aspartic protease, the trypsin-like serine protease, the second subtilisin-like serine protease, and the second aspartic protease compared to the parent *Trichoderma* strain when cultivated under identical conditions.

[57] The method of any of paragraphs 45-56, wherein the first subtilisin-like serine protease gene is selected from the group consisting of: (a) a polypeptide comprising or consisting of an amino acid sequence having at least 60%, e.g., at least 65%, at least 70%, at least 75%, at least 80%, at least 85%, at least 90%, at least 95%, or 100% sequence identity to SEQ ID NO: 2 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 1; (ii) the mature polypeptide coding sequence of SEQ ID NO: 1, (iii) the cDNA sequence of (i) or (ii), or (iv) a full-length complementary strand of (i), (ii), or (iii); and (c) a polypeptide encoded by a polynucleotide comprising or consisting of a nucleotide sequence having at least 60%, e.g., at least 65%, at least 70%, at least 75%, at least 80%, at least 85%, at least 90%, at least 95%, or 100% sequence identity to SEQ ID NO: 1 or the cDNA thereof, or the mature polypeptide coding sequence thereof.

[58] The method of any of paragraphs 45-57, wherein the first subtilisin-like serine protease comprises or consists of SEQ ID NO: 2 or the mature polypeptide thereof.

[59] The method of any of paragraphs 45-58, wherein the first aspartic protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 4 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 3; (ii) the mature polypeptide coding sequence of SEQ ID NO: 3, (iii) the cDNA sequence of (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 3 or the cDNA thereof, or the mature polypeptide coding sequence thereof.

[60] The method of any of paragraphs 45-59, wherein the first aspartic protease comprises or consists of SEQ ID NO: 4 or the mature polypeptide thereof.

[61] The method of any of paragraphs 45-60, wherein the trypsin-like serine protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 6 or the mature polypeptide thereof; (b) a polypeptide encoded by a polynucleotide that hybridizes under at least low stringency conditions, at least medium stringency conditions, at least medium-high stringency conditions, high stringency conditions, or very high stringency conditions with (i) SEQ ID NO: 5; (ii) the mature polypeptide coding sequence of SEQ ID NO: 5, (iii) the cDNA sequence contained in (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 5 or the cDNA thereof, or the mature polypeptide coding sequence thereof.

[62] The method of any of paragraphs 45-61, wherein the trypsin-like serine protease comprises or consists of SEQ ID NO: 6 or the mature polypeptide thereof.

[63] The method of any of paragraphs 45-62, wherein the second subtilisin-like serine protease gene is selected from the group consisting of: (a) a polypeptide comprising or consisting of an amino acid sequence having at least 60%, e.g., at least 65%, at least 70%, at least 75%, at least 80%, at least 85%, at least 90%, at least 95%, or 100% sequence identity to SEQ ID NO: 100 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 99; (ii) the mature polypeptide coding sequence of SEQ ID NO: 99, (iii) the cDNA sequence of (i) or (ii), or (iv) a full-length complementary strand of (i), (ii), or (iii); and (c) a polypeptide encoded by a polynucleotide comprising or consisting of a nucleotide sequence having at least 60%, e.g., at least 65%, at least 70%, at least 75%, at least 80%, at least 85%, at least 90%, at least 95%, or 100% sequence identity to SEQ ID NO: 100 or the cDNA thereof, or the mature polypeptide coding sequence thereof.

[64] The method of any of paragraphs 45-63, wherein the second subtilisin-like serine protease comprises or consists of SEQ ID NO: 100 or the mature polypeptide thereof.

[65] The method of any of paragraphs 45-64, wherein the second aspartic protease gene is selected from the group consisting of: (a) a polypeptide comprising an amino acid sequence having at least 60%, e.g., at least 65%, at least 70%, at least 75%, at least 80%, at least 85%, at least 90%, at least 95%, or 100% sequence identity to SEQ ID NO: 108 or the mature polypeptide thereof; (b) a polypeptide encoded by a polynucleotide that hybridizes under at least low stringency conditions, at least medium stringency conditions, at least medium-high stringency conditions, at least high stringency conditions, or at least very high stringency conditions with (i) SEQ ID NO: 3; (ii) the mature polypeptide coding sequence of SEQ ID NO: 107, (iii) the cDNA sequence of (i) or (ii), or (iv) a full-length complementary strand of (i), (ii), or (iii); and (c) a polypeptide encoded by a polynucleotide comprising a nucleotide sequence having at least 60%, e.g., at least 65%, at least 70%, at least 75%, at least 80%, at least 85%, at least 90%, at least 95%, or 100% sequence identity to SEQ ID NO: 107 or the cDNA thereof, or the mature polypeptide coding sequence thereof.

[66] The method of any of paragraphs 45-65, wherein the second aspartic protease comprises or consists of SEQ ID NO: 108 or the mature polypeptide thereof.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties.

What is claimed is:

1. An isolated mutant strain, of a parent *Trichoderma* strain comprising a polynucleotide encoding a polypeptide and a first subtilisin-like serine protease gene, a first aspartic protease gene, a trypsin-like serine protease gene, a second subtilisin-like serine protease gene, and a second aspartic protease gene, wherein the first subtilisin-like serine protease gene, the first aspartic protease gene, the trypsin-like serine protease gene, the second subtilisin-like serine protease gene, and the second aspartic protease gene are modified rendering the mutant strain at least 95% deficient in the production of each of the first subtilisin-like serine protease, the first aspartic protease, the trypsin-like serine protease, the second subtilisin-like serine protease, and the second aspartic protease, respectively, compared to the parent *Trichoderma* strain when cultivated under identical conditions;

wherein the first subtilisin-like serine protease is selected from the group consisting of:
(a) a polypeptide comprising an amino acid sequence having at least 95% sequence identity to SEQ ID NO: 2 or amino acids 20 to 882 of SEQ ID NO: 2; and
(b) a polypeptide encoded by a polynucleotide comprising a nucleotide sequence having at least 95% sequence identity to SEQ ID NO: 1 or nucleotides 58 to 2774 of SEQ ID NO: 1, or the cDNA thereof;

wherein the first aspartic protease is selected from the group consisting of:
(a) a polypeptide comprising an amino acid sequence having at least 95% sequence identity to SEQ ID NO: 4 or amino acids 21 to 407 of SEQ ID NO: 4; and
(b) a polypeptide encoded by a polynucleotide comprising a nucleotide sequence having at least 95% sequence identity to SEQ ID NO: 3 nucleotides 61 to 1299 of SEQ ID NO: 3, or the cDNA thereof;

wherein the trypsin-like serine protease is selected from the group consisting of:
(a) a polypeptide comprising an amino acid sequence having at least 95% sequence identity to SEQ ID NO: 6 or amino acids 20 to 259 of SEQ ID NO: 6; and
(b) a polypeptide encoded by a polynucleotide comprising a nucleotide sequence having at least 95% sequence identity to SEQ ID NO: 5 or nucleotides 58 to 930 of SEQ ID NO: 5, or the cDNA thereof;

wherein the second subtilisin-like serine protease is selected from the group consisting of:
(a) a polypeptide comprising of an amino acid sequence having at least 95% sequence identity to SEQ ID NO: 100 or amino acids 16 to 540 of SEQ ID NO: 100; and
(b) a polypeptide encoded by a polynucleotide comprising a nucleotide sequence having at least 95% sequence identity to SEQ ID NO: 99 or nucleotides 46 to 1681 of SEQ ID NO: 99 or the cDNA thereof;

wherein the second aspartic protease is selected from the group consisting of:
(a) a polypeptide comprising an amino acid sequence having at least 95% sequence identity to SEQ ID NO: 108 or amino acids 18 to 395 of SEQ ID NO: 108; and
(b) a polypeptide encoded by a polynucleotide comprising a nucleotide sequence having at least 95% sequence identity to SEQ ID NO: 107 or nucleotides 52 to 1339 of SEQ ID NO: 107, or the cDNA thereof; and
wherein the polypeptide is native or foreign to the parent Trichoderma strain.

2. The isolated mutant of claim 1, wherein the parent Trichoderma strain is selected from the group consisting of Trichoderma harzianum, Trichoderma koningii, Trichoderma longibrachiatum, Trichoderma reesei, and Trichoderma viride.

3. The isolated mutant of claim 1, wherein the parent Trichoderma strain is Trichoderma reesei.

4. The isolated mutant of claim 1, which is completely deficient in the first subtilisin-like serine protease, the first aspartic protease, the trypsin-like serine protease, the second subtilisin-like serine protease, and the second aspartic protease compared to the parent Trichoderma strain when cultivated under identical conditions.

5. The isolated mutant of claim 1, wherein the first subtilisin-like serine protease comprises
SEQ ID NO: 2 or amino acids 20 to 882 of SEQ ID NO: 2.

6. The isolated mutant of claim 1, wherein the first aspartic protease comprises
SEQ ID NO: 4 or amino acids 21 to 407 of SEQ ID NO: 4.

7. The isolated mutant of claim 1, wherein the trypsin-like serine protease comprises
SEQ ID NO: 6 or amino acids 20 to 259 of SEQ ID NO: 6.

8. The isolated mutant of claim 1, wherein the second subtilisin-like serine protease comprises
SEQ ID NO: 100 or amino acids 16 to 540 of SEQ ID NO: 100.

9. The isolated mutant of claim 1, wherein the second aspartic protease comprises
SEQ ID NO: 108 or amino acids 18 to 395 of SEQ ID NO: 108.

10. A method of producing a polypeptide, comprising:
(a) cultivating the isolated mutant of claim 1 in a medium for the production of the polypeptide; and
(b) recovering the polypeptide from the cultivation medium.

11. The method of claim 10, wherein the parent Trichoderma strain is selected from the group consisting of Trichoderma harzianum, Trichoderma koningii, Trichoderma longibrachiatum, Trichoderma reesei, and Trichoderma viride.

12. The method of claim 10, wherein the parent Trichoderma strain is Trichoderma reesei.

13. The method of claim 10, wherein the mutant is completely deficient in the first subtilisin-like serine protease, the first aspartic protease, the trypsin-like serine protease, the second subtilisin-like serine protease, and the second aspartic protease compared to the parent Trichoderma strain when cultivated under identical conditions.

14. The method of claim 10, wherein the first subtilisin-like serine protease comprises SEQ ID NO: 2 or amino acids 20 to 882 of SEQ ID NO: 2.

15. The method of claim 10, wherein the first aspartic protease comprises SEQ ID NO: 4 or amino acids 21 to 407 of SEQ ID NO: 4.

16. The method of claim 10, wherein the trypsin-like serine protease comprises SEQ ID NO: 6 or amino acids 20 to 259 of SEQ ID NO: 6.

17. The method of claim 10, wherein the second subtilisin-like serine protease comprises SEQ ID NO: 100 or amino acids 16 to 540 of SEQ ID NO: 100.

18. The method of claim 10, wherein the second aspartic protease comprises SEQ ID NO: 108 or amino acids 18 to 395 of SEQ ID NO: 108.

19. A method for obtaining the mutant of claim 1, comprising:
(a) modifying the first subtilisin-like serine protease gene, the first aspartic protease gene, the trypsin-like serine protease gene, the second subtilisin-like serine protease gene, and the second aspartic protease gene in the parent Trichoderma strain; and
(b) identifying a mutant strain from step (a) wherein the first subtilisin-like serine protease gene, the first aspartic protease gene, and the trypsin-like serine protease gene are modified rendering the mutant strain deficient in the production of the first subtilisin-like serine protease, the first aspartic protease, a trypsin-like serine protease, the second subtilisin-like serine protease, and the second aspartic protease, respectively, compared to the parent Trichoderma strain when cultivated under identical conditions.

20. The method of claim 19, wherein the parent Trichoderma strain is selected from the group consisting of Trichoderma harzianum, Trichoderma koningii, Trichoderma longibrachiatum, Trichoderma reesei, and Trichoderma viride.

21. The method of claim 19, wherein the parent Trichoderma strain is Trichoderma reesei.

22. The method of claim 19, wherein the mutant is completely deficient in the first subtilisin-like serine protease, the first aspartic protease, the trypsin-like serine protease, the second subtilisin-like serine protease, and the second aspartic protease compared to the parent Trichoderma strain when cultivated under identical conditions.

23. The method of claim 19, wherein the first subtilisin-like serine protease comprises SEQ ID NO: 2 or amino acids 20 to 882 of SEQ ID NO: 2; the first aspartic protease comprises SEQ ID NO: 4 or amino acids 21 to 407 of SEQ ID NO: 4; the trypsin-like serine protease comprises SEQ ID NO: 6 or amino acids 20 to 259 of SEQ ID NO: 6; the second subtilisin-like serine protease comprises SEQ ID NO: 100 or amino acids 16 to 540 of SEQ ID NO: 100; and the second aspartic protease comprises SEQ ID NO: 108 or amino acids 18 to 395 of SEQ ID NO: 108.

* * * * *